United States Patent [19]

Ogawa et al.

[11] Patent Number: 5,101,026
[45] Date of Patent: Mar. 31, 1992

[54] GANGLIOSIDE RELATED COMPOUNDS AND METHOD OF PRODUCING THE SAME

[75] Inventors: Tomoya Ogawa, Musashino; Mamoru Sugimoto, Niiza; Masaaki Numata, Kawagoe; Masayoshi Ito, Kunitachi; Yoshiyasu Shitori, Tokyo; Shigeki Nunomura, Wako, all of Japan

[73] Assignee: MECT Corporation, Tokyo, Japan

[21] Appl. No.: 82,289

[22] Filed: Aug. 6, 1987

[30] Foreign Application Priority Data

Aug. 6, 1986 [JP] Japan .................. 61-184501
Aug. 6, 1986 [JP] Japan .................. 61-184502
Mar. 9, 1987 [JP] Japan .................. 62-53409
Mar. 9, 1987 [JP] Japan .................. 62-53410

[51] Int. Cl.$^5$ .............. C07H 13/06; C07H 5/06; C07H 15/10; C07H 3/06
[52] U.S. Cl. .................. 536/53; 536/4.1; 536/18.4; 536/55; 536/55.3; 536/124
[58] Field of Search ............ 514/25; 536/4.1, 17.2, 536/17.9, 18.2, 53, 55, 124, 55.3, 18.4

[56] References Cited

U.S. PATENT DOCUMENTS

| | | | |
|---|---|---|---|
| 4,415,733 | 11/1983 | Tayot | 536/53 |
| 4,593,091 | 6/1986 | della Valle et al. | 536/53 |
| 4,713,374 | 12/1987 | della Valle et al. | 514/54 |
| 4,716,223 | 12/1987 | della Valle et al. | 536/53 |
| 4,728,641 | 3/1988 | Tubaro et al. | 514/54 |
| 4,751,290 | 6/1988 | Ogawa et al. | 536/17.9 |
| 4,762,822 | 8/1988 | Ettinger | 514/25 |

FOREIGN PATENT DOCUMENTS 63-35588  2/1988  Japan .
63-35589  2/1988  Japan .
63-159402 7/1988  Japan .

OTHER PUBLICATIONS

Lemieux et al.; Can. J. Chem. 57; 1244–1251 (1979).
(List continued on next page.)

Primary Examiner—Johnnie R. Brown
Assistant Examiner—Nancy S. Carson
Attorney, Agent, or Firm—Oblon, Spivak, McClelland, Maier & Neustadt

[57] ABSTRACT

The present invention relates to ganglioside related compounds having, for example, the following formula:

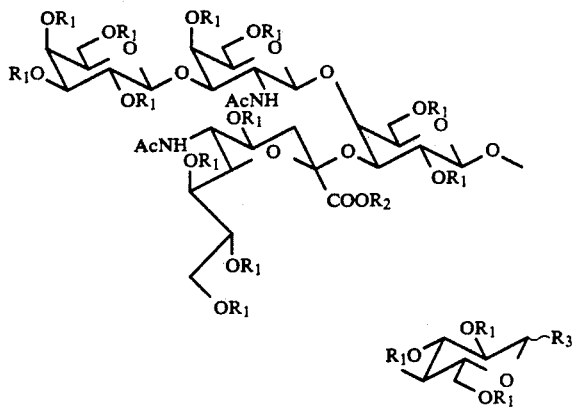

where $R_1$ represents H or $COCH_3$ (hereinafter abbreviated to "AC"); $R_2$ represents H or $CH_3$; and $R_3$ represents —OH,

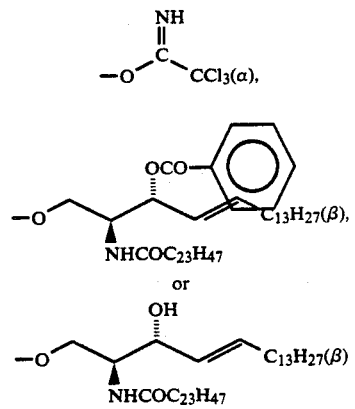

These ganglioside related compounds are useful as membrane receptors, tumor markers, cell growth controlling substances, etc., and useful for immunotherapy for cancer, etc.

3 Claims, 19 Drawing Sheets

OTHER PUBLICATIONS

Jennings et al.; Carb. Res. 121:233–241 (1983).
Sabesan et al.; Can. J. Chem. 62:644–654 (1984).
Maranduba et al.; Carb. Res. 135:330–336 (1985).
Dahmen et al.; Carb. Res. 138:17–28 (1985).
Sugimoto et al.; Carbohydrate Research 156:c1–c5 Nov. 15, 1986.
Sugimoto et al.; Tennen Yuki Kagobutsu Toronkai Koen Yoshishu 28th, pp. 604–610 (1986).
Sonnino et al.; J. Lipid Res. 26:248–257 (1985).
Journal of Lipid Research, vol, 26, No. 2, 1985, S. Sonnino et al.: "Preparation of GMI Ganglioside Molecular Species having Homogeneour Fatty Acid and Long Chain Base Moieties". pp. 248-257.
Carohydrate Research, vol. 113, 1983, pp. 173–188, Elsevier Scientific Publishing Co, Amsterdam, NL; L. O. Sillerrud et al.: "Comparison of the 13C–N.M.R. Spectra of Gangliosides GMI with Tose of GMI–Oligosaccharide and Asuaki GMI".
Chemical Abstracts, vol. 108, No. 1, Jan. 4, 1988, p. 602 Abstract No. 6300t, Columbus, Ohio, U.S.; M. Sugimoto et al.: "Total Synthesis of Gangliosides", & Tennen Yuki Kagobutsu Toronkai Koen Yoshishu 1986, 28th, 604–610.
Carbohydrate Research, vol. 156, 1986, pp. c1–c5, Elsevier Science Publishers, B. V., Amsterda, NL; M. Sugimoto et al,: "Total Synthesis of Gangliosides GM1 & GM2".
Tetrahedron Letters, No. 20, 1978, pp. 1717–1720, Pergamon Press Ltd., GB; M. M. Ponpipom et al.: "Synthesis of Paragloboside Analogs".
The Journal of Biological Chemistry, vol. 260, No. 2, Jan. 25, 1985, pp. 1067–1082, American Society of Biological Chemists, Inc. U.S.; M. N. Fukuda et al.: "Structures of Glycosphingolipids Isolated from Human Granuocytes. The Presence of a Series of Linear poly-N-Acetyllactosaminylceramide and its Significance in Glycolipids of Whole Blood Cells".
*Biochem. Biophys. Res. Commun.*, vol. 113, pp. 791–798 (1983).
*Science*, vol. 230, pp. 1285–1287 (1985).
*Carbohydrate Research*, vol. 113, pp. 173–188 (1983).
Search Report for European Patent Application 87111254.6.

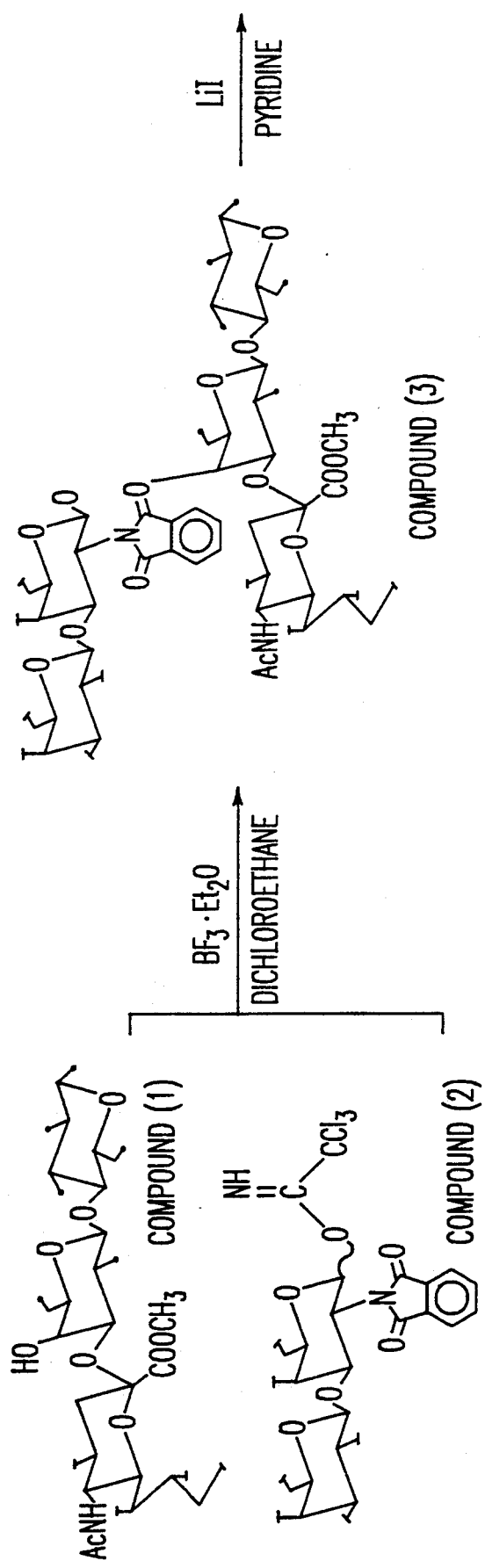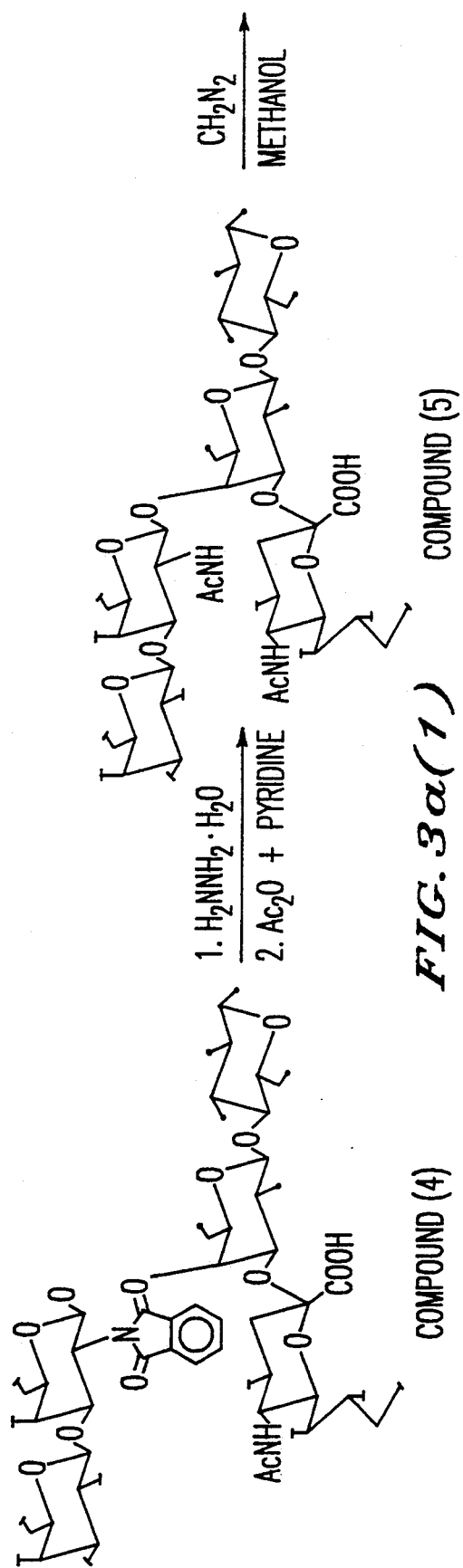
FIG. 3a(1)

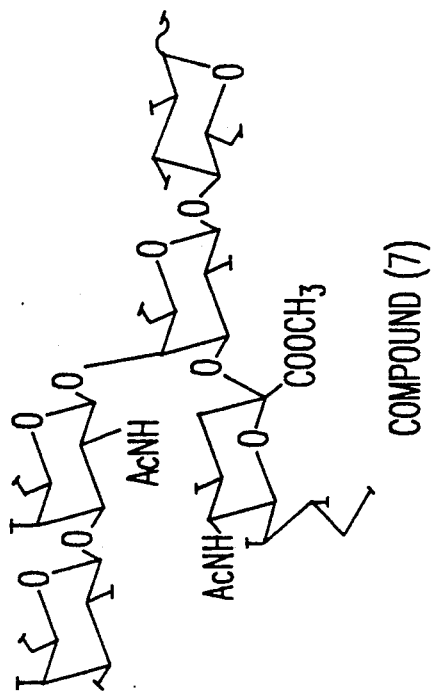
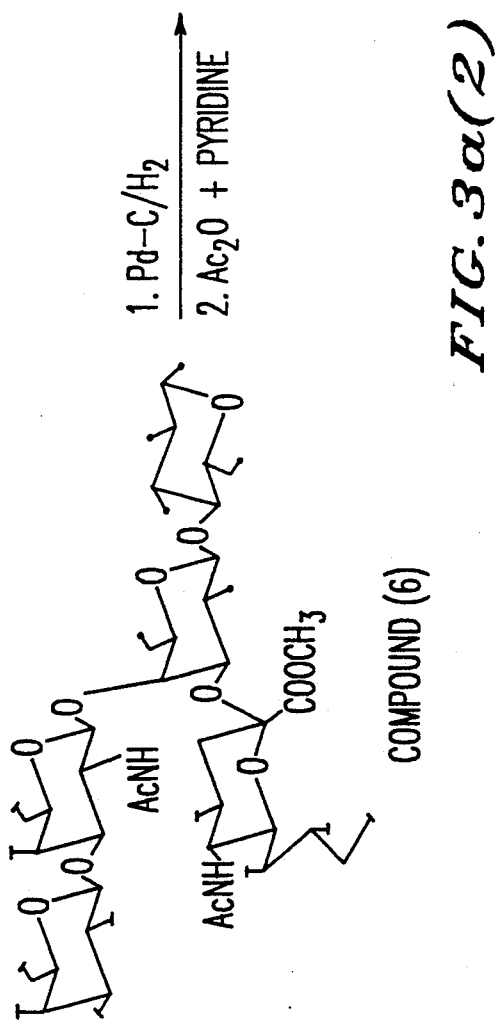
FIG.3a(2)

COMPOUND (16)

GANGLIOSIDE RELATED COMPOUNDS AND METHOD OF PRODUCING THE SAME

BACKGROUND OF THE INVENTION

The present invention relates to ganglioside related compounds.

In general, glycolipids of mammal cells are the substances which are formed by glycoside linkage of various combinations of various sugars such as glucose, galactose, N-acetylglucosamine, N-acetylgalactosamine, fucose and sialic acid, with a lipid structure called ceramide which in turn is formed through an amide linkage of fatty acid with long-chain aminoalcohol known as sphingosine. And, these glycolipids belong to a so-called sphingoglycolipid. Among these glycolipids, those which have sialic acid are specifically called gangliosides.

Generally, such compounds exist locally in the outer molecular layer of the bi-layer structure of the cell membrane. The current study has proved that these compounds play important roles in cells, such as identification of cells, reception and response to information, receptor function, differentiation, and proliferation, malignant alteration and behavior of cells, and so forth.

Among these gangliosides, Ganglioside $GM_1$ was first discovered by Kuhn, Wiegandt and others in human brains and calf brains. It is known that Ganglioside $GM_1$ has a structure expressed by the following general formula:

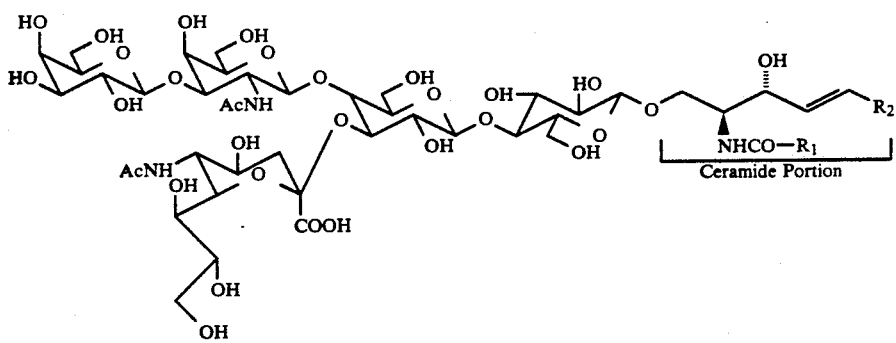

However, $R_1$ and $R_2$ of the ceramide portion have not yet been specified.

In fact, it is known that Ganglioside $GM_1$ acts as a receptor. For instance, it is known that this substance is bonded to cholera toxin protein, and changes the conformation of the protein, thereby activating adenylate cyclase and raising the level of generation of cyclic AMP, which in turn causes dehydration. Recent studies have also made it clear that Ganglioside $GM_1$ acts as an intermediary in proliferation of brain glandula lymphocytes (SCIENCE, Vol. 230, pp. 1285–1287, published on Dec. 13, 1985).

Ganglioside $GM_2$ can also be isolated from brains, nervous tissues, brains of patients suffering from Tay Sach disease, lymphomas of mice, fibroblasts, livers of rats, and cancer tissues of livers. It is known that Ganglioside $GM_2$ has a structure expressed by the following general formula:

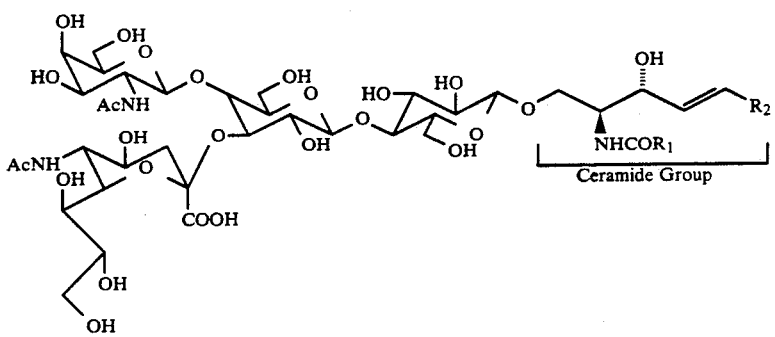

However, the $R_1$ and $R_2$ of the ceramide group have not yet been specified.

It is considered that Ganglioside $GM_2$ is able to function as a cancer-related antigen marker useful for diagnosis and therapy of cancers. It is also known that, since the action of interferon against virus infection is neutralized by Ganglioside $GM_2$, the production of interferon can be induced by adding Ganglioside $GM_2$ to mice cells which are inactive to interferon.

In spite of the fact that Gangliosides $GM_1$ and $GM_2$ are known to have various biochemical functions, it has been difficult to isolate Gangliosides $GM_1$ and $GM_2$ and their related compounds from a living body and refine them, and complete synthesis of Gangliosides $GM_1$ and $GM_2$ and their related compounds has not been accomplished, yet. Fine syntheses of Gangliosides $GM_1$ and $GM_2$ compounds related thereto in are absolutely necessary to clarify the correlation between the molecular structures of these Gangliosides and biological information.

On the other hand, a ganglioside called a cancer antigen which can be isolated, from colon and liver cancer tissues is peculiar to those tissues. It is thought that this substance is closely related to the immune system of a body suffering from such a disease. However, it has been difficult to obtain this compound through the operations of extraction, isolation and purification. The supply of this compound and analogous compounds as a pure substance enables them to be used for tracing antigen-antibody reactions and preparing monoclonal antibodies, and is thus thought to be very important from the viewpoint of pharmaceutics (Biochem. Biophys. Res. Commun., vol. 113, 791-798 (1983)).

Further, it has been found that Ganglioside $GD_{1a}$ is isolated from nervous tissues or the brain of a patient suffering from Tay Sach disease.

It is thought that Ganglioside $GD_{1a}$ can serve as a cancer related antigen marker for diagnosis and remedies of cancer.

Although it is found that Ganglioside $GD_{1a}$ has various biological functions, it is difficult to isolate Ganglioside $GD_{1a}$ and compounds related thereto from living bodies and to purify them, and the complete analyses thereof have not so far been achieved.

Therefore, the fine syntheses of those gangliosides and compounds related thereto in a sterically selective manner are absolutely necessary for clarification of the correlation between biological information and the molecular structures of these gangliosides compounds.

SUMMARY OF THE INVENTION

Accordingly, an object of the present invention is to provide gangliosides and their related compounds, and processes for manufacturing these compounds.

The present invention relates to the following compounds and processes:

1. Ganglioside $GM_1$ related compounds having the following general formula:

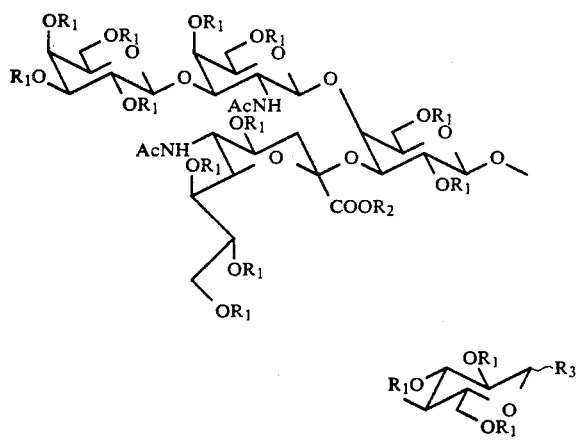

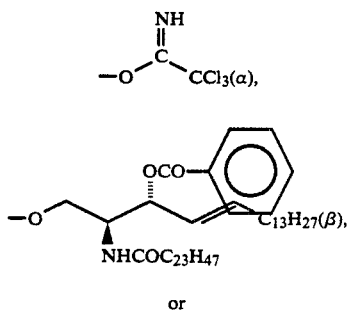

where $R_1$ represents H or $COCH_3$ (hereinafter abbreviated to "Ac"); $R_2$ represents H or $CH_3$; and $R_3$ represents either —OH,

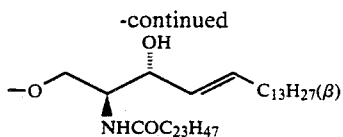

or

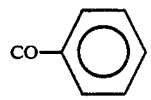

2. Method of producing Ganglioside $GM_1$ related compounds, comprising the following steps:
   (a) bringing Compound (1) expressed by a general formula (1) as give below:

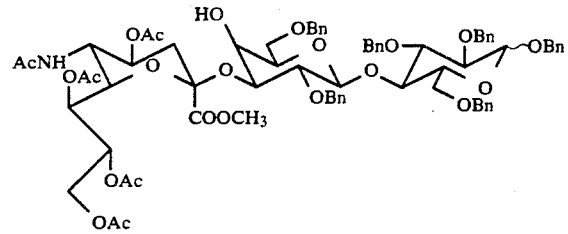

where Ac represents $COCH_3$ and Bn represents

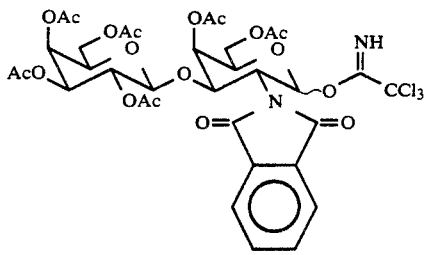

into reaction with a compound (2) expressed by a formula (2) as given below:

so as to obtain a compound (3) expressed by a formula (3) as given in Formula Table below;

(b) subjecting the compound 3) to demethylation so as to obtain a compound (4) expressed by a formula (4) as given in Formula Table below;

substituting the phthalic acid imide group of the compound (4) with an amino group and subsequently subjecting it to acetylation so as to obtain a compound (5) expressed by a formula (5) as given in Formula Table below;

(d) substituting the carboxyl group of the compound (5) with a methyl ester group so as to obtain a compound (6) expressed by a formula (6) as given in Formula Table below;

(e) subjecting the compound (6) to debenzoylation and subsequently to acetylation so as to obtain a compound (7) expressed by a formula (7) as given in Formula Table below;

(f) treating the compound (7) with hydrazinium acetate so as to obtain a compound (8) expressed by a formula (8) as given in Formula Table below;

(g) treating the compound (8) with CC13CN and either NaH or 1,8-diazabicyclo (5,4,0) undecatriene so as to obtain a compound (9) expressed by a formula (9) as given in Formula Table below;

(h) bringing a benzoylated ceramide compound (10) expressed by a formula (10) as given below:

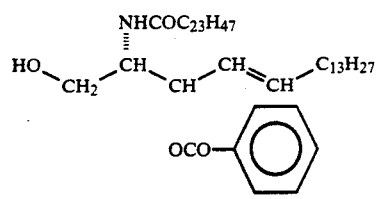

into reaction with the compound (9) so as to obtain a compound (11) expressed by a formula (11) as given in Formula Table below; and (i) subjecting the compound (11) to debenzoylation, deacetylation, and demethylation.

_Formula Table_

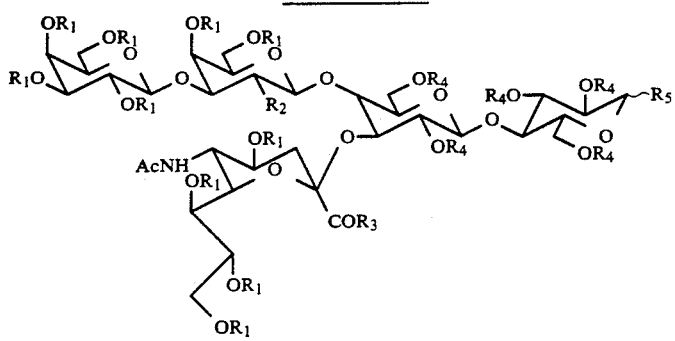

Formula (3): $R_1$ represents $COCH_3$ (Ac), $R_2$ represents

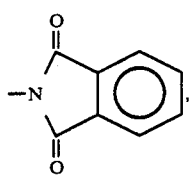

$R_3$ represents $OCH_3$, $R_4$ represents

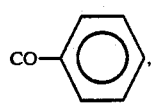

and $R_5$ represents

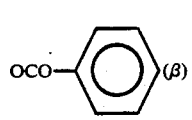

Formula (4): $R_1$ represents $COCH_3$, $R_2$ represents

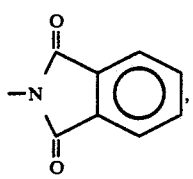

$R_3$ represents OH, $R_4$ represents

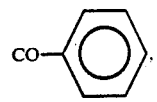

and $R_5$ represents

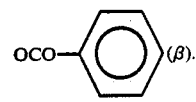

Formula (5): $R_1$ represents $COCH_3$, $R_2$ represents —NHAc, $R_3$ represents $OCH_3$, $R_4$ represents

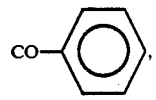

and $R_5$ represents

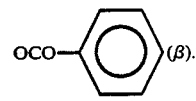

Formula (6): $R_1$ represents $COCH_3$, $R_2$ represents —NHAc, $R_3$ represents $OCH_3$, $R_4$ represents

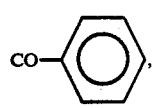

and $R_5$ represents

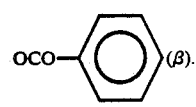

Formula (7): $R_1 = R_4$ and they represent $COCH_3$, $R_2$ represents —NHAc, $R_3$ represents $OCH_3$, and $R_5$ represents $OCOCH_3$.

Formula (8): $R_1=R_4$ and they represent $COCH_3$, $R_2$ represents NHAc, $R_3$ represents $OCH_3$, and $R_5$ represents OH.

Formula (9): $R_1=R_4$ and they represent $COCH_3$ $R_2$ represents NHAc, $R_3$ represents $OCH_3$, and $R_5$ represents

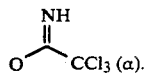

Formula (11): $R_1=R_4$ and they represent $COCH_3$, $R_2$ represents —NHAc, $R_3$ represents $OCH_3$, and $R_5$ represents

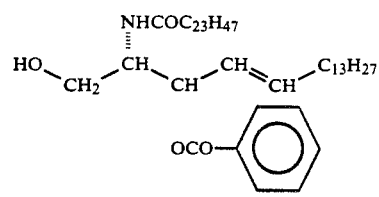

into reaction with Compound (9), so as to obtain a Compound (11) expressed by Formula (11) as given in the Formula Table; and (e) subjecting Compound (11) to debenzoylation, deacetylation, and demethylation.

Formula Table

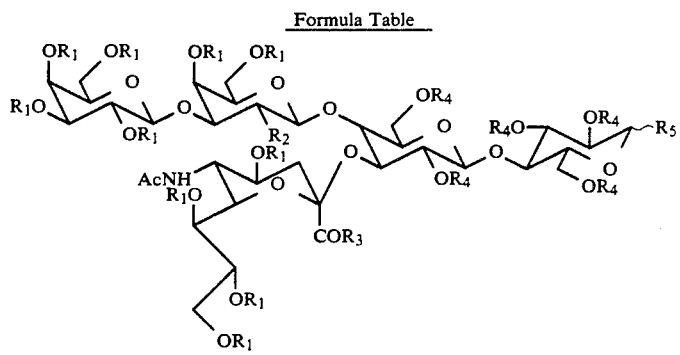

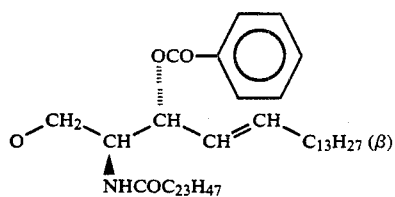

Formula (12): $R_1=R_4$ and they represent H, $R_2$ represents NHAc, $R_3$ represents OH, and $R_5$ represents

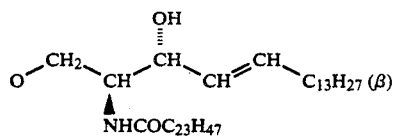

3. Another method of producing ganglioside related compounds, comprising the following steps:
  (a) subjecting Compound (6) expressed by Formula (6) as given in Formula Table below to debenzoylation and subsequently to acetylation so as to obtain Compound (7) expressed by Formula (7) as given in the Formula Table;
  (b) treating Compound (7) with hydrazinium acetate so as to obtain Compound (8) expressed by Formula (8) as given in the Formula Table;
  (c) treating Compound (8) with $CCl_3CN$ and either NaH or 1,8-diazabicyclo (5,4,0) undecatriene so as to obtain Compound (9) expressed by Formula (9) as given in the Formula Table;
  (d) bringing a benzoylated ceramide compound (10) having a general formula (10) below:

Formula (6): $R_1$ represents $COCH_3$, $R_2$ represents —NHAc, $R_3$ represents $OCH_3$, $R_4$ represents

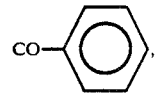

and $R_5$ represents

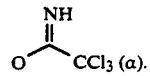

Formula (7): $R_1=R_4$ and they represent $COCH_3$, $R_2$ represents —NHAc, $R_3$ represents $OCH_3$, and $R_5$ represents $OCOCH_3$.

Formula (8): $R_1=R_4$ and they represent $COCH_3$, $R_2$ represents —NHAc, $R_3$ represents $OCH_3$, and $R_5$ represents OH.

Formula (9): $R_1=R_4$ and they represent $COCH_3$, $R_2$ represents NHAc, $R_3$ represents $OCH_3$, and $R_5$ represents

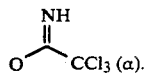

Formula (11): $R_1=R_4$ and they represent $COCH_3$, $R_2$ represents —NHAc, $R_3$ represents $OCH_3$, and $R_5$ represents

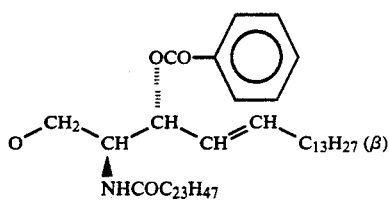

Formula (12): $R_1 = R_4$ and they represent H, $R_2$ represents —NHAc, $R_3$ represents OH, and $R_5$ represents

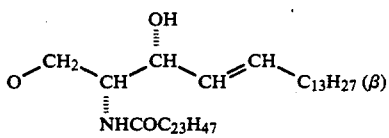

4. Ganglioside $GM_2$ related compounds having the following general formula:

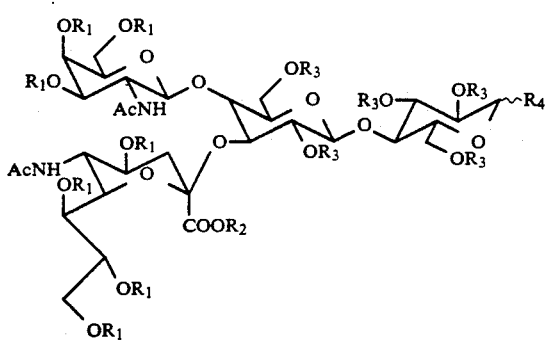

where,
(1) $R_1$ represents $COCH_3$, $R_2$ represents H or $CH_3$, $R_3$ represents $CH_2—C_6H_5$, and $R_4$ represents $OCH_2C_6H_5$ ($\beta$);
(2) $R_1$ represents $COCH_3$, $R_2$ represents $CH_3$, $R_3$ represents $COCH_3$, and $R_4$ represents $OCOCH_3$;
(3) $R_1$ represents $COCH_3$, $R_2$ represents $CH_3$, $R_3$ represents $COCH_3$, and $R_4$ represents OH;
(4) $R_1$ represents $COCH_3$, $R_2$ represents $CH_3$, $R_3$ represents $COCH_3$, and $R_4$ represents

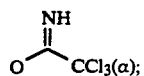

(5) $R_1$ is $COCH_3$, $R_2$ represents $CH_3$, $R_3$ represents $COCH_3$, and $R_4$ represents

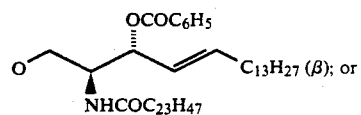

(6) $R_1 = R_2 \leqq R_3$ and they represent H, and $R_4$ represent

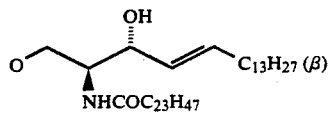

5. Method of producing Ganglioside $GM_2$ related compounds having a general formula (16) as given below:

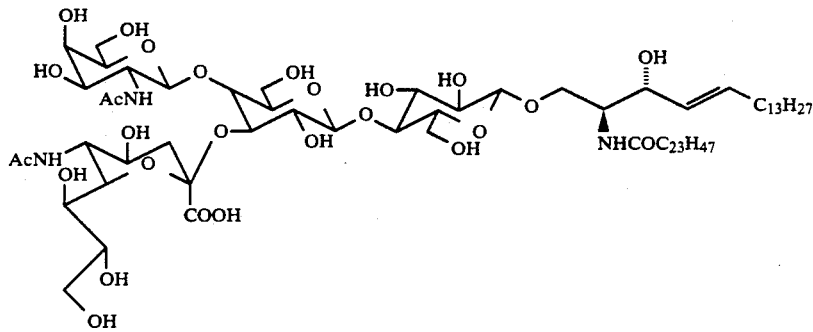

which method comprises the steps of:
(a)
1. treating Compound (6) expressed by Formula (6) as given in Formula Table below with an acetylating agent so as to obtain a mixture of Compound (7) expressed by Formula (7) as given in the Formula Table and Compound (8) expressed by Formula (8) as given in the Formula Table, treating each of Compounds (7) and (8) further with an acetylating agent so as to obtain Compound (9) expressed by Formula (9) as given in the Formula Table and Compound (10) expressed by Formula (10) as given in the Formula Table below, and subjecting Compound (9) alone to methyl-esterification so as to obtain Compound (10), or
2. acetylating and then methyl-esterifying Compound (6) so as to obtain Compound (8), and acetylating Compound (8) so as to obtain Compound (10);
(b) subjecting Compound (10) to debenzylation and then acetylation, thereby obtaining Compound (11) expressed by Formula (11) as given in the Formula Table;
(c) subjecting Compound (11) to hydroxylation, thereby obtaining Compound (12) expressed by Formula (12) as given in the Formula Table;
(d) bringing trichloroacetonitril into reaction with Compound (12), thereby obtaining Compound (13) expressed by Formula (13) as given in the Formula Table;
(e) bringing Compound (14) expressed by the following formula:

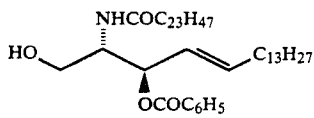

into reaction with Compound (13), thereby obtaining Compound (15) expressed by Formula (15) as given in the Formula Table; and (f) subjecting Compound (15) to debenzoylation and deacetylation.

Formula Table I

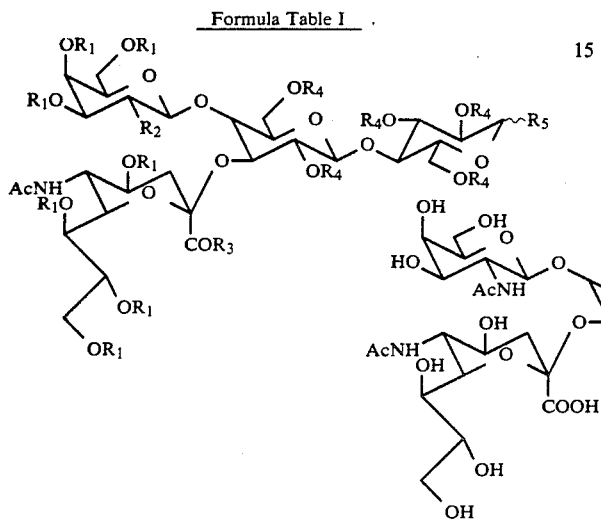

Formula (6): $R_1$ represents H, $R_2$ represents OH, $R_4$ represents $CH_2-C_6H_5$, and $R_5$ represents $OCH_2C_6H_5(\beta)$.

Formula (7): $R_1$ represents H, $R_2$ represents NHAc, $R_3$ represents OH, $R_4$ represents $CH_2C_6H_5$, and $R_5$ represents $OCH_2C_6H_5(\beta)$.

Formula (8): $R_1$ represents H, $R_2$ represents NHAc, $R_3$ represents $OCH_3$, $R_4$ represents $CH_2C_6H_5$, and $R_5$ represents $OCH_2C_6H_5(\beta)$.

Formula (9): $R_1$ represents $COCH_3$, $R_2$ represents NHAc, $R_3$ represents OH, $R_4$ represents $CH_2C_6H_5$, and $R_5$ represents $OCH_2C_6H_5(\beta)$.

Formula (10): $R_1$ represents $COCH_3$, $R_2$ represents NHAc, $R_3$ represents $OCH_3$, $R_4$ represents $CH_2C_6H_5$, and $R_5$ represents $OCH_2C_6H_5(\beta)$.

Formula (11): $R_1$ represents $COCH_3$, $R_2$ represents NHAc, $R_3$ represents $OCH_3$, $R_4$ represents $COCH_3$, and $R_5$ represents $OCOCH_3$.

Formula (12): $R_1$ represents $COCH_3$, $R_2$ represents NHAc, $R_3$ represents $OCH_3$, $R_4$ represents $COCH_3$, and $R_5$ represents OH.

Formula (13): $R_1$ represents $COCH_3$, $R_2$ represents NHAc, $R_3$ represents $OCH_3$, $R_4$ represents $COCH_3$, and $R_5$ represents

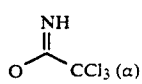

Formula (15): $R_1$ represents $COCH_3$, $R_2$ represents NHAc, $R_3$ represents $OCH_3$, $R_4$ represents $COCH_3$, and $R_5$ represents

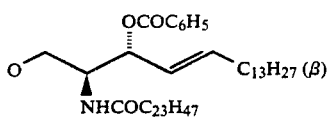

6. Another method of producing Ganglioside GM2 related compounds having a general formula (16) as given below:

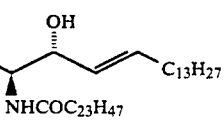

which method comprises the steps of:
(a) subjecting Compound (10) expressed by Formula (10) as given in Formula Table II below to debenzylation and then acetylation, thereby obtaining Compound (11) expressed by the Formula (11) as given in the Formula Table II;
(b) subjecting Compound 11) to hydroxylation, thereby obtaining Compound (12) expressed by Formula (12) as given in the Formula Table II;
(c) bringing trichloroacetonitril into reaction with Compound (12), thereby obtaining Compound (13) expressed by Formula (13) as given in the Formula Table II;
(d) bringing Compound (14) expressed by the following formula:

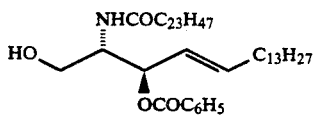

into reaction with Compound (13), thereby obtaining Compound (15) expressed by Formula (15) as given in the Formula Table II; and
(e) subjecting Compound (15) to debenzoylation and deacetylation.

Formula Table II

-continued

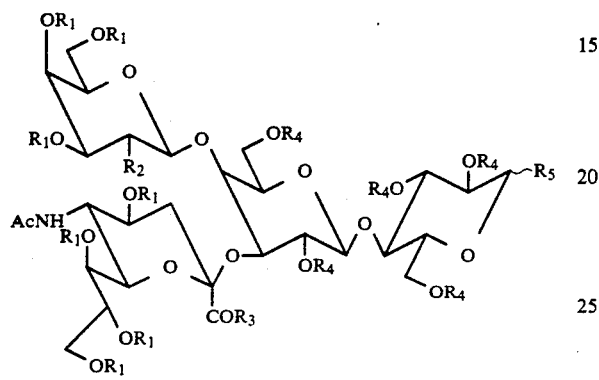

Formula (10): $R_1$ represents $COCH_3$, $R_2$ represents NHAc, $R_3$ represents $OCH_3$, $R_4$ represents $CH_2C_6H_5$, and $R_5$ represents $OCH_2C_6H_5(\beta)$.

Formula (11): $R_1$ represents $COCH_3$, $R_2$ represents NHAc, $R_3$ represents $OCH_3$, $R_4$ represents $COCH_3$, and $R_5$ represents $OCOCH_3$.

Formula (12): $R_1$ represents $COCH_3$, $R_2$ represents NHAc, $R_3$ represents $OCH_3$, $R_4$ represents $COCH_3$, and $R_5$ represents OH.

Formula (13): $R_1$ represents $COCH_3$, $R_2$ represents NHAc, $R_3$ represents $OCH_3$, $R_4$ represents $COCH_3$, and $R_5$ represents

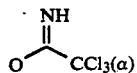

Formula (15): $R_1$ represents $COCH_3$, $R_2$ represents NHAc, $R_3$ represents $OCH_3$, $R_4$ represents $COCH_3$, and $R_5$ represents

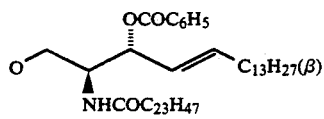

7. Ganglioside related compounds having a general formula (I):

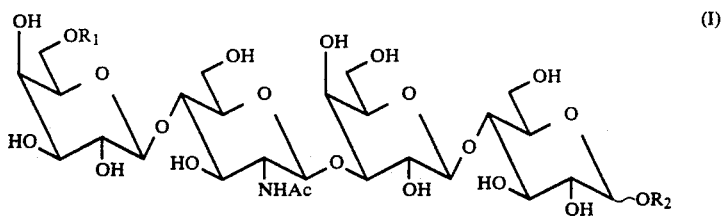

(wherein $R_1$ represents a hydrogen atom or

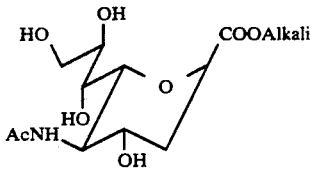

and $R_2$ represents a hydrogen atom or

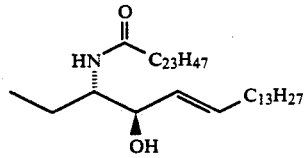

and Ac represents an acetyl group).

8. Method of producing the above ganglioside related compounds, comprising hydrolysing compounds having a general formula (II):

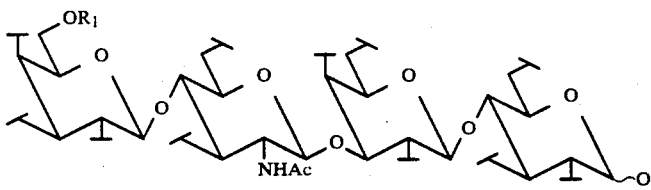

(wherein $R_1$ denotes a hydrogen atom or

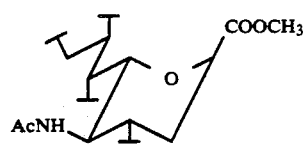

and $R_2$ denotes a hydrogen atom or

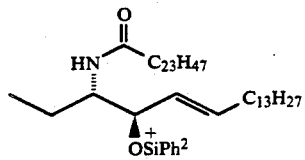

9. Ganglioside related compounds having a general formula:

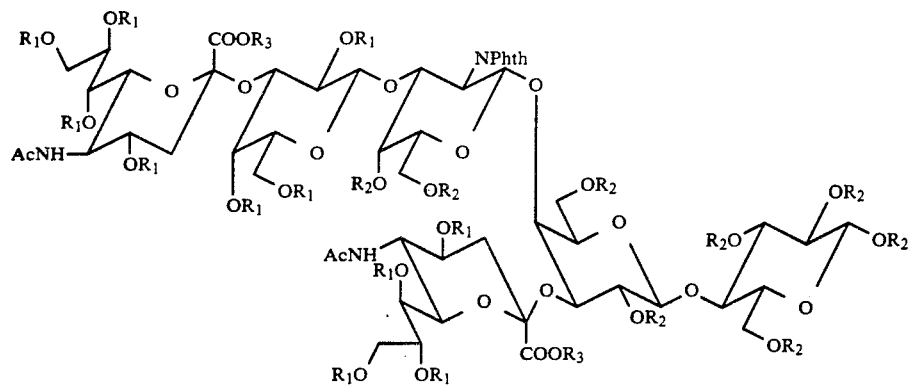
(I)
(wherein $R_1$ represents H or $COCH_3$; $R_2$, H or $C_6H_5CH_2$; $R_3$, H or $CH_3$; Ac, $COCH_3$; and NPhth,
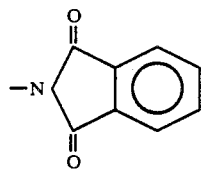
10. Method of producing compounds having the following formula:
by reacting compounds having the following formula:
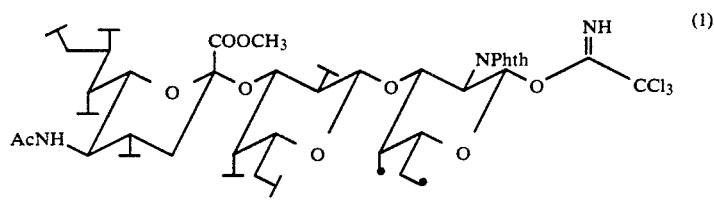
(1)
with compounds having the following formula:
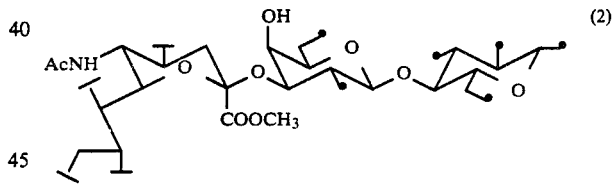
(2)
11. Another method of producing compounds having the following formula:
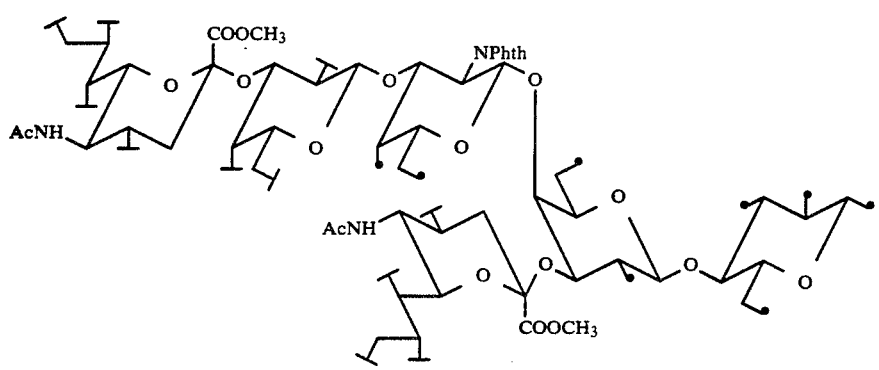
(3)

(4)

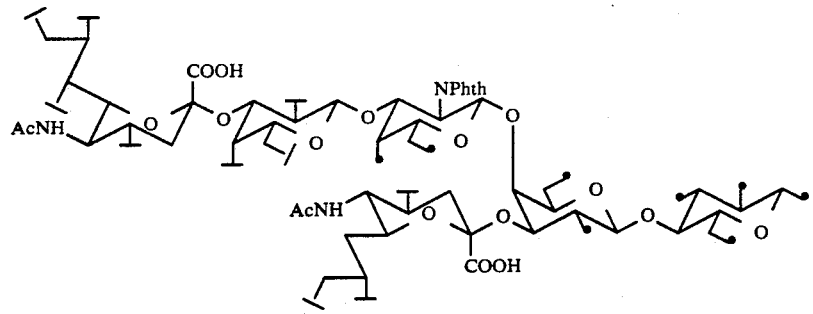

which method comprises demethylating compounds having the following formula:

(3)

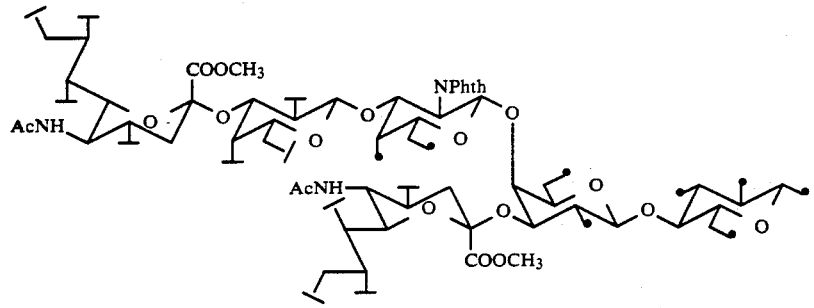

12. Still another method of producing compounds having the following formula:

(5)

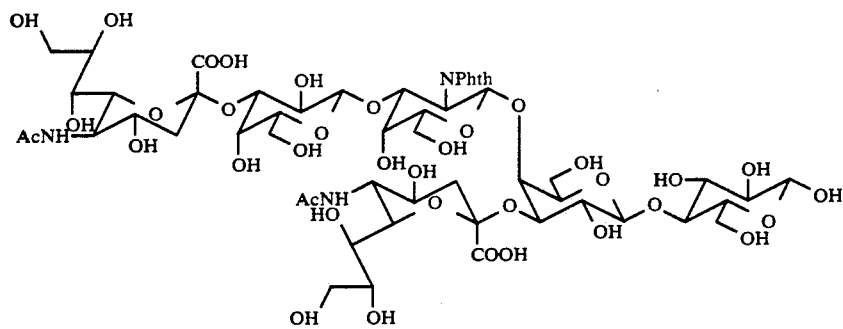

which method comprises hydrolysing and catalytically reducing compounds having the following formula:

(4)

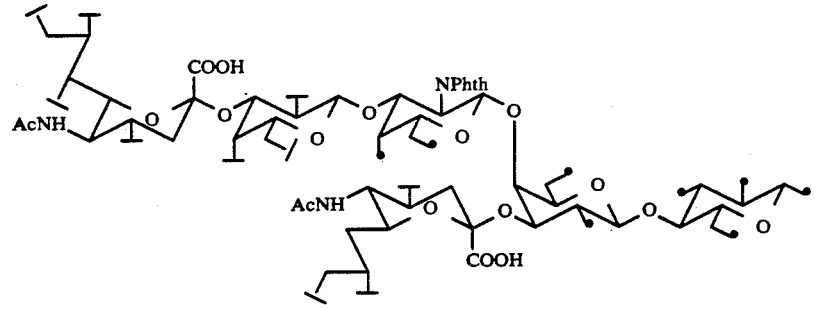

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE INVENTION

Figure 1:
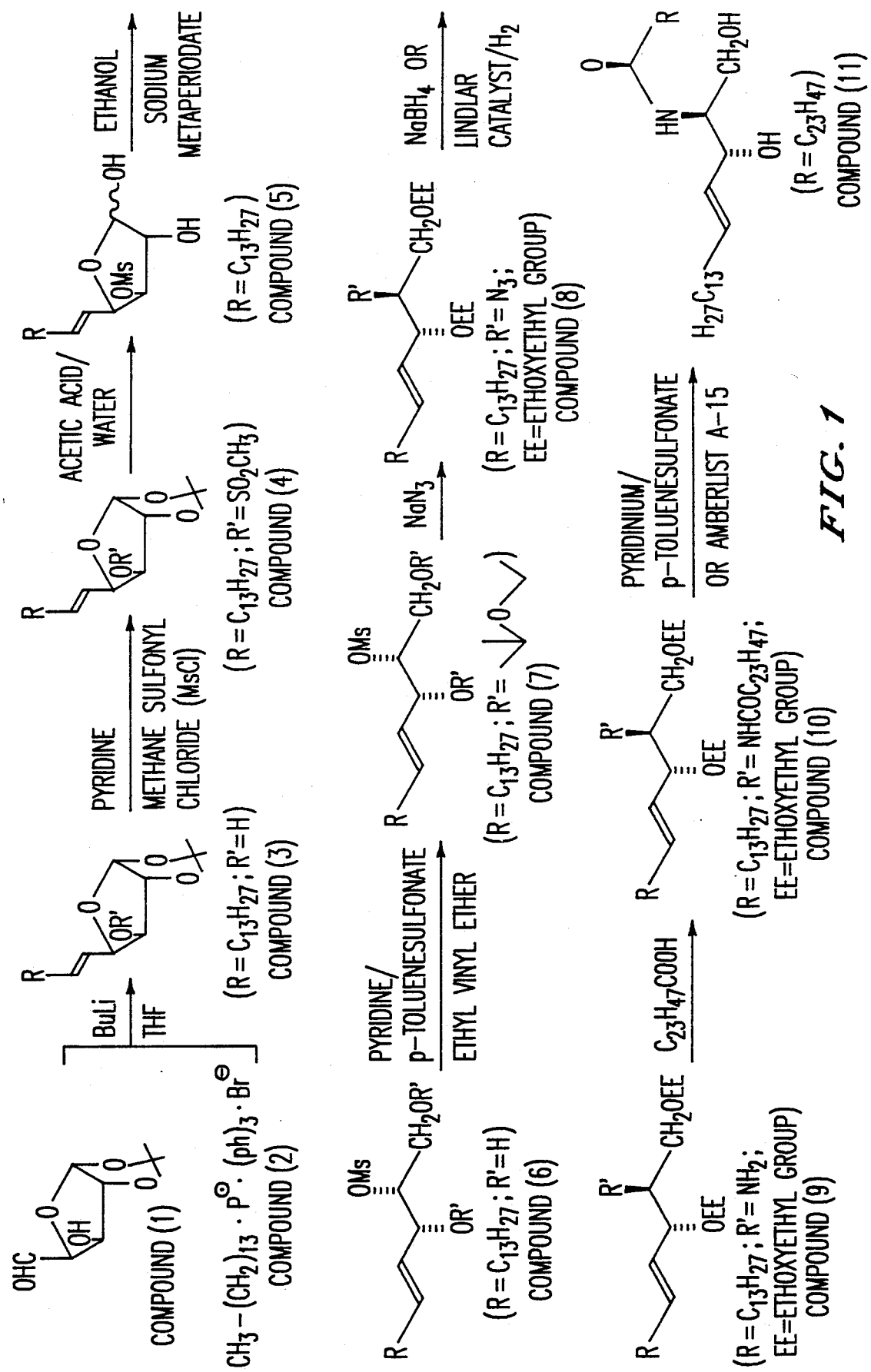
FIG. 1 illustrates a scheme for the synthesis of Compound (11)
Figure 2:
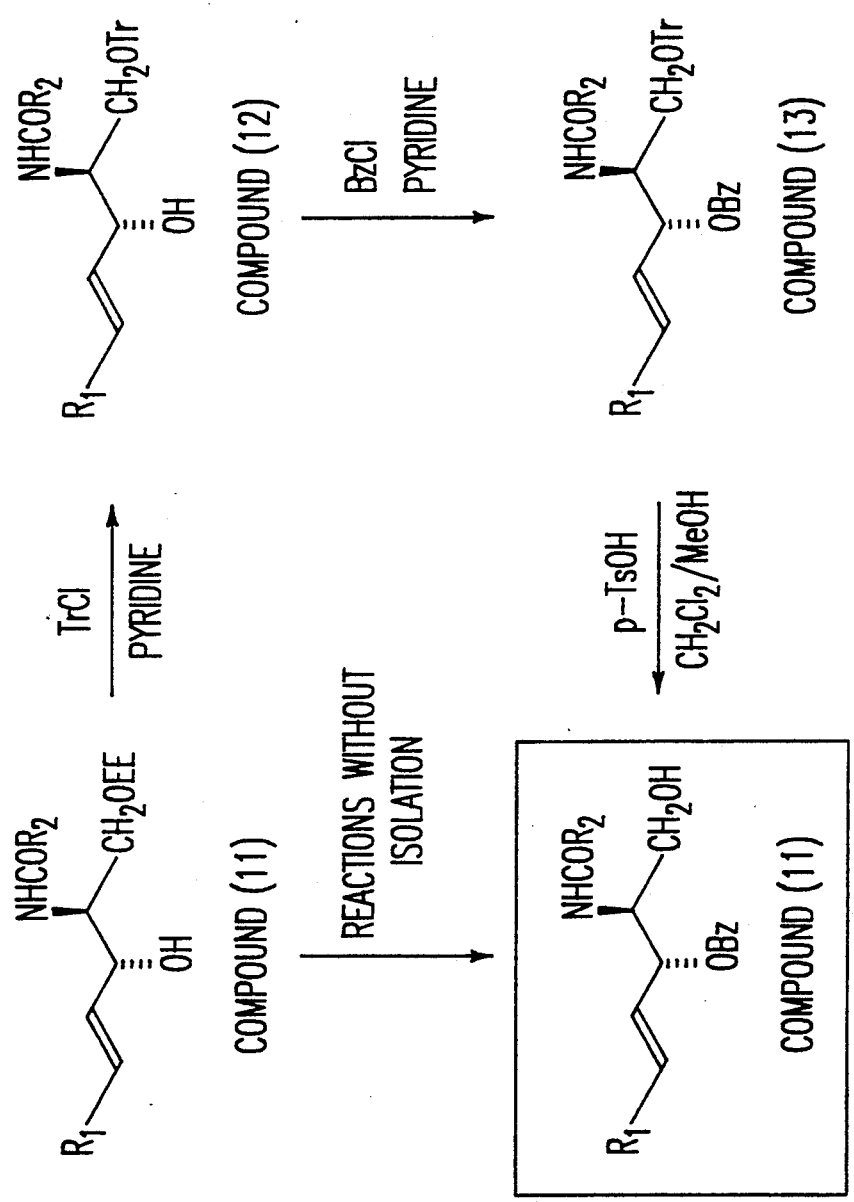
FIG. 2 illustrates a scheme for the synthesis of Compound (11)
Figure 3B:
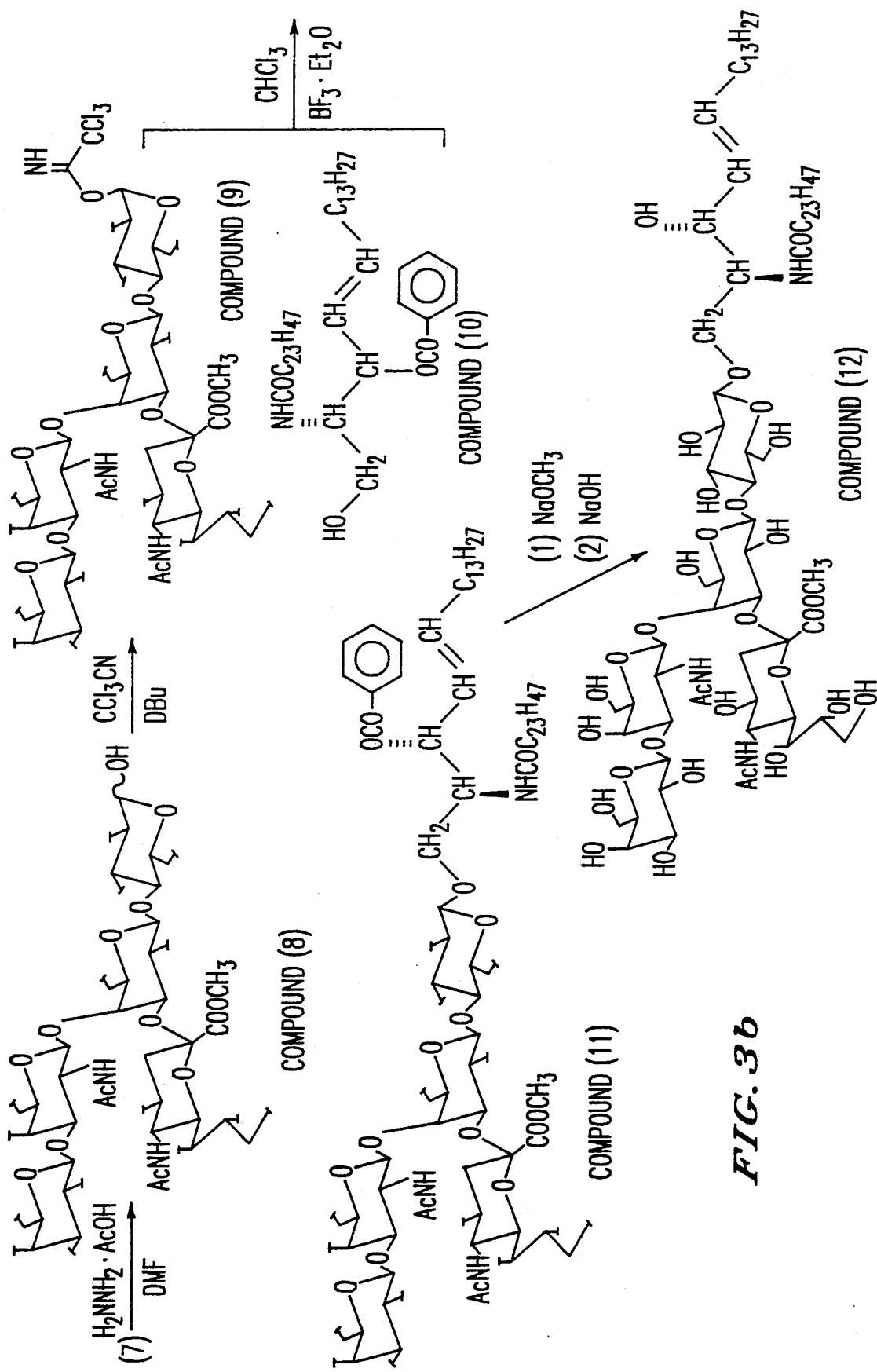
FIGS. 3a and b illustrate a scheme for the synthesis of Compound (12)
Figure 4A:
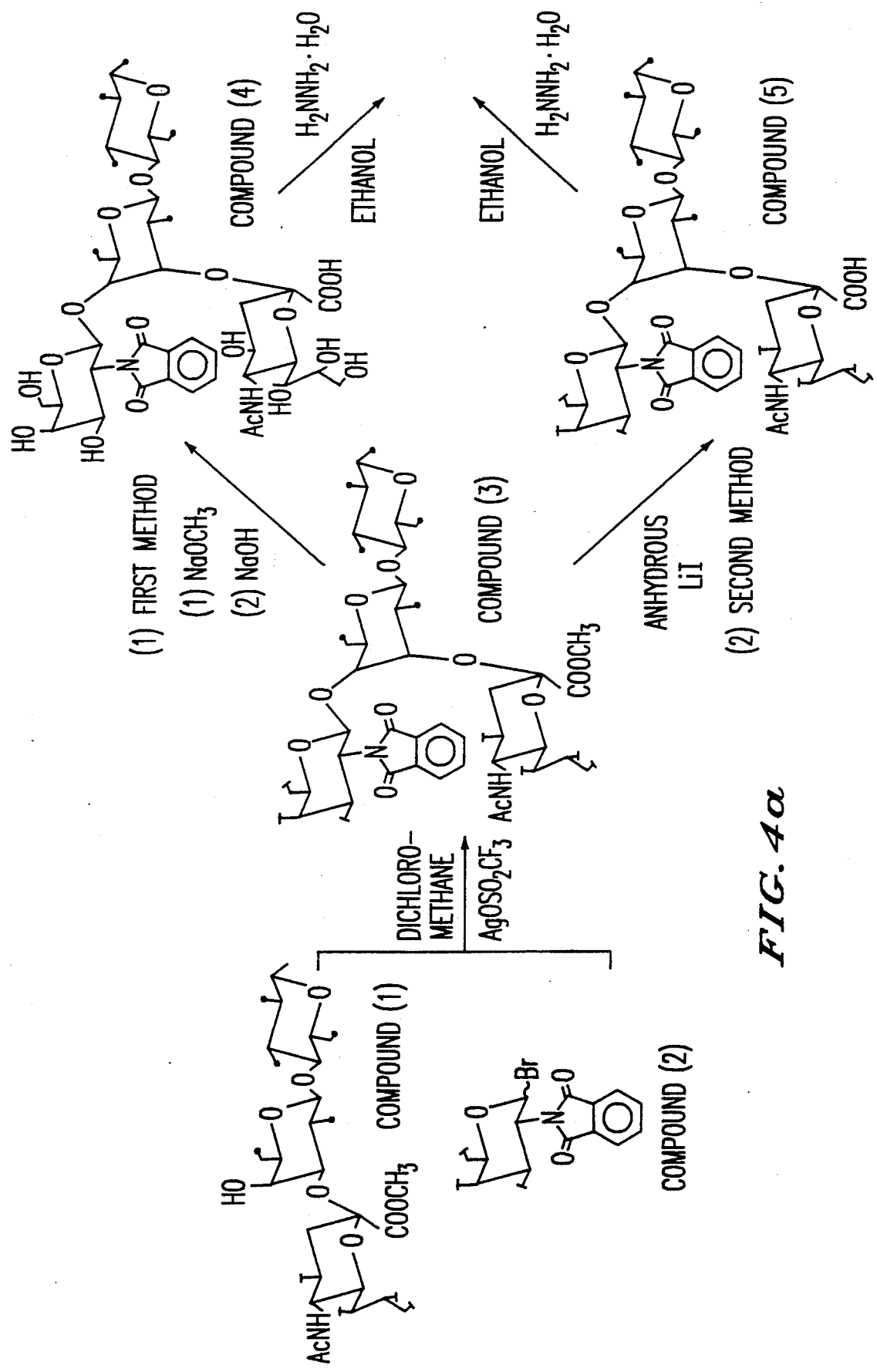
FIGS. 4a–e illustrate a scheme for the synthesis of Compound (16)
Figure 4B:
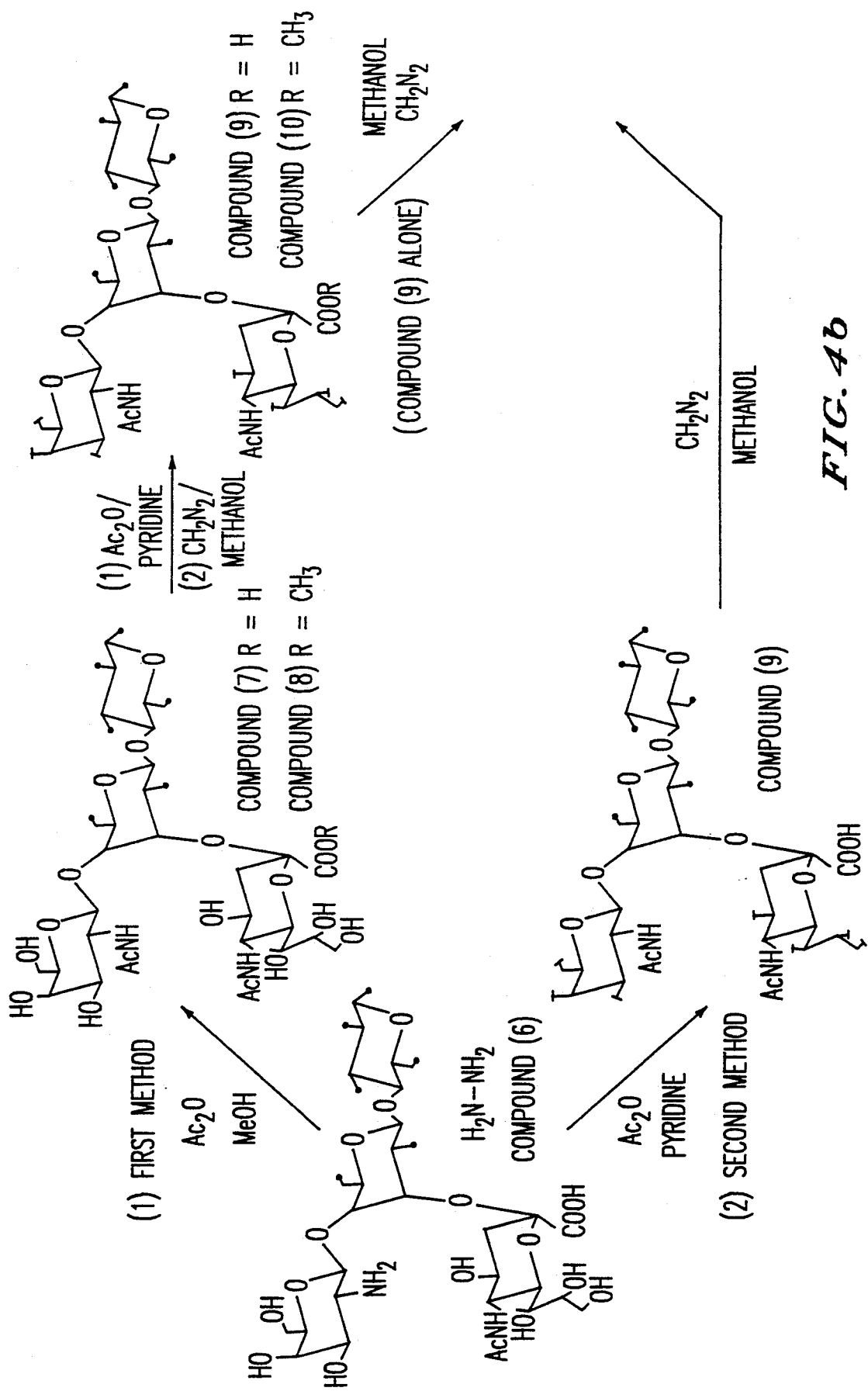
Figure 4C:
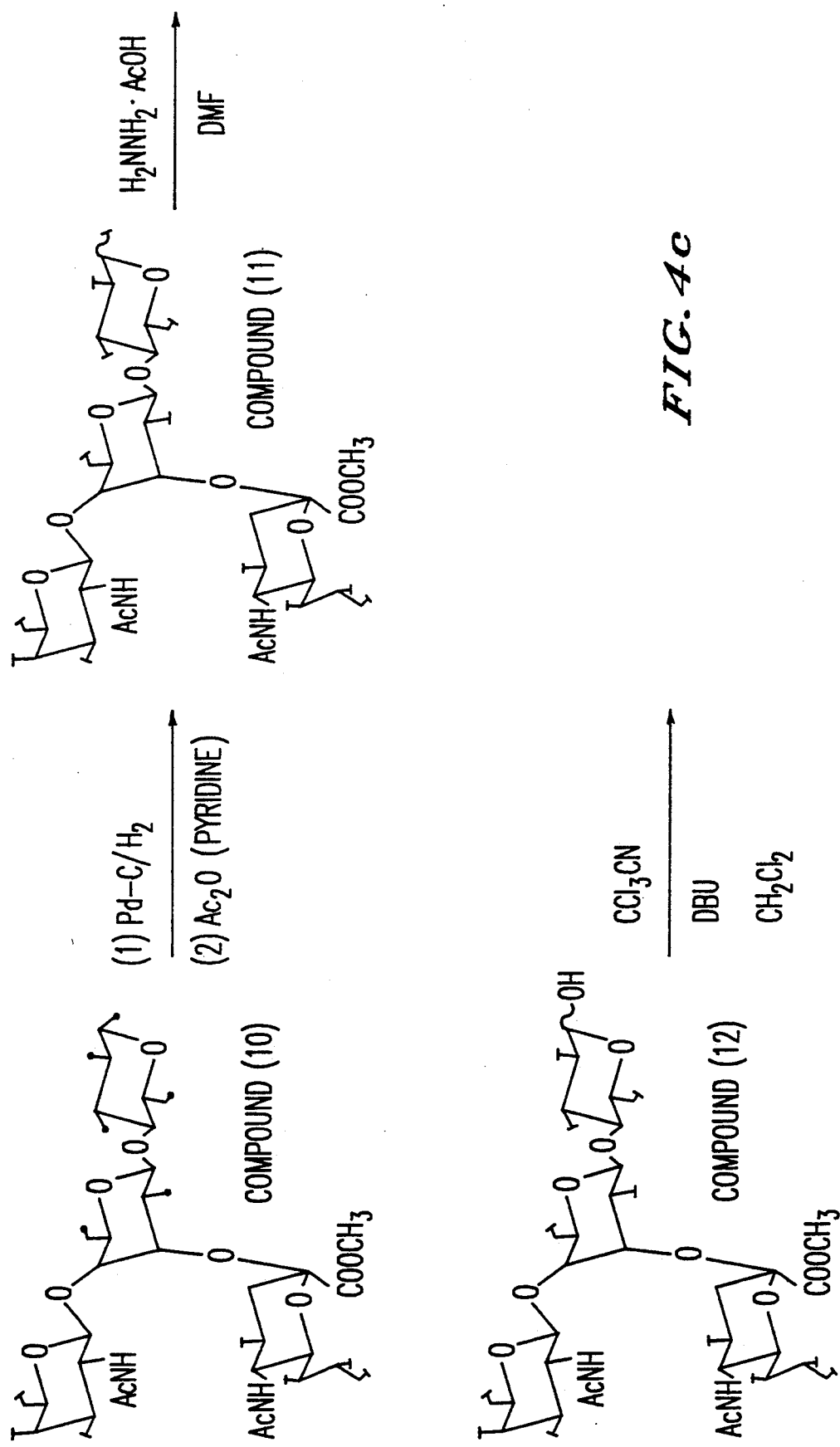
Figure 4D:
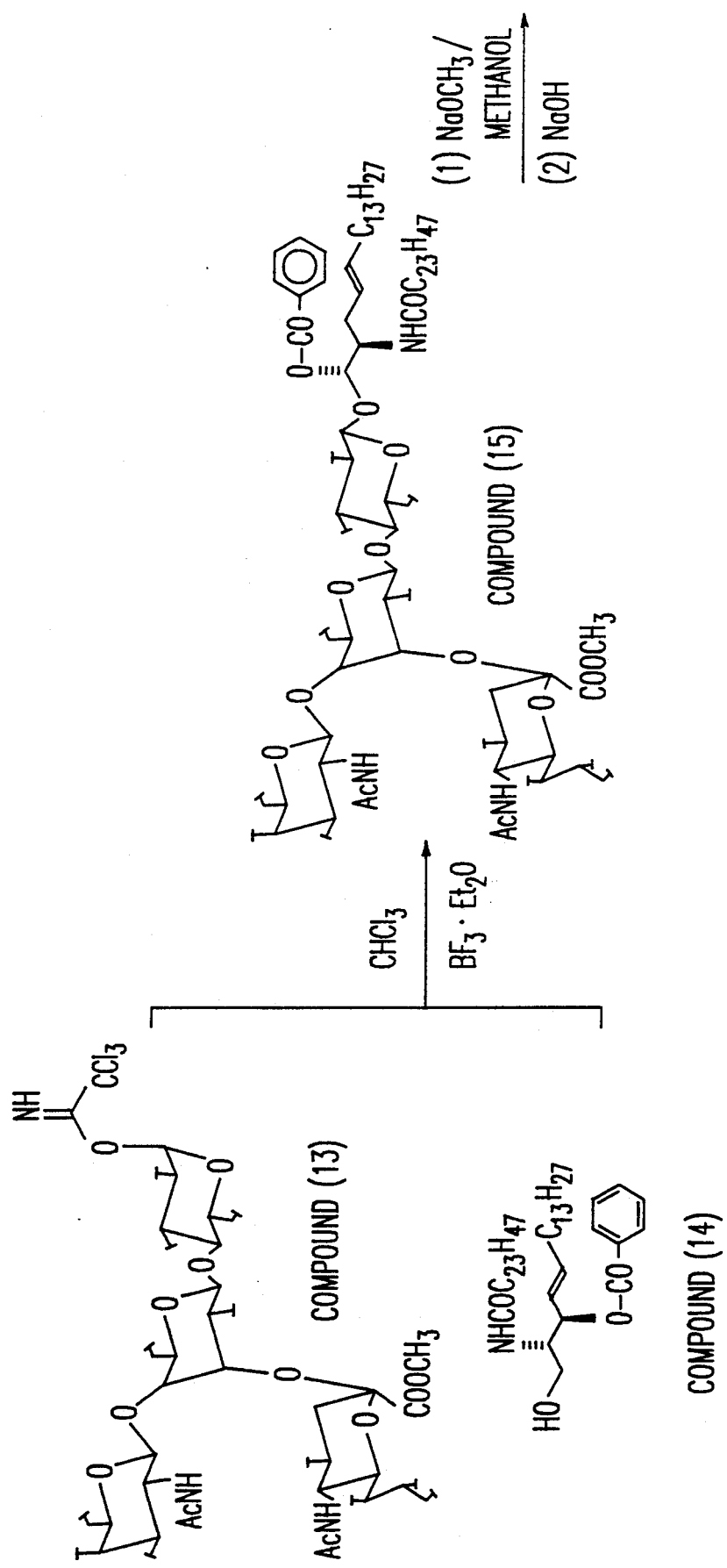
Figure 4E:
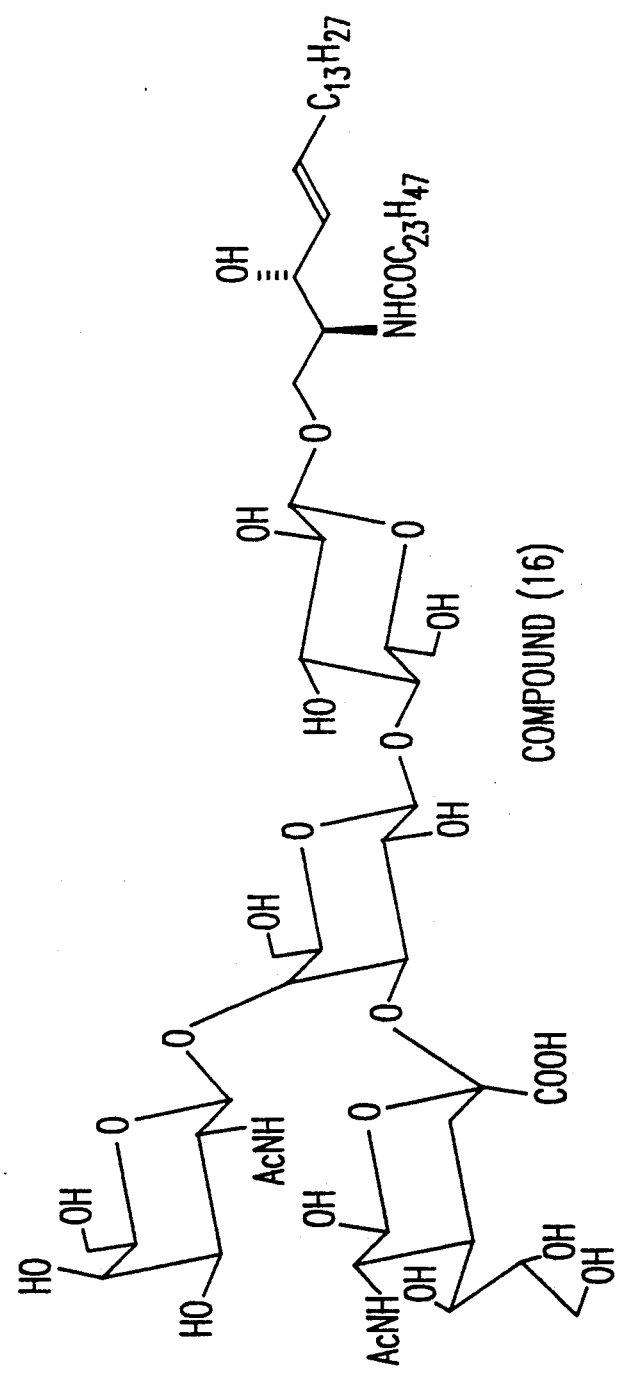
Figure 5A:
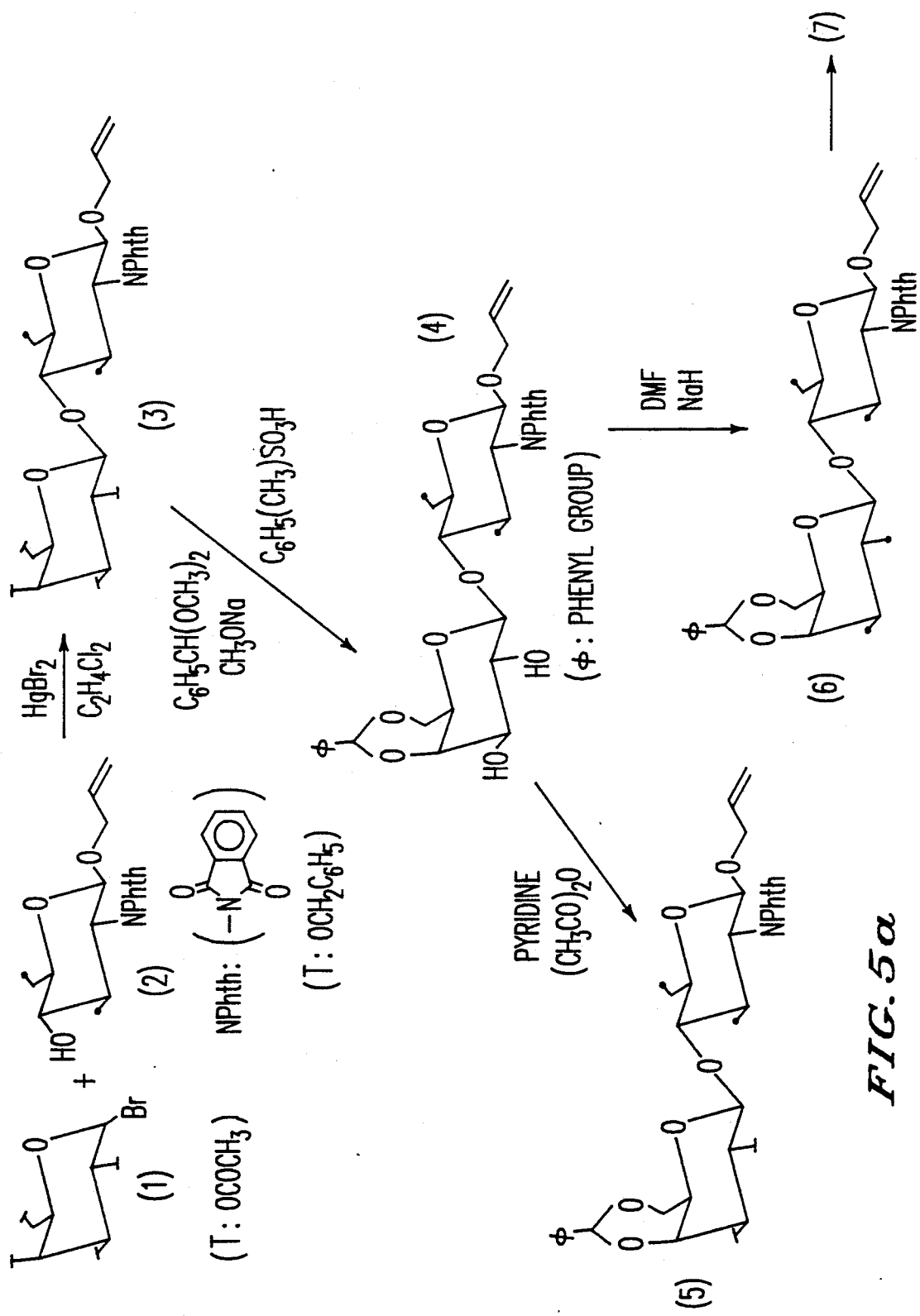
FIGS. 5a and b illustrate a scheme for the synthesis of Compound (9) and (10)
Figure 5B:
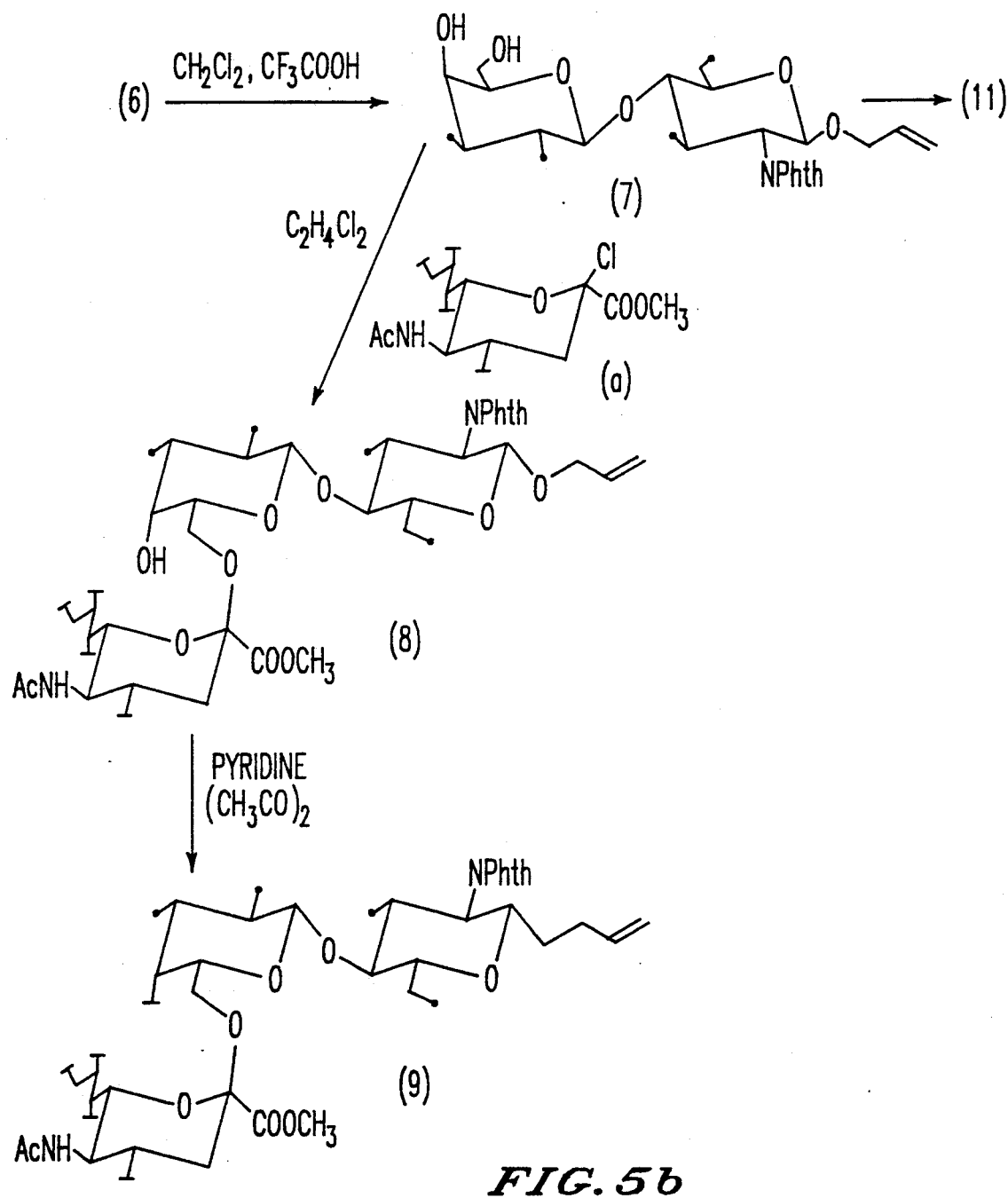
Figure 6A:
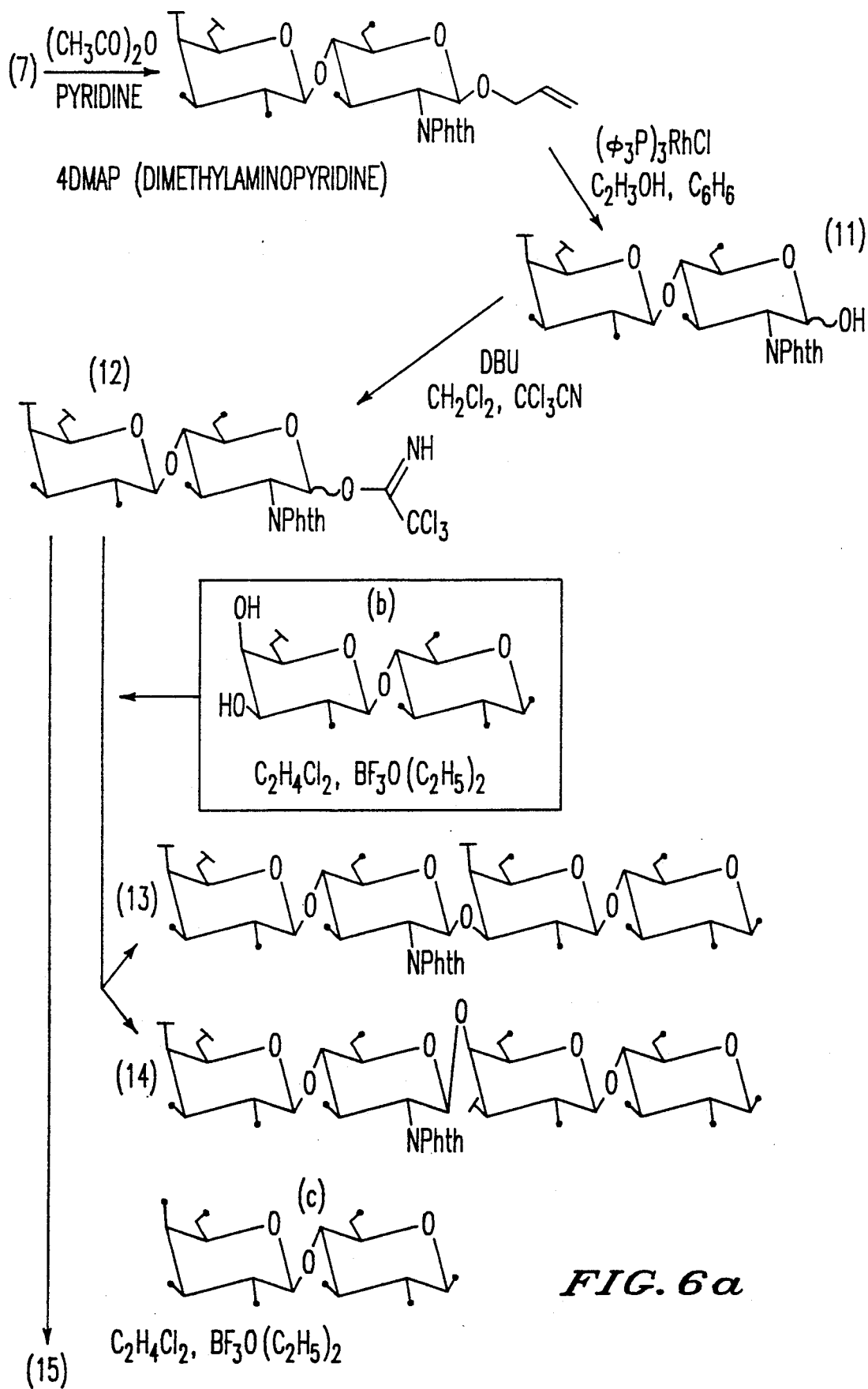
FIGS. 6a–c illustrate a scheme for the synthesis of an asialic ganglioside.
Figure 6B:
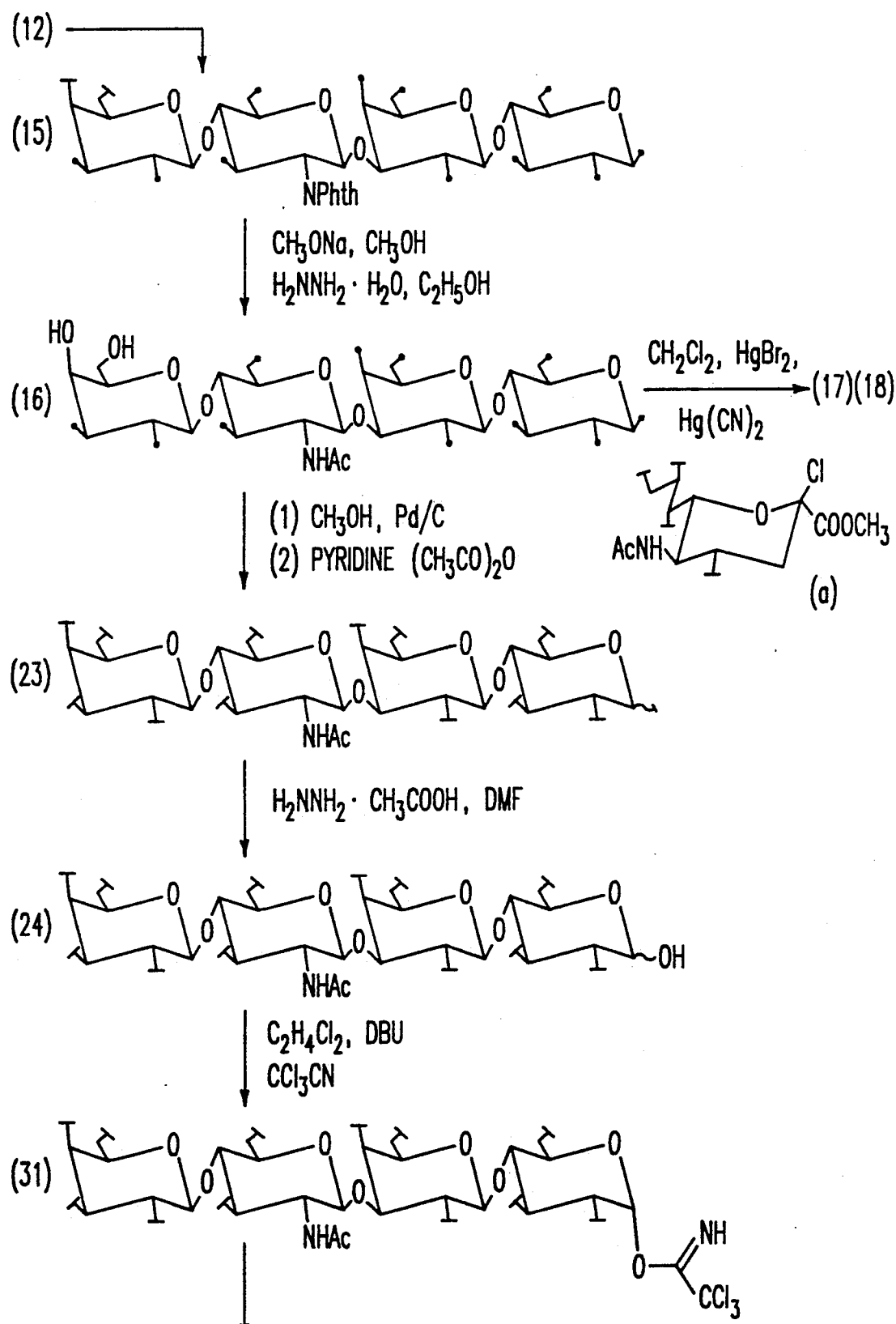
Figure 6C:
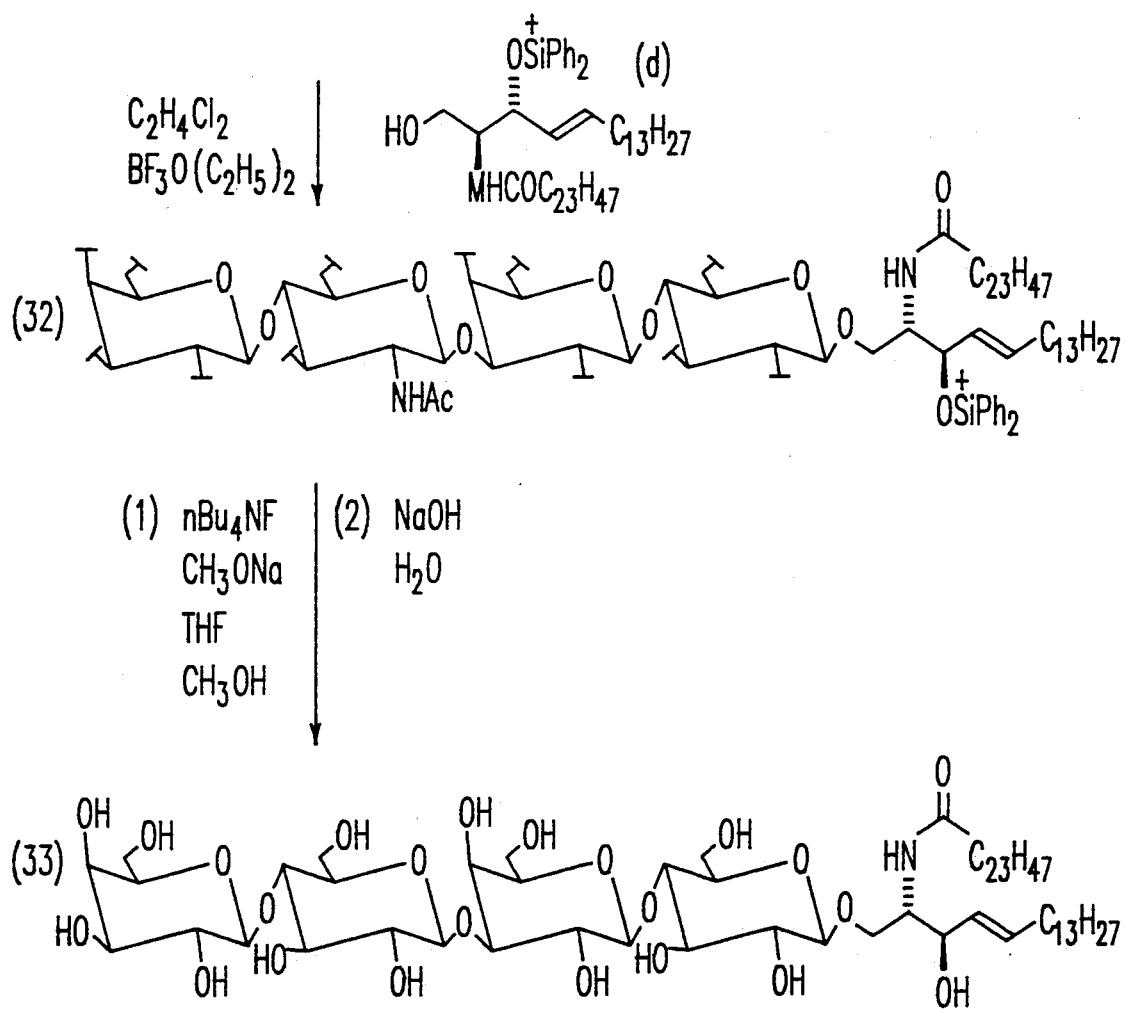
Figure 7A:
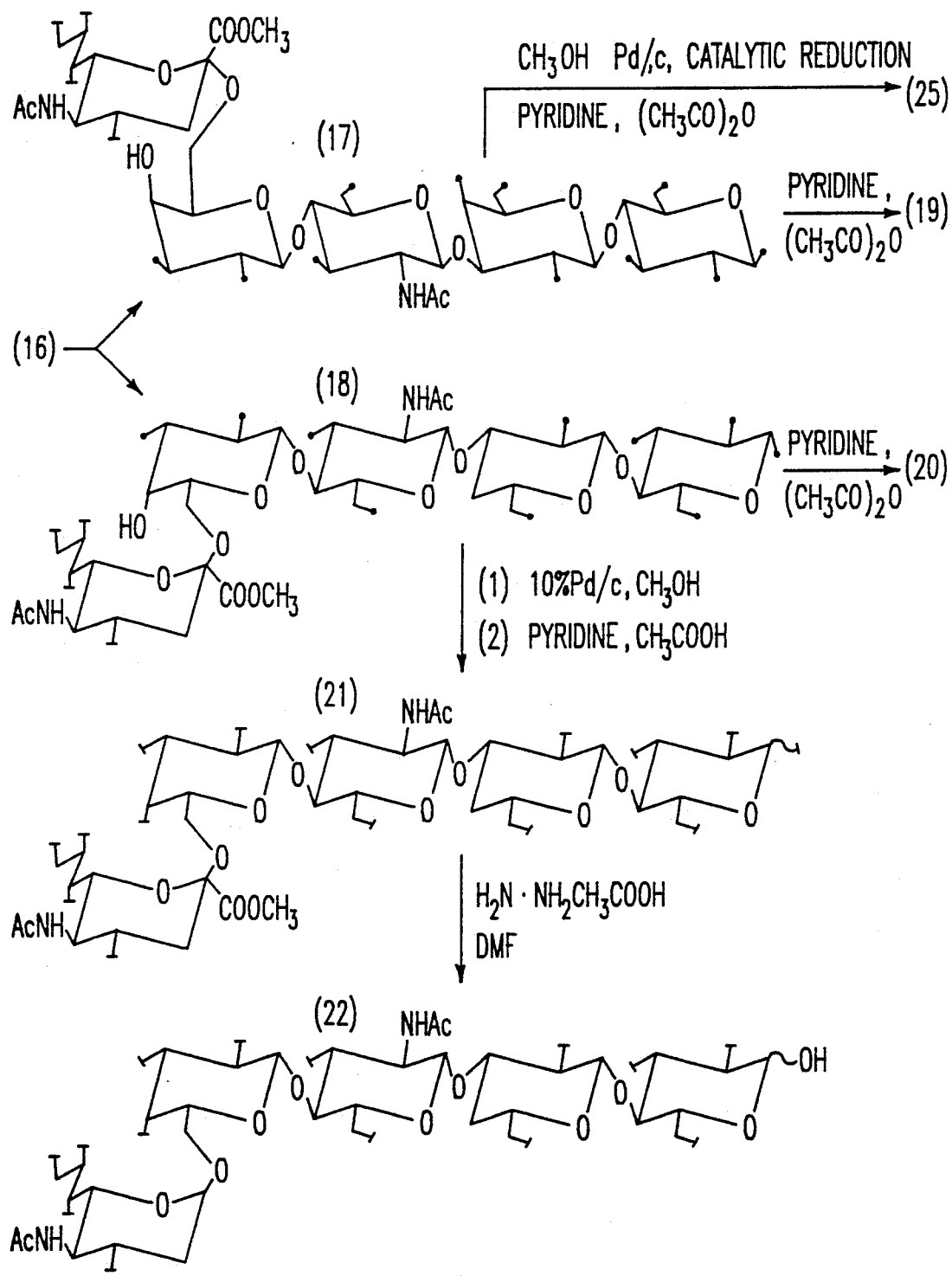
FIGS. 7a and b illustrate a scheme for the synthesis of Compound (20)
Figure 7B:
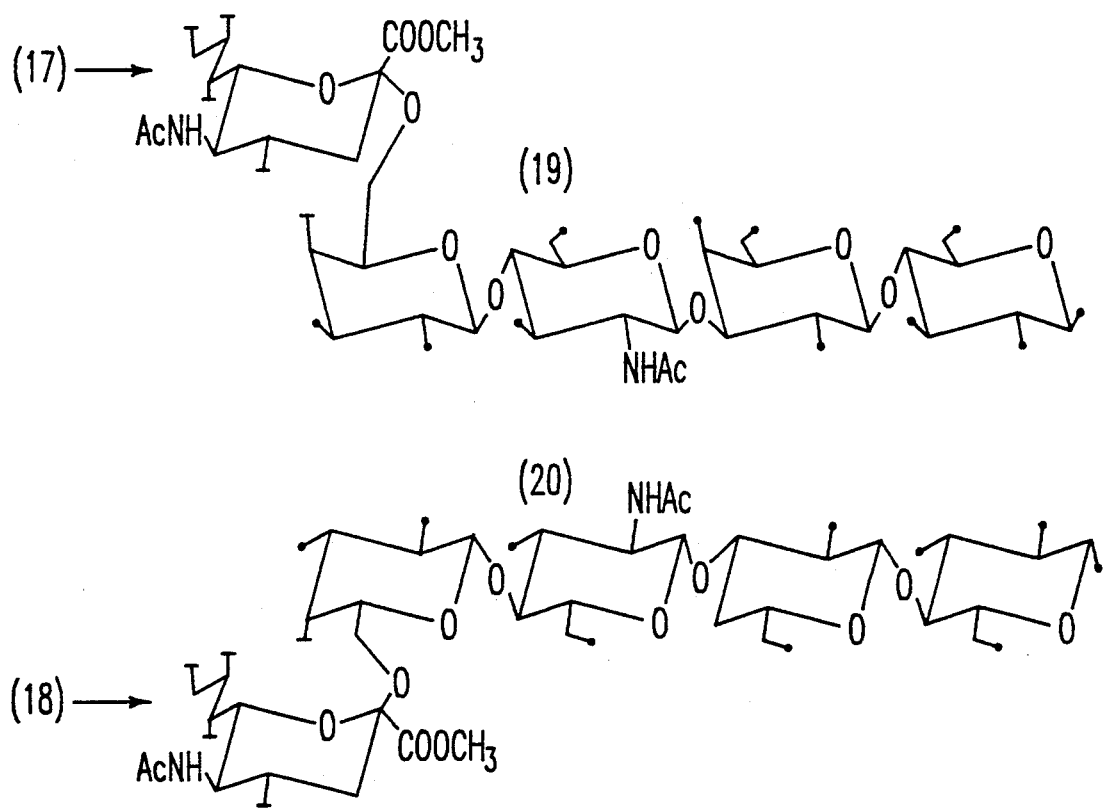
Figure 8A:
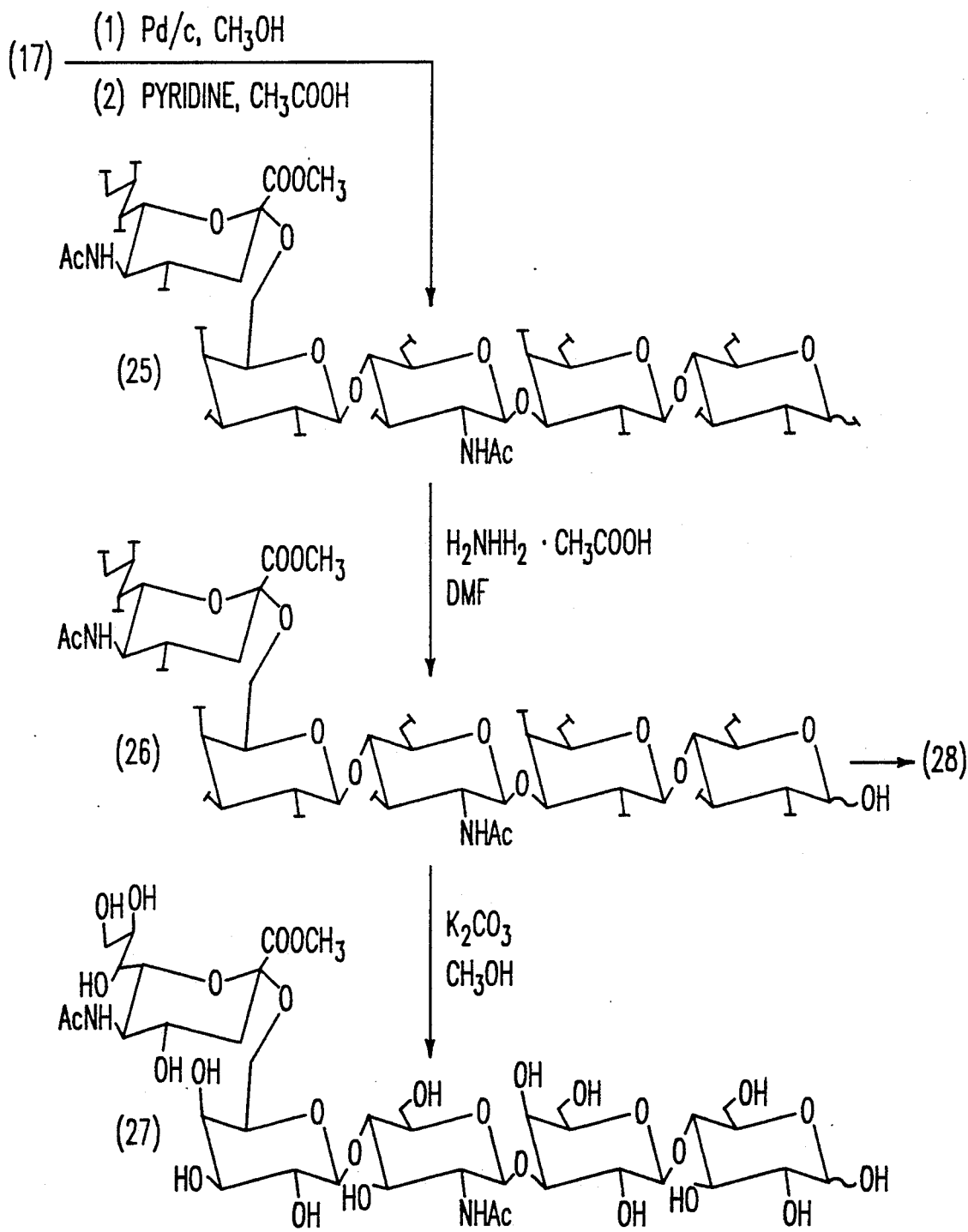
FIGS. 8a and b illustrate a scheme for the synthesis of Compound (30).
Figure 8B:
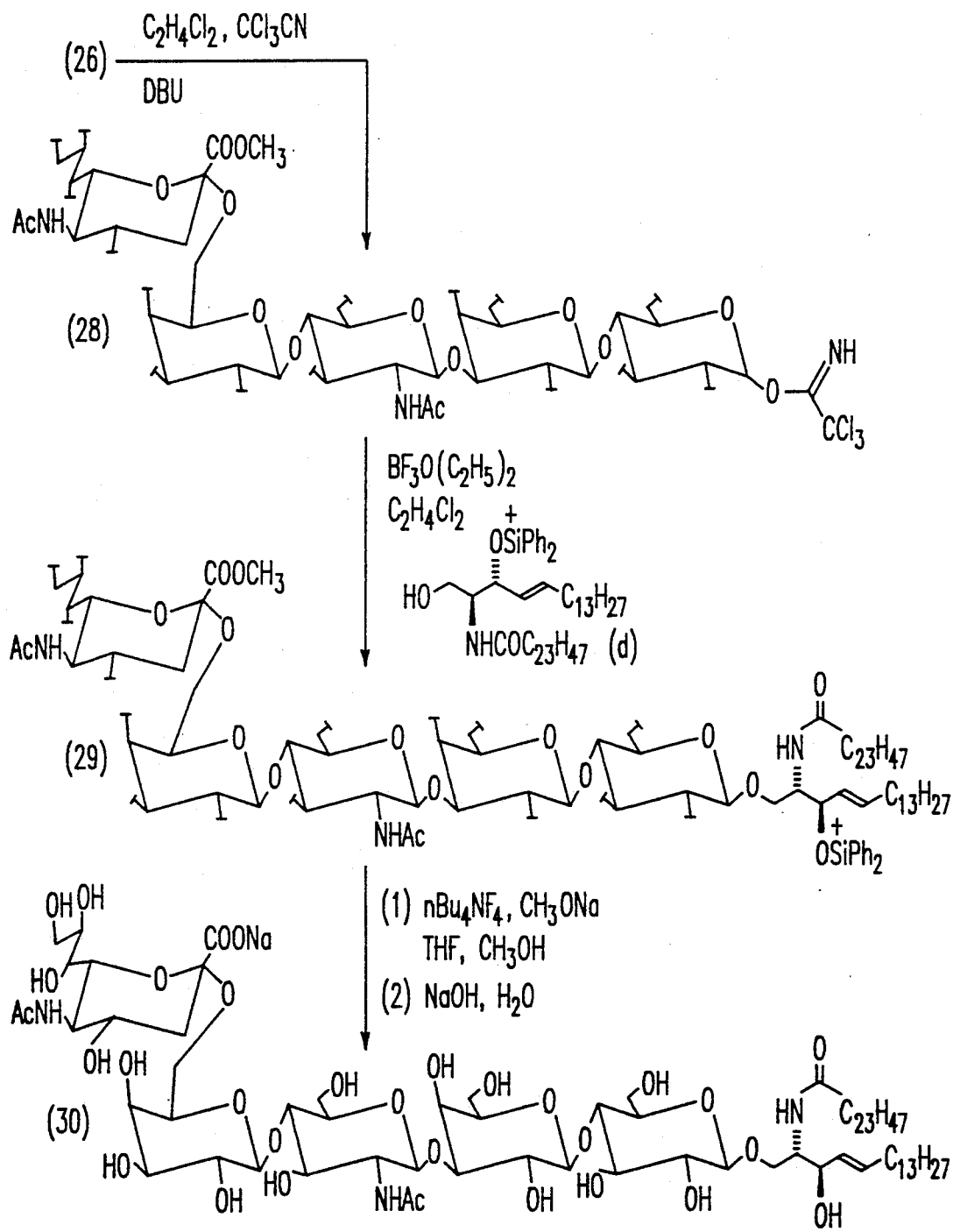

The present invention will be described in detail below.

(A) Production of Ganglioside $GM_1$ related compound having the following general formula:

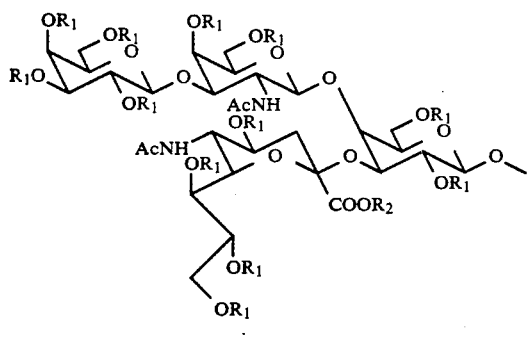

where $R_1$ represents H or $COCH_3$ (hereinafter abbreviated to "Ac"); $R_2$ represents H or $CH_3$; and $R_3$ represents either —OH,

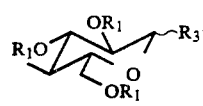

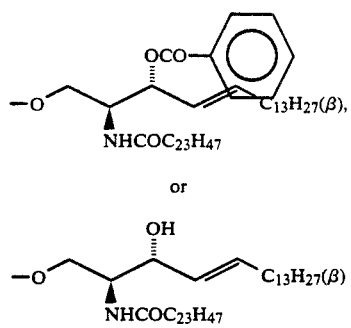

(1) Production of Compound (3) having the following general formula:

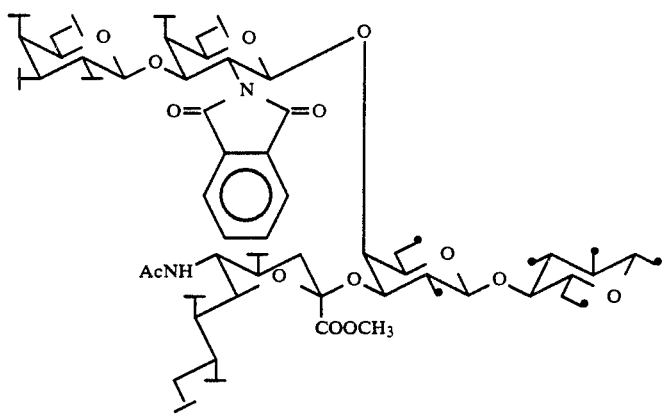

where

T represents $OCOCH_3$ and

ϒ represents $OCOC_6H_5$ (These symbols represent the same substances also in formulas described below.)

This compound (3) is obtained by reaction between Compound (1) expressed by the following formula:

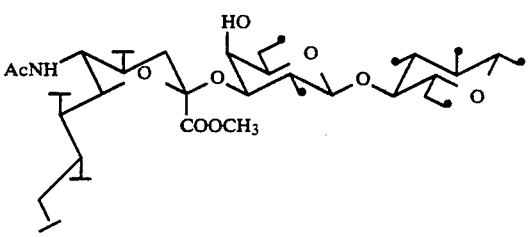

and Compound (2) expressed by the following formula:

(2) Production of Compound (4) expressed by the following formula:

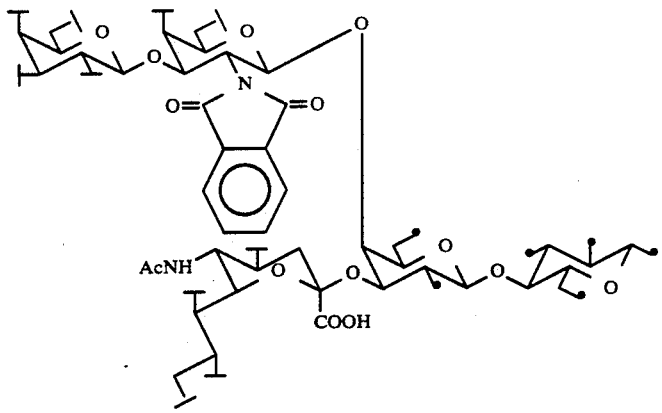

This compound (4) is obtained by treating the compound (3) in a pyridine-type solvent such as pyridine or collidine in the presence of a catalyst such as anhydrous lithium iodide, normally at a temperature of between about 60° C. and a reflex temperature. The treatment is normally effected for 1 to 15 hours. In order to maintain the anhydrous condition, the treatment may be carried out in an argon atmosphere.

(3) Production of Compound (5) expressed by the following formula:

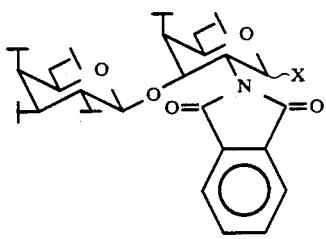

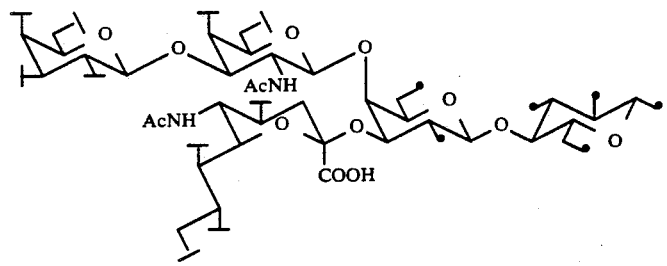

where X represents

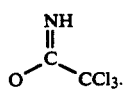

The compound (1) can be obtained by a method described in Can. J. Chem. 57, 1244 (1979).

The compound (2) can be obtained by a method described in Can. J. Chem. 62, 644–653 (1984).

The reaction between the compounds (1) and (2) is effected in a solvent in the presence of a catalyst, preferably at a temperature of between 0° and 30° C. Suitable examples of the solvent are dichloromethane, dichloroethane, tetrahydrofuran, nitromethane, and Lewis acids such as TMS Trifrate, $TiCl_4$, and $AlCl_3$. Suitable examples of the catalyst are $BF_3$—$Et_2O$ (borontrifluoride-ethylether complex), salts of silver and mercury such as $AgOSO_2CF_3$, $AgClO_4$, silver silicate, $HgBr_2$, and $Hg(CN)_2$.

The compound (5) can be produced by a two-step reaction.

In the first step, the compound (4) is treated in the presence of, for instance, hydrazine hydrate ($H_2NNH_2 \cdot H_2O$) at a temperature of between 60° C. and a reflux temperature, thereby changing the pythalidmide group of the compound (4) to an amino group. In this first step, the treatment may alternatively be effected by using, in place of hydrazine hydrate, an alkyl amine such as $CH_3NH_2$ or $CH_3CH_2CH_2CH_2NH_2$, or an alcohol such as methanol or ethanol, and using a temperature of between room temperature and a reflux temperature. The treatment period is normally 1 to 10 hours.

In the second step, the amine compound obtained in the first step is treated with acetic anhydride, in pyridine at a temperature between room temperature and 60° C. This treatment is normally effected for 24 hours.

By these two steps, the phthalimide group of the compound (4) is changed to an acetamide group.

(4) Production of Compound (6) expressed by the following formula:

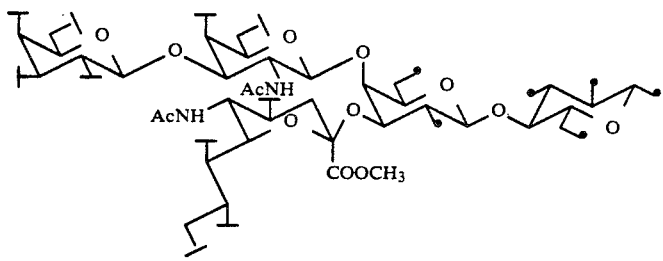

This compound (6) is obtained by reacting diazomethane ($CH_2N_2$) with the compound (5) in methanol at a temperature of between 0° C. and room temperature. By this reaction, the carboxyl group of the compound (5) is changed to a methyl ester group. The reaction period is for instance, relatively short such as 30 minutes.

(5) Production of Compound (7) expressed by the following formula:

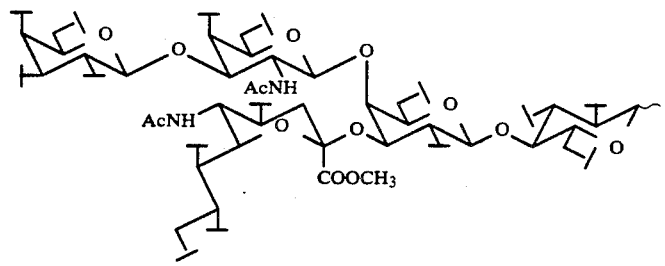

This compound (7) is obtained by the following two steps.

In the first step, Pd-C is added to the compound (6) in a suitable solvent such as methanol at a temperature near room temperature, thereby catalytically reducing the compound so that it becomes a debenzoylated compound. The reaction is normally effected for 24 hours.

In the second step, acetic anhydride is reacted with the intermediate product which has been obtained in the first step, in pyridine at a temperature of between 0° and 30° C., thereby acetylating the intermediate product so that it becomes a peracetate (the compound (7)). This reaction is also effected for 24 hours normally.

(6) Production of Compound (8) expressed by the following formula:

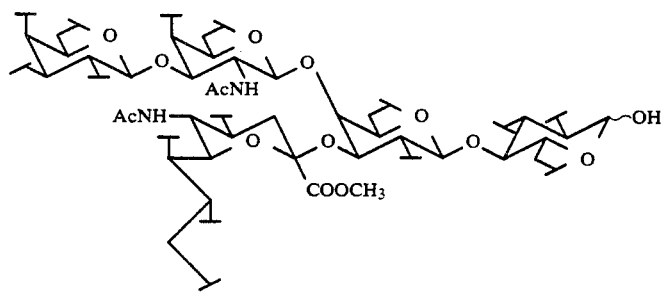

This compound (8) is obtained by treating the compound (7) hydrazinium acetate ($H_2NNH_2AcOH$) in a solvent such as dimethylformamide (DMF), thereby acetylating the hydroxyl group of the compound (7). The reaction is normally effected at a temperature of between room temperature and 50° C.

(7) Production of Compound (9) expressed by the following formula:

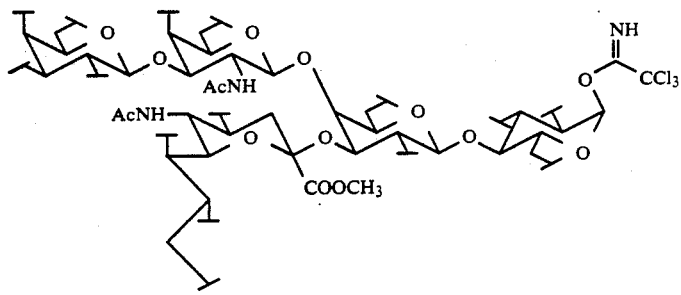

This compound (9) is obtained by reacting the compound (8) with trichloroacetonitrile in a solvent such as methylene chloride, normally at a temperature of between 0° and 40° C., and in the presence of either 1,8-diazabicyclo (5,4,0) undeca-7-ene (DBU) or NaH. The reaction period is normally 1 to 10 hours.

(8) Production of Compound (11) expressed by the following formula:

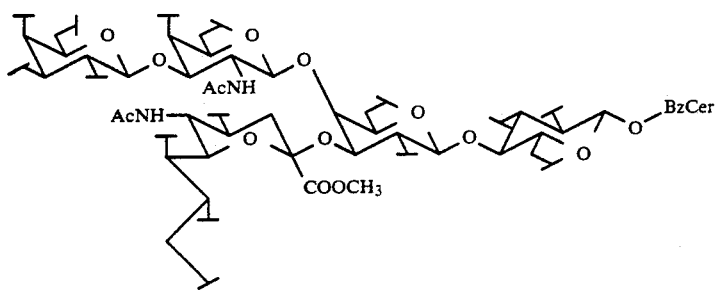

where BzCer represents

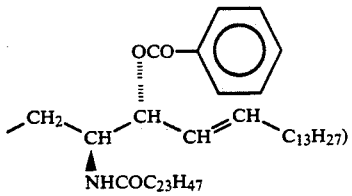

This compound (11) is obtained by reacting a ceramide compound (10) expressed by the following formula:

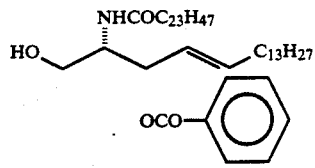

with the compound (9) in a solvent such as CHCl$_3$, in the presence of a glicosidation catalyst such as BF$_3$—Et$_2$O or a Lewis acid catalyst such as SnCl$_4$, AlCl$_3$, TiCl$_4$, TMS Trifrate, in an atmosphere of an inert gs such as argon. The temperature is preferably between 0° to 30° C. The reaction period is normally 2 to 30 hours.

The ceramide compound (10) to be used can be synthesized by a method shown in Scheme I.

When Compound (1) is reacted with Compound (2) in a solvent such as THF or hexane in the presence of BuLi, a 4-alkyl vinyl compound (Compound (3)) is obtained A reaction temperature of between −15° to 25° C. and a reaction period of 0.5 to 24 hours are suitable.

The compound (2) used in this process can be obtained by refluxing an alkyl halide such as 1-bromotetradecane and triphenyl phosphine in a solvent such as xylene for one night.

The compound (3) is then treated with methane sulfonyl chloride in dry pyridine so as to obtain a 3-methane sulfonyl compound (Compound (4)). A reaction temperature of between 0° to 25° C. and a reaction period of between 2 to 24 hours are suitable.

Subsequently, the compound (4) is treated in acetic acid/water, thereby eliminating the iso-propylidene group so that a diol compound (Compound (5)) is obtained. A reaction temperature of between 70° and 90° C. and a reaction period of between 0.5 and 5 hours are suitable.

The compound (5) is then subjected to the following treatment. It is first treated with an oxidizing agent such as sodium metaperiodate in a solvent such as ethanol, thereby cleaving the diol portion of the compound and then treated with a reducing agent such as sodium boron hydroxide, thereby obtaining a diol compound (compound (6). In the oxidation step, a temperature of between 0° and 25° C. and a period of 0.5 to 24 hours are suitable. In the reduction step, a temperature of between 0° and 10° C. and a period of 0.5 to 2 hours are suitable.

The compound (6) is then reacted with an alkyl vinyl ether such as ethyl vinyl ether in a solvent such as dichloromethane in the presence of a catalyst such as pyridinium p-toluenesulfonate, thereby obtaining dialkyl vinyl ether compound (Compound (7)). A reaction temperature of between 0° to 30° C. and a reaction period of 0.5 to 24 hours are suitable.

The compound (7) is then treated with an azide such as sodium azide in a solvent such as DMF, thereby obtaining an azide (Compound (8)). A reaction temperature of between 70° to 120° C. and a reaction period of one night to 6 days are suitable.

The azide (8) (Compound (8)) is reduced by a reducing agent such as sodium boron hydroxide or Lindlar catalyst/H₂ in a solvent such as ethanol or isopropanol, thereby obtaining an amine (Compound (9)). When sodium boron hydroxide is used, a reaction temperature equal to the reflux temperature and a reaction period of 1 to 6 days are suitable. When Lindlar catalyst/H₂ is used, a reaction temperature of between 0° and 30° C., a reaction period of 2 to 24 hours, and a hydrogen pressure of between 1 to 4 atoms are suitable.

The thus obtained amine (Compound (9)) is reacted with acyl halide in the presence of a substance such as pyridine or dimethylaminopyridine, thereby obtaining an amide (Compound (10)). A reaction temperature of between 0° to 30° C. and a reaction period of 0.5 to 24 hours are suitable. Alternatively, the amide (Compound (10)) may be obtained by dissolving the amine (Compound (9)) in a substance such as dichloromethane and reacting it with a fatting acid in the presence of a substance such as 2-chloro-1-methylpyridinium iodide or tri-n-butylamine.

This reaction adequately proceeds if it is effected in an inert gas flow such as an argon flow at a temperature equal to the reflux temperature for a period of 0.5 to 13 hours.

The amide (compound (10)) is then treated with a substance such as pyridinium p-toluenesulfonate or Amberlist A-15 in a solvent such as methanol or dichloromethane, thereby eliminating the protective group. In this way, Compound (11), which is a starting material for the desired ceramide compound (10), is obtained.

As shown in Scheme II, the thus obtained compound (11) is then treated with trityl chloride in pyridine so that it becomes a tritylated compound (12). Thereafter, it is treated with benzoyl chloride, and dimethylaminopyridine so that it becomes a trityl-benzoyl compound (13). This compound is treated with para-toluenesulfonic acid so as to eliminate the trityl group, and produce a benzoyl compound (Compound (11)). The reactions may be performed in such a manner that the compounds (12) and (13) are not isolated.

(9) Production of Compound (12) expressed by the following formula:

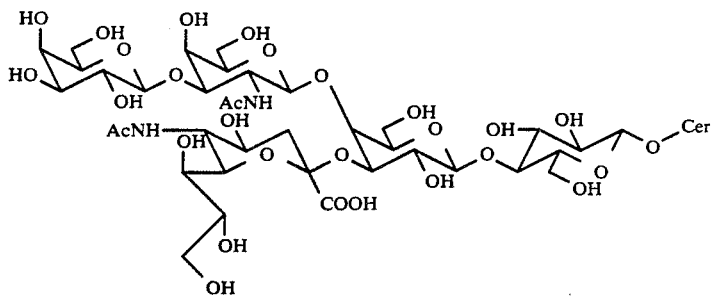

wherein Cer represents

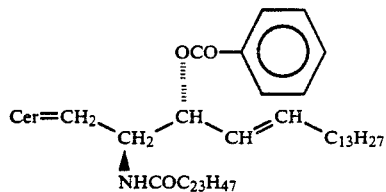

This compound (12) (Ganglioside GM₁) is obtained by first eliminating the acetyl group and the benzoyl group of the compound (11) by using, for instance, MeONa/MeOH as in a normal method, then neutralizing the resulting compound by a cation-exchanger such as Amberlist 15.

For reference, Compound (13) expressed by the following formula (13):

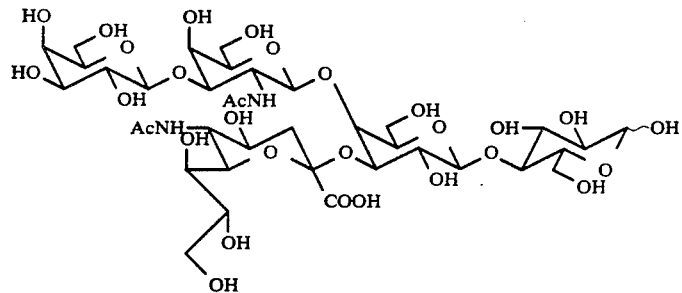

is obtained by a method comprising (a) treating the compound (6) with a substance such as NaOCH₃ in a solvent such as methanol at a temperature of between 0° C. and room temperature, (b) treating it with NaOH at a temperature of between 0° C. and room temperature, and (c) reducing it with Pd-C/H₂ at a temperature near room temperature.

An example of a method of producing Ganglioside GM₁ related compound in accordance with the present invention is shown in Scheme III.

The above compounds (7), (8), (9), (10), and (12) are novel compounds.

Utility

These compounds are useful as glycolipids which act as membrane receptors and also have activities for controlling functions and cell growth, and for promotion of neuron growth. Thus, they can be used as reagents in basic biology and can be used in clinical chemistry.

(B) Production of Ganglioside GM₂ related compound having the following general formula:

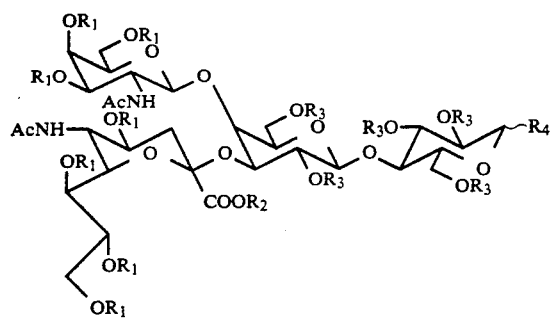

where,

① $R_1$ represents $COCH_3$, $R_2$ represents H or $CH_3$, $R_3$ represents $CH_2-C_6H_5$, and $R_4$ represents $OCH_2C_6H_5(\beta)$;

② $R_1$ represents $COCH_3$, $R_2$ represents $CH_3$, $R_3$ represents $COCH_3$, and $R_4$ represents $OCOCH_3$;

③ $R_1$ represents $COCH_3$, $R_2$ represents $CH_3$, $R_3$ represents $COCH_3$, and $R_4$ represents OH;

④ $R_1$ represents $COCH_3$, $R_2$ represents $CH_3$, $R_3$ represents $COCH_3$, and $R_4$ represents

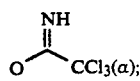

⑤ $R_1$ represents $COCH_3$, $R_2$ represents $CH_3$, $R_3$ represents $COCH_3$, and $R_4$ represents

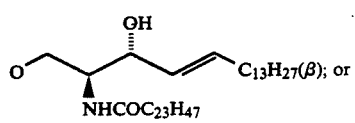

⑥ $R_1=R_2=R_3$ and they represent H, and $R_4$ represents

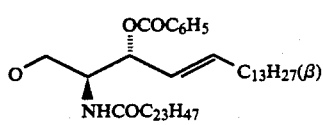

(1) Production of Compound (3) expressed by the following formula:

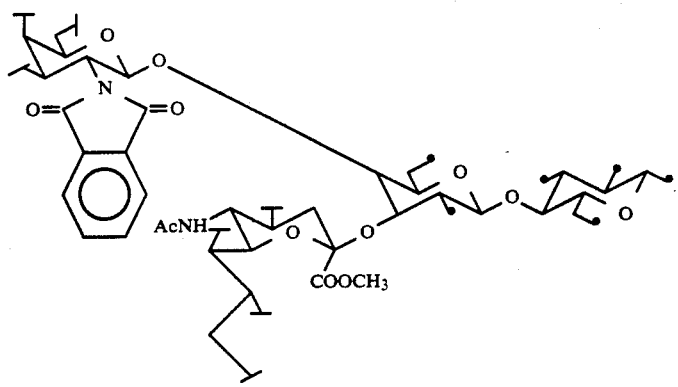

where

T represents $OCOCH_3$ and

↑ represents $OCH_2C_6H_5$ (These symbols represent the same groups also in formulae described below.)

This compound (3) is obtained by reacting Compound (1) expressed by the following formula:

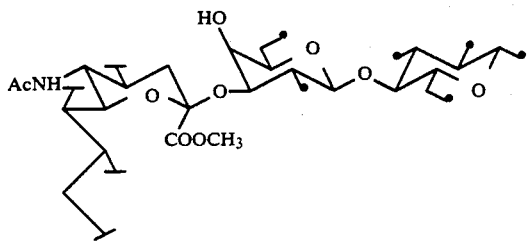

with Compound (2) expressed by the following formula:

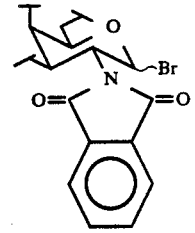

These compounds (1) and (2) can be obtained by a method described in Can. J. Chem. 57, 1244 (1979).

The reaction between the compounds (1) and (2) is effected in a solvent in the presence of a catalyst, preferably, at a temperature of between −10° and 30° C. Suitable examples of the solvent are dichloroethane, dichloromethane, nitromethane, and THF. Suitable examples of the catalyst are silver salts such as silver Trifrate (AgOSO₂CF₃), AgClO₄, Ag₂CO₃, and silver silicate, and salts of mercury such as Hg(CN)₂ and HgBr₂. The reaction is normally effected or 24 hours.

(2) Production of Compound (6) expressed by the following formula:

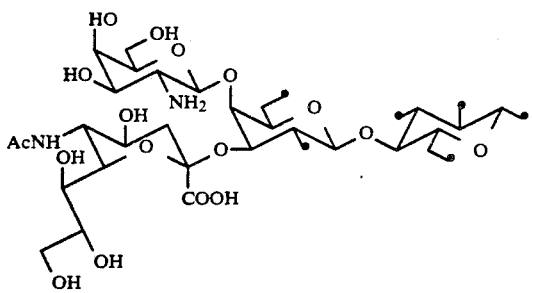

This compound (6) is obtained from the compound (3) by either of the following two methods.

(a) First Method

The compound (3) is first treated with a substance such as NaOCH₃ in a solvent such as methanol, preferably at a temperature of between 0° C. and room temperature. The thus obtained compound is then treated with an alkali such as NaOH in an aqueous solution of methanol at a temperature of between 0° C. and room temperature, thereby obtaining Compound (4) expressed by the following formula:

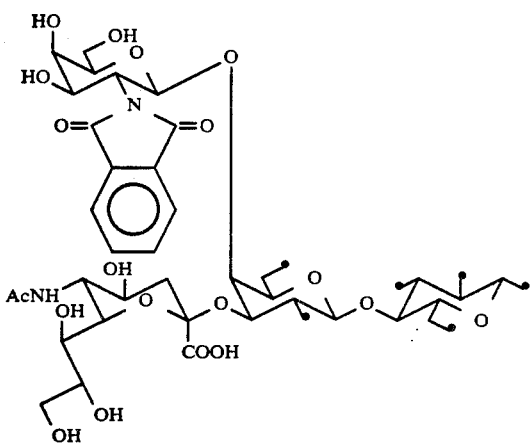

The former treatment is normally effected for 1 to 10 hours.

The thus obtained compound (4) is treated with hydrazine hydrate (H₂NNH₂.H₂O) in a solvent which is either an alcohol such as methanol or ethanol, or an amine such as methylamine or butylamine, preferably at a temperature of between 60° C. and a reflux temperature, thereby obtaining the compound (6). The reaction period is normally about one day to one week.

(b) Second Method

The method (3) is treated in a solvent such as pyridine or collidine in the presence of anhydrous LiI, preferably at a temperature of between 60° C. and a reflux temperature (120° C.), thereby obtaining Compound (5) expressed by the following formula:

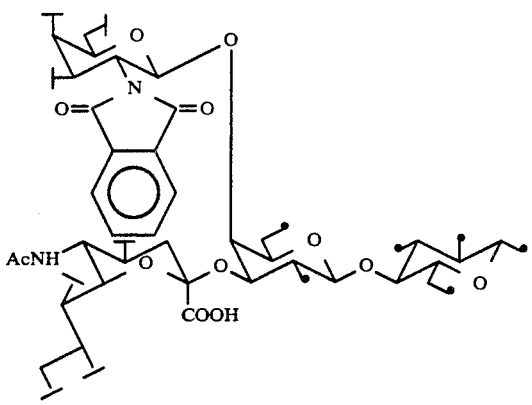

The reaction period is normally 2 to 20 hours.

Then, the thus obtained compound (5) is treated with hydrazine hydrate in a solvent such as ethanol, preferably at a temperature of between 60° C. and a reflux temperature, thereby obtaining the compound (6). The reaction period is normally 1 to 8 hours.

(3) Production of Compound (10) expressed by the following formula:

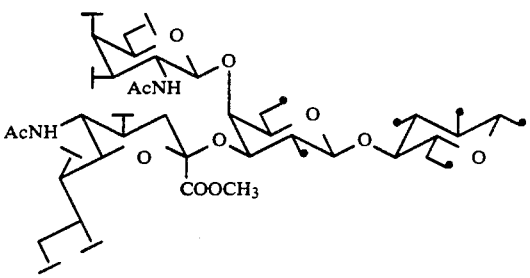

This compound (10) can be prepared from the compound (6) by the following method.

The compound (6) is treated with acetic anhydride in a solvent such as methanol, preferably at a temperature of between 0° C. and room temperature, thereby obtaining two compounds (7) and (8) expressed by the following formulas:

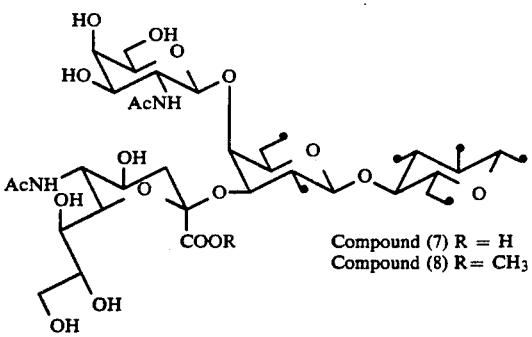

Compound (7) R = H
Compound (8) R = CH₃

These compounds (7) and (8) are treated with acetic anhydride in a solvent such as pyridine, preferably at a temperature of between 0° and 30° C., thereby obtaining two compounds (9) and (10), respectively, which are expressed by the following formulas:

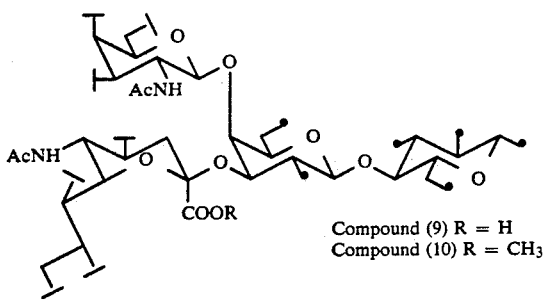

Compound (9) R = H
Compound (10) R = CH₃

In the preparation of the compounds (7) and (8) and in that of the compounds (9) and (10), the reaction period is normally one day to one week.

Then, among the thus obtained two compounds (9) and (10), the compound (9) alone is brought into reaction with diazomethane in a solvent such as methanol, preferably at a temperature of between 0° C. and room temperature so that it becomes the compound (10). The reaction time is normally 1 to 10 hours.

The compound (8) may be prepared by brining the compound (6) into reaction with acetic anhydride in a solvent such as methanol and thereafter with diazomethane. The period during which each of the reactions is effected is normally about one day to one week.

(4) Production of Compound (11) expressed by the following formula:

The compound (10) is first subjected to reduction in a solvent such as methanol in the presence of Pd-C, preferably at a temperature near room temperature. The reaction period is normally 1 to 7 days. Then, the thus reduced compound is acetylated by treating it with acetic anhydride in a solvent such as pyridine, thereby obtaining the compound (11). The reaction period is normally 1 to 7 days.

(5) Production of Compound (12) expressed by the following formula:

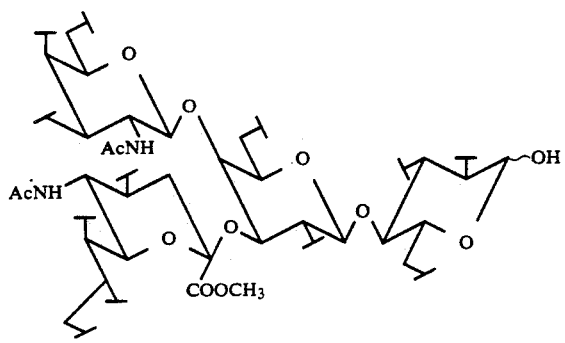

This compound (12) is prepared by treating the compound (11) with hydrazinium acetate (H₂NNH₂.AcOH) in a solvent such as dimethylformamide (DMF). The reaction temperature is preferably between room temperature and 50° C., while the reaction period is normally 1 minute to 3 hours.

(6) Production of Compound (13) expressed by the following formula:

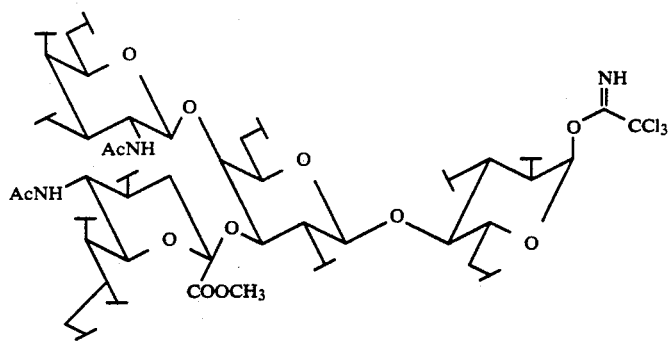

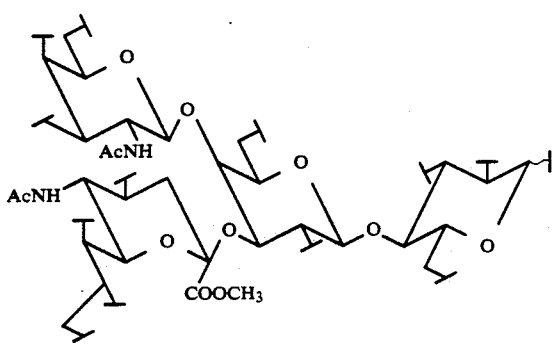

This compound (13) is prepared by bringing the compound (12) into reaction with trichloroacetonitril in a solvent such as methylene chloride in the presence of either NaH or 1,8-diazabicyclo (5,4,0) undeca-7-ene (DBU). The reaction temperature is preferably between 0° and 40° C., while the reaction period is normally 1 to 8 hours.

(7) Production of Compound (15) expressed by the following formula:

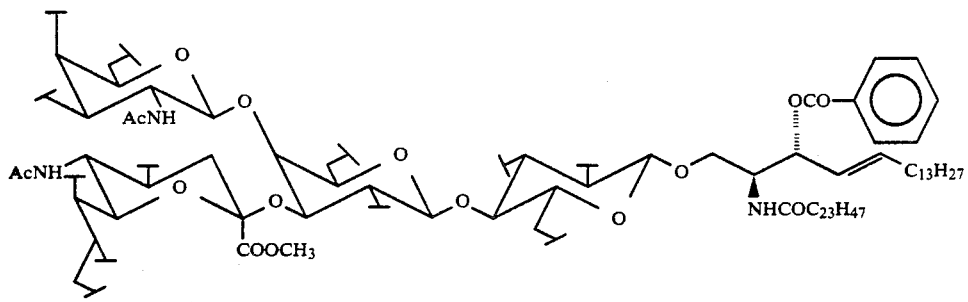

This compound (15) is obtained by reacting a ceramide compound (14) expressed by the following formula:

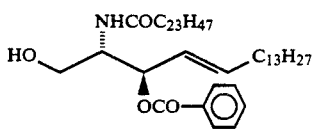

with the compound (13) in a solvent such as CHCl$_3$, in the presence of a glycosidation catalyst such as BF$_3$—Et$_2$O or a Lewis acid catalyst such as SnCl$_4$, AlCl$_4$, TiCl$_4$, TMS Trifrate, in an atmosphere of an inert gas such as argon. The temperature should preferably be between 0° to 30° C. The reaction period is normally 2 to 30 hours.

The ceramide compound (11) is the same as that used in the production of Ganglioside GM$_1$ related compounds and can be synthesized in the same manner.

(8) Production of Compound (16) expressed by the following formula:

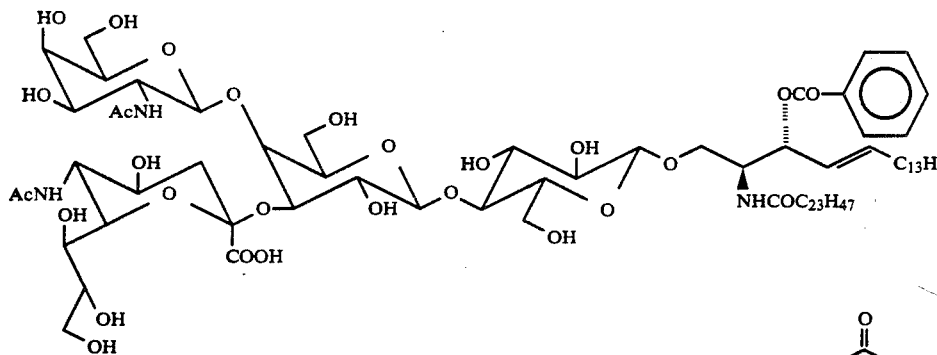

This compound (16) is obtained by first eliminating the acetyl group and the benzoyl group of the compound (15) by using, for instance, MeONa/MeOH as in a normal method, then neutralizing the resulting compound by a cation-exchanger such as Amberlist 15.

An example of a method of producing Ganglioside GM$_2$ related compounds is shown in Scheme IV.

The compounds (9), (10), (11), (12), (13), (14), and (15) are novel compounds.

Utility

These compounds can be used as tumor markers and substances having activities for controlling cell growth.

(C) Production of ganglioside related compounds having the following general formula:

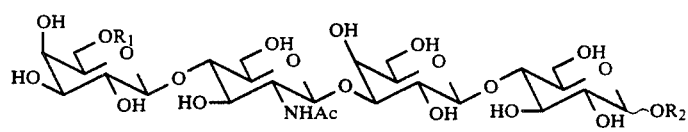

(I)

(wherein R$_1$ represents COCH$_3$ or

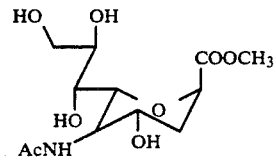

R$_2$, a hydrogen atom or

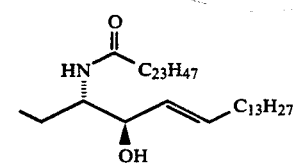

Ac, an acetyl group; Ph, a phenyl group; and

⊢,

The production of the above ganglioside related compounds is explained in detail below on the basis of the production schemes (V to VIII). These schemes show one embodiments for the production of the ganglioside related compounds.

(1) Production of Compound (3)

The compound (3) is produced by reacting a known compound (1) with a known compound (2) under the reaction conditions described below.

$HgBr_3$, $HgBr_2$—$Hg(CN)_2$, $AgOSO_2CF_3$, $Ag_2CO_3$, $AgClO_4$, or silver silicate can be used as a catalyst. $HgBr_2$ is preferable.

$C_2H_4Cl_2$, $CH_2Cl_2$, toluene, nitromethane, benzene, or $CH_3CN$ can be used as a solvent. Dichloroethane is preferable.

The reaction may be carried out under agitation for about 4 to about 48 hours, preferably 33 hours.

The reaction temperature is about 0° to about 80° C., preferably 80° C.

the reaction product thus obtained is purified by a conventional method such as column chromatography.

(2) Production of Compound (4)

The compound (3) is deacetylated and then benzylidenated under the following conditions, to obtain Compound (4).

(Deacetylation reaction)

$CH_3ONa$, $K_2CO_3$, $Na_2CO_3$, or $(C_2H_5)_3N$ can be used as a reagent. $CH_3ONa$ is preferable.

$CH_3OH$ or $C_2H_5OH$ can be used as a solvent. $CH_3OH$ is preferable.

The reaction time is about 0.2 to 12 hours, preferably 0.5 hours, and the reaction can be effected under agitation. The reaction temperature is about −5° C. to 60° C., preferably room temperature.

The thus obtained reaction product is neutralized and then concentrated.

Benzylidenation reaction $TsOH.H_2O$, $ZnCl_2$ or $BF_3O(C_2H_5)_2$ can be used as a catalyst. $TsOH.H_2O$ is preferable.

$CH_3CN$, DMF, or DMF-acetone can be used as a solvent. $CH_3CN$ is preferable.

The reaction time is about 1 hour to 30 hours, preferably 21.5 hours, and this reaction can be effected under agitation.

The reaction temperature is about 0° C. to 80° C., preferably room temperature.

The obtained reaction product is purified by a conventional method such as column chromatography.

(3) Production of Compound (5)

Compound (5) is obtained by acetylating the compound (4) under the reaction conditions described below.

Acetic anhydride-pyridine or acetic anhydride-pyridine-4-DMAP can be used as a reagent or a solvent. Acetic anhydride-pyridine is preferable.

The reaction time is about 0.5 to 12 hours, preferably 3 hours, and this reaction can be effected under agitation.

The reaction temperature is about 0° C. to 80° C., preferably room temperature.

The thus-obtained reaction product is purified by a conventional method such as column chromatography.

(4) Production of Compound (6)

Compound (6) is obtained by benzylating the compound (5) under the reaction conditions described below.

NaH, $(C_2H_5)_3N$, or NaOH can be used as a reagent for this reaction. NaH is preferable.

DMF can be preferably used as a solvent.

The reaction time is about 3 to 12 hours, preferably 5.5 hours, and the reaction can be effected under agitation.

The reaction temperature is about −5° C. to 30° C., preferably room temperature.

The thus-obtained reaction product is purified by a conventional method such as column chromatography.

(5) Production of Compound (7)

Compound (7) is obtained by benzylidenating the compound (6) under the reaction conditions described below.

$CF_3COOH$ or $CH_3COOH$ can be used as a reagent for this reaction. $CF_3COOH$ is preferable.

$CH_2Cl_2$ or $C_2H_4Cl_2$ can be used as a catalyst. $CH_2Cl_2$ is preferable.

The reaction time is about 1 to 12 hours, preferably 2 hours, and this reaction can be effected under agitation.

The reaction temperature is about 0° C. to 50° C., preferably 0° C. to 30° C. The thus-obtained reaction product is purified by a conventional method such as column chromatography.

(6) Production of Compound (8)

Compound (8) is obtained by reacting the compound (7) with Compound (a) under the reaction conditions described below.

$HgBr_2$—$HgCN_2$, $AgOSO_2CF_3$, silver-silicate, $Ag_2CO_3$, $AgClO_4$ or $HgBr_2$ can be used as a catalyst for this reaction. $HgBr_2$—$HgCN_2$ is preferable.

$C_2H_4Cl_2$, $CH_2Cl_2$, toluene, nitromethane, benzene or $CH_3CN$ can be used as a solvent. $C_2H_4Cl_2$ is preferable.

The reaction time is about 1 hour to 90 hours, preferably 60 hours, and this reaction can be effected under agitation.

The reaction temperature is about −15° C. to 60° C., preferably about −15° C. to room temperature.

The obtained reaction product is purified by a conventional method such as column chromatography.

(7) Production of Compound (9)

Compound (9) is obtained by acetylating the compound (8) under reaction conditions described below.

Acetic anhydride-pyridine or acetic anhydride-pyridine-4-DMAP can be used as a reagent or a solvent for this reaction. Acetic anhydride-pyridine is preferable.

The reaction time is about 1 hour to 24 hours, preferably 12 hours, and this reaction can be effected under agitation.

The reaction temperature is about 0° C. to 80° C., preferably room temperature.

The thus-obtained reaction product is purified by a conventional method such a column chromatography.

(8) Production of Compound (10)

Compound (10) is obtained by acetylating the compound (7) under the reaction conditions below.

Acetic anhydride-pyridine-4-DMAP or acetic anhydridepyridine can be used as a reagent or a solvent. Acetic anhydride-pyridine-4-DMAP is preferable.

The reaction time is about 1 hour to 12 hours, preferably 3 hours.

The reaction temperature is about 0° C. to 80° C., preferably room temperature, and the reaction can be effected under agitation.

The thus-obtained reaction product is purified by a conventional method such a column chromatography.

(9) Production of Compound (11)

Compound (11) is obtained by partially hydrolyzing the compound (10) under the reaction conditions described below.

$(\phi_3 P)_3 RhCl$, $PdCl_2$, or $Pd-C-I_2$ can be used as a catalyst for this reaction. $(\phi_3 P)_3 RhCl$ is preferable.

Ethanol-$\phi$-water, acetic acid-water, or methanol-water can be used as a solvent. Ethanol-$\phi$-water is preferable.

The reaction time is about 1 hour to 12 hours, preferably 3 hours, and this reaction can be effected under agitation.

The reaction temperature is about 20° C. to 80° C., preferably a reflux temperature.

The thus-obtained reaction product is purified by a conventional method such as column chromatography.

(10) Production of Compound (12)

Compound (12) is obtained by reacting the compound (11) with $CCl_3CN$ under the reaction conditions described below.

DBU or NaH can be used as a reagent for this reaction. DBU is preferable.

$CH_2Cl_2$, toluene or benzene can be used as a solvent.

The reaction time is about 1 hour to 12 hours, preferably 8 hours, and this reaction can be effected under agitation.

The reaction temperature is about −20° C. to 40° C., preferably room temperature.

The thus-obtained reaction product is purified by a conventional method such as column chromatography.

(11) Production of Compounds (13) and (14)

The compound (12) is reacted with Compound (b) having the following formula:

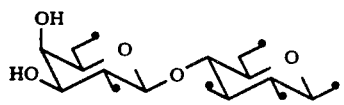 (b)

and then the resultant product is acetylated to obtain Compounds (13) and (14).

Replacement reaction $BF_3O(Et)_2$, TMS-triflate, $TiCl_4$ or $SnCl_4$ can be used as a catalyst for this reaction. $BF_3O(Et)_2$ is preferable.

$C_2H_4Cl_2$, $CH_2Cl_2$, $CHCl_3$, toluene, benzene, or nitromethane can be sued a solvent. $C_2H_4Cl_2$ is preferable.

The reaction time is about 30 minutes to 12 hours, preferably 1.5 hours, and this reaction can be effected under agitation.

The reaction temperature is about −30° C. to 60° C., preferably −25° C.

Acetylation reaction

Pyridine-acetic anhydride or pyridine-acetic anhydride-dimethylaminopyridine can be used as a solvent for this reaction. Pyridine-acetic anhydride is preferable.

The reaction time is about 30 minutes to 36 hours, preferably 24 hours, and this reaction can be effected under agitation.

The reaction temperature is about 0° C. to 80° C., preferably room temperature.

The thus-obtained reaction product is purified by a conventional method such as column chromatography.

(12) Production of Compound (15)

A compound (15) is obtained by reacting the compound with Compound (c) having the following formula, under the reaction conditions described below.

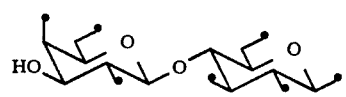 (c)

$BF_3OEt_2$, TMS triflate, $TiCl_4$ or $SnCl_4$ can be used as a catalyst for this reaction. $BF_3OEt_2$ is preferable.

$C_2H_4Cl_2$, $CH_2Cl_2$, $CHCl_3$, toluene, benzene, or nitromethane can be used as a solvent. $C_2H_4Cl_2$ is preferable.

The reaction time is about 0.5 hours to 12 hours, preferably 1 hour, and this reaction can be effected under agitation.

The reaction temperature is about −25° C. to 60° C., preferably −20° C.

The thus-obtained reaction product is purified by a conventional method such as column chromatography.

(13) Production of Compound (16)

The compound (15) is deacetylated, then dephthaloylated, and then acetylated under the reaction conditions described below to obtain Compound (16).

Deacetylation reaction $CH_3ONa$, $K_2CO_3$, $Na_2CO_3$ or $(C_2H_5)_3N$ can be used as a reagent for this reaction. $CH_3ONa$ is preferable.

Methanol or ethanol can be used as a solvent. Methanol is preferable.

The reaction time is about 0.2 hours to 10 hours, preferably 0.5 hours, and this reaction can be effected under agitation.

The reaction temperature is about 0° C. to 60° C., preferably room temperature.

The thus-obtained reaction product is purified by a conventional method such as column chromatography.

Dephthaloylation reaction $H_2NNH_2$—$H_2O$, n-butylamine or an alkylamine can be used as a reagent for this reaction. $H_2NNH_2$—$H_2O$ is preferable.

Ethanol or methanol can be used as a solvent. Methanol is preferable.

The reaction time is about 1 hour to 12 hours, preferably 3 hours, and this reaction can be effected under agitation.

The reaction temperature is about 50° C. to a reflux temperature, preferably a reflux temperature.

The thus-obtained reaction product is purified by a conventional method such as column chromatography.

Acetylation reaction

Acetic acid can be used as a catalyst for this reaction. Methanol, water, or ethanol can be used as a solvent. Methanol is preferable.

The reaction time is about 1 hour to 12 hours, preferably 2 hours, and this reaction can be effected under agitation.

The reaction temperature is about 0° C. to 60° C., preferably room temperature.

The thus-obtained reaction product is purified by a conventional method such as column chromatography.

(14) Production of Compounds (17) and (18)

Compounds (17) and (18) are obtained by reacting, under the reaction conditions described below, the compound (16) with Compound (a) having the following formula:

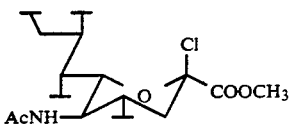

$HgBr_2$—$HgCN_2$, $HgBr_2$, $AgOSO_2CF_3$, silver-silicate, or $Ag_2CO_3$ can be used as a catalyst for this reaction. $HgBr_2HgCN_2$—$HgCN_2$ is preferable.

$CH_2Cl_2$, $C_2H_4Cl_2$, toluene, nitromethane, benzene, or $CH_3CN$ can be used as a solvent. $CH_2Cl_2$ is preferable.

The reaction time is about 1 hour to 40 hours, preferably 27 hours, and this reaction can be effected under agitation.

The reaction temperature is about $-15°$ C. to 60° C., preferably room temperature.

The thus-obtained reaction product is purified by a conventional method such as column chromatography.

(15) Production of Compound (19)

A compound (19) is obtained by acetylating the compound (17) under the reaction conditions described below.

Pyridine-acetic anhydride or pyridine-acetic anhydride-4-dimethylaminopyridine can be used as a solvent for this reaction. Pyridine-acetic anhydride is preferable.

The reaction time is about 0.5 hours to 12 hours, preferably 1 hour, and this reaction can be effected under agitation.

The reaction temperature is about 0° C. to 60° C., preferably room temperature.

The thus-obtained reaction product is purified by a conventional method such as column chromatography.

(16) Production of Compound (20)

A compound (20) is obtained by acetylating the compound (18) under the reaction conditions described below.

Pyridine-acetic anhydride or pyridine-acetic anhydride-4-dimethylaminopyridine can be used as a solvent for this reaction. Pyridine-acetic anhydride is preferable.

The reaction time is about 0.5 hours to 12 hours, preferably 1 hour, and this reaction can be effected under agitation.

The reaction temperature is about 0° C. to 60° C., preferably room temperature.

The thus-obtained reaction product is purified by a conventional method such as column chromatography.

(17) Production of Compound (25)

A compound (25) is obtained by debenzylating the compound (17) and then acetylating the product.

Debenzylation reaction

Pd/C, Pd/C.Pd(OH)$_2$ or PtO$_2$ can be used as a catalyst for this reaction. 10% Pd/C is preferable.

Methanol-water, methanol or methanol-acetic acid can be used as a solvent. Methanol-water is preferable.

The reaction time is about 1 hour to 12 hours, preferably 12 hours, and this reaction can be effected under agitation.

The reaction temperature is about 15° C. to 60° C., preferably room temperature.

The thus-obtained reaction product is purified by a conventional method such as column chromatography.

Acetylation reaction

Pyridine-acetic anhydride or pyridine-acetic anhydride-4-dimethylaminopyridine can be used as a solvent for this reaction. Pyridine-acetic anhydride is preferable.

The reaction time is about 1 hour to 12 hours, preferably 6 hours, and this reaction can be effected under agitation.

The reaction temperature is about 0° C. to 60° C., preferably room temperature.

The thus-obtained reaction product is purified by a conventional method such as column chromatography.

(18) Production of Compound (21)

The compound (18) is debenzylated and then acetylated under the reaction conditions described below, to obtain Compound (21).

Debenzylation reaction

10% Pd/C, 5% Pd/C, Pd(OH)$_2$ or PtO$_2$ can be used as a catalyst for this reaction, but PtO$_2$ is preferably used.

Methanol-water, methanol, or methanol-acetic anhydride can be used as a solvent, but methanol-water is preferably used.

The reaction time is about 1 hour to 12 hours, preferably 12 hours, and this reaction can be effected under agitation.

The reaction temperature is about 15° C. to 60° C., preferably room temperature.

The thus-obtained reaction product is purified by a conventional method such as column chromatography.

(19) Production of Compound (26)

Compound (26) is obtained by partially hydrolyzing the compound (25) under the reaction conditions described below.

$H_2NNH_2$—$CH_3COOH$ can be used as a reagent for this reaction. DMF can be used as a solvent.

The reaction time is about 0.5 hours to 12 hours, preferably 1 hour, and this reaction can be effected under agitation.

The reaction temperature is about 0° C. to 60° C., preferably room temperature.

The thus-obtained reaction product is purified by a conventional method such as column chromatography.

(20) Production of Compound (27)

Compound (27) is obtained by deacetylating the compound (26) under the reaction conditions described below.

$K_2CO_3$ or $CH_3ONa$ can be used as a reagent for this reaction. $CH_3ONa$ is preferable.

Methanol or ethanol can be used as a solvent. Ethanol is preferable.

The reaction time is about 0.5 hours to 12 hours, preferably 1 hour, and this reaction can be effected under agitation.

The reaction temperature is about 0° C. to 60° C., preferably room temperature.

The thus-obtained reaction product is purified by a conventional method such as column chromatography.

(21) Production of Compound (28)

Compound (28) is obtained by reacting the compound (26) with $CCl_3CN$ under the reaction conditions described below.

DBU or NaH can be used as a catalyst for this reaction. DBU is preferable.

$C_2H_4Cl_2$, $CH_2Cl_2$, toluene, or benzene can be used as a solvent. $C_2H_4Cl_2$ is preferable.

The reaction time is about 1 hour to 12 hours, preferably 4 hours, and this reaction can be effected under agitation.

The reaction temperature is about $-20°$ C. to 50° C., preferably room temperature.

The thus-obtained reaction product is purified by a conventional method such as column chromatography.

(22) Production of Compound (29)

Compound (29) is obtained by reacting the compound (28) with Compound (d) having the following formula:

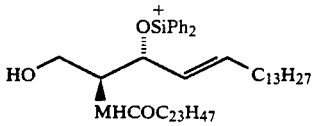

under the reaction conditions described below.

$BF_3O(C_2H_5)_2$, TMS-triflate, $TiCl_4$, or $SnCl_4$ can be used as a catalyst. $BF_3O(C_2H_5)_2$ is preferable.

$C_2H_4Cl_2$, $CH_2Cl_2$, $CHCl_3$, toluene, benzene, or nitromethane can be used as a solvent. $C_2H_4Cl_2$ is preferable.

The reaction time is about 0.5 hours to 12 hours, preferably 1 hour, and this reaction can be effected under agitation.

The reaction temperature is about $-25°$ C. to 60° C., preferably $-20°$ C.

The thus-obtained reaction product is purified by a conventional method such as column chromatography.

(23) Production of Compound (30)

The compound (29) is desilylated, then deacetylated, and then demethylated under the reaction conditions described below, to obtain Compound (30).

Desilylation and deacetylation reactions n-$Bu_4NF/CH_3ONa$ or n-$Bu_4NF/K_2CO_3$ can be used as a reagent. n-$Bu_4NF/CH_3ONa$ is preferable.

THF/$CH_3OH$ or THF/$C_2H_5OH$ can be used as a solvent. THG/$CH_3OH$ is preferable.

The reaction time is about 0.5 hours to 12 hours, preferably 3 hours.

The reaction temperature is about 0° C. to 60° C., preferably room temperature.

The thus-obtained reaction product is purified by a conventional method such as ion exchange.

Demethylation reaction

NaOH, $K_2CO_3$ or KOH can be used as a reagent. 0.01 NaOH is preferable.

$H_2O$, $H_2$—$CH_3OH$, or $H_2O$—$C_2H_{50}H$ can be used as a solvent. $H_2O$ is preferable.

The reaction time is about 0.5 hours to 12 hours, preferably 12 hours, and this reaction can be effected under agitation.

The reaction temperature is about 0° C. to 60° C., preferably room temperature.

The thus-obtained reaction product is purified by a conventional method such as column chromatography.

(24) Production of Compound (22)

Compound (22) is obtained by partially deacetylating the compound (21) under the reaction conditions described below.

$H_2N$ $NH_2CH_3COOH$ can be used as a reagent.

DMF can be used as a solvent.

The reaction time is about 0.2 hours to 12 hours, preferably 0.5 hours, and this reaction can be effected under agitation.

The reaction temperature is about 20° C. to 80° C., preferably 50° C.

The thus-obtained reaction product is purified by a conventional method such as column chromatography.

(25) Production of Compound (23)

The compound (16) is debenzylated and then acetylated under the reaction conditions described below, to obtain Compound (23).

Debenzylation reaction

Pd/C, Pd/C.Pd(OH)$_2$ or PtO$_2$ can be used as a catalyst for this reaction. 10% Pd/C is preferable.

$CH_3OH$—$H_2O$, $CH_3OH$, $CH_3OH$—$CH_3COOH$ can be used as a solvent. $CH_3OH$—$H_2O$ is preferable.

The reaction time is about 1 hour to 36 hours, preferably 12 hours, and this reaction can be effected under agitation.

The reaction temperature is about 20° C. to 60° C., preferably room temperature.

Acetylation reaction

Pyridine/acetic anhydride or pyridine/acetic anhydride/4-dimethylaminopyridine can be used as a solvent. Pyridine/acetic anhydride is preferable.

The reaction time is about 1 hour to 24 hours, preferably 12 hours, and this reaction can be effected under agitation.

The reaction temperature is about 0° C. to 60° C., preferably room temperature.

The thus-obtained reaction product is purified by a conventional method such as column chromatography.

(26) Production of Compound (24)

Compound (24) is obtained by partically deacetylating the compound (23) under the reaction conditions described below.

$H_2NNH_2$ $CH_3COOH$ can be used as a catalyst.

DMF can be used as a solvent.

The reaction time is about 0.5 hours to 12 hours, preferably 0.75 hours, and this reaction can be effected under agitation.

The reaction temperature is about 20° C. to 80° C., preferably 50° C.

The thus-obtained reaction product is purified by a conventional method such as column chromatography.

(27) Production of Compound (31)

Compound (31) is obtained by reacting the compound (24) with $CCl_3CN$ under the reaction conditions described below.

DBU or NaH can be used as a catalyst DBU is preferable.

$C_2H_4Cl_2$, $CH_2Cl_2$, toluene, or benzene can be used as a solvent. $C_2H_4Cl_2$ is preferable.

The reaction time is about 1 hour to 12 hours, preferably 4 hours, and this reaction can be effected under agitation.

The reaction temperature is about $-20°$ C. to $40°$ C., preferably room temperature.

The thus-obtained reaction product is purified by a conventional method such as column chromatography.

(28) Production of Compound (32)

Compound (32) is obtained by reacting the compound (31) with Compound (d) having the following general formula:

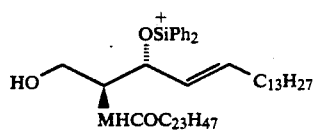

under the reaction conditions described below.

$BF_3O(C_1H_5)_2$, TMS-triflate, $TiCl_4$ or $SnCl_4$ can be used as a catalyst. $BF_3O(C_2H_5)_2$ is preferable.

$C_2H_4Cl_2$, $CH_2Cl_2$, toluene, benzene, or nitromethane can be used as a solvent. $C_2H_4Cl_2$ is preferable.

The reaction time is about 1 hour to 12 hours, preferably 5 hours, and this reaction can be effected under agitation.

The reaction temperature is about $-25°$ C. to $60°$ C. preferably $-20°$ C.

The thus-obtained reaction product is purified by a conventional method such as column chromatography.

(29) Production of Compound (33)

The compound (32) is desilylated and acetylated, and then demethylated under the reaction conditions described below, to obtain Compound (33).

Desilylation and deacetylation reactions $n\text{-}Bu_4NF/CH_3ONa$ or $n\text{-}Bu_4NF/K_2CO_3$ can be used as a catalyst. $n\text{-}Bu_4NF/CH_3ONa$ is preferable.

$THF/CH_3OH$ or $THF/C_2H_5OH$ can be used as a solvent. $THF/CH_3OH$ is preferable.

The reaction time is about 0.5 hours to 12 hours, preferably 2 hours, and this reaction can be effected under agitation.

The reaction temperature is about 0° C. to 60° C., preferably room temperature.

The thus-obtained reaction product is neutralized by a conventional method such as ion exchange.

Utility

The ganglioside related compounds of the present invention have cancer antigen activities which cause the immune reactions with antibodies for the cancer tissues of colon or liver. These compounds are, therefore, useful as markers which lead to earlier detection of cancer and are useful for immunotherapy for cancer.

(D) Production of ganglioside $GD_{1a}$ related compounds having the following general formula:

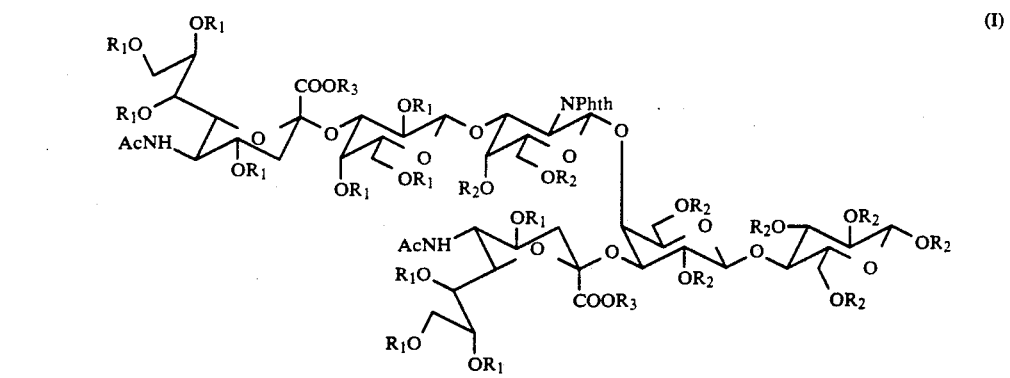

(I)

(wherein $R_1$ represents H or $COCH_3$; $R_2$, H or $C_6H_5CH_2$; $R_3$, H or $CH_3$; Ac, $COCH_3$; and NPhth,

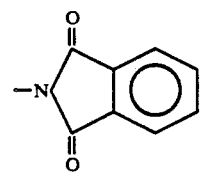

The production of these ganglioside related compounds is explained in detail below on the basis of the production scheme (IX).

Scheme IX
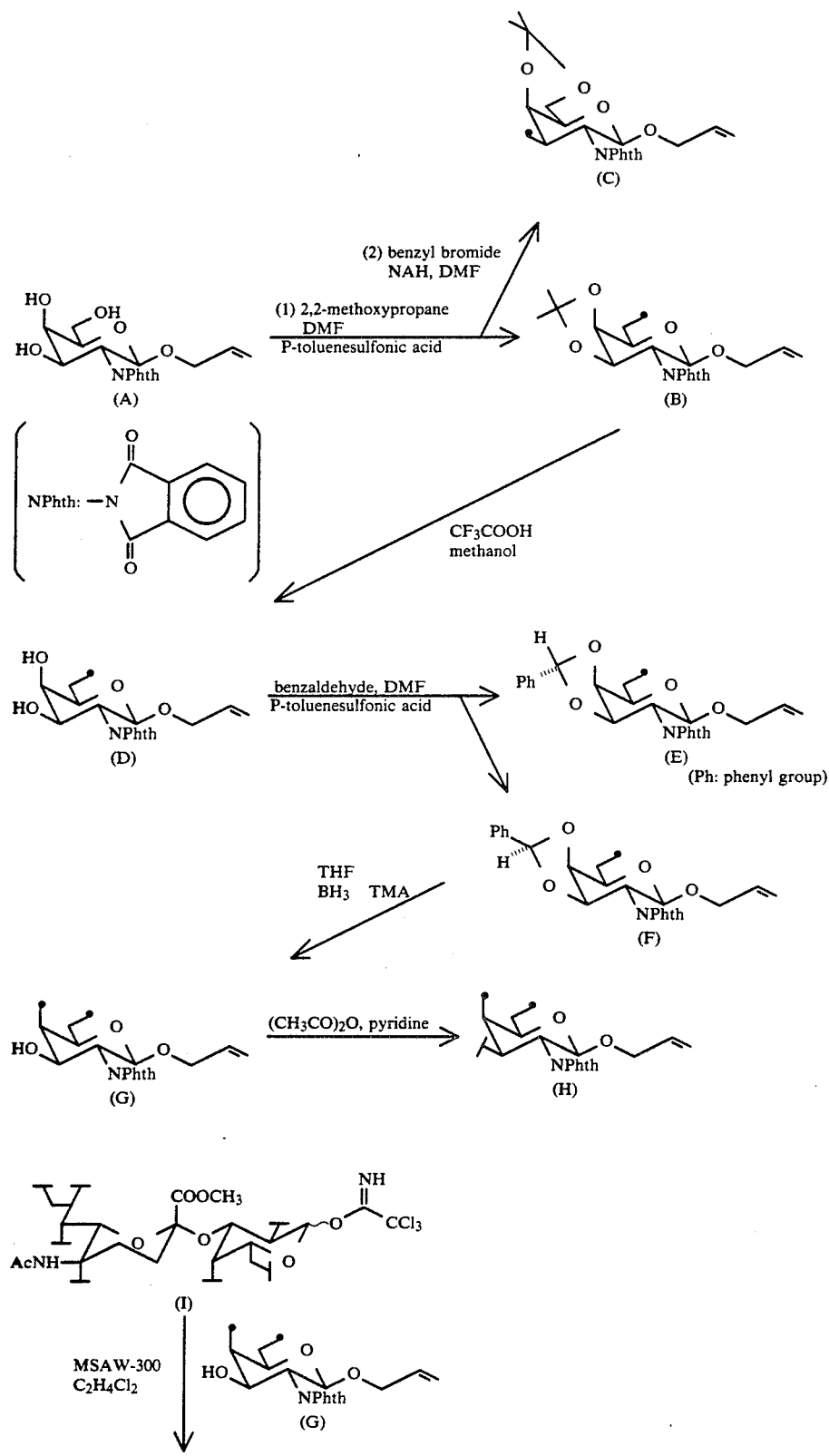

Scheme IX -continued
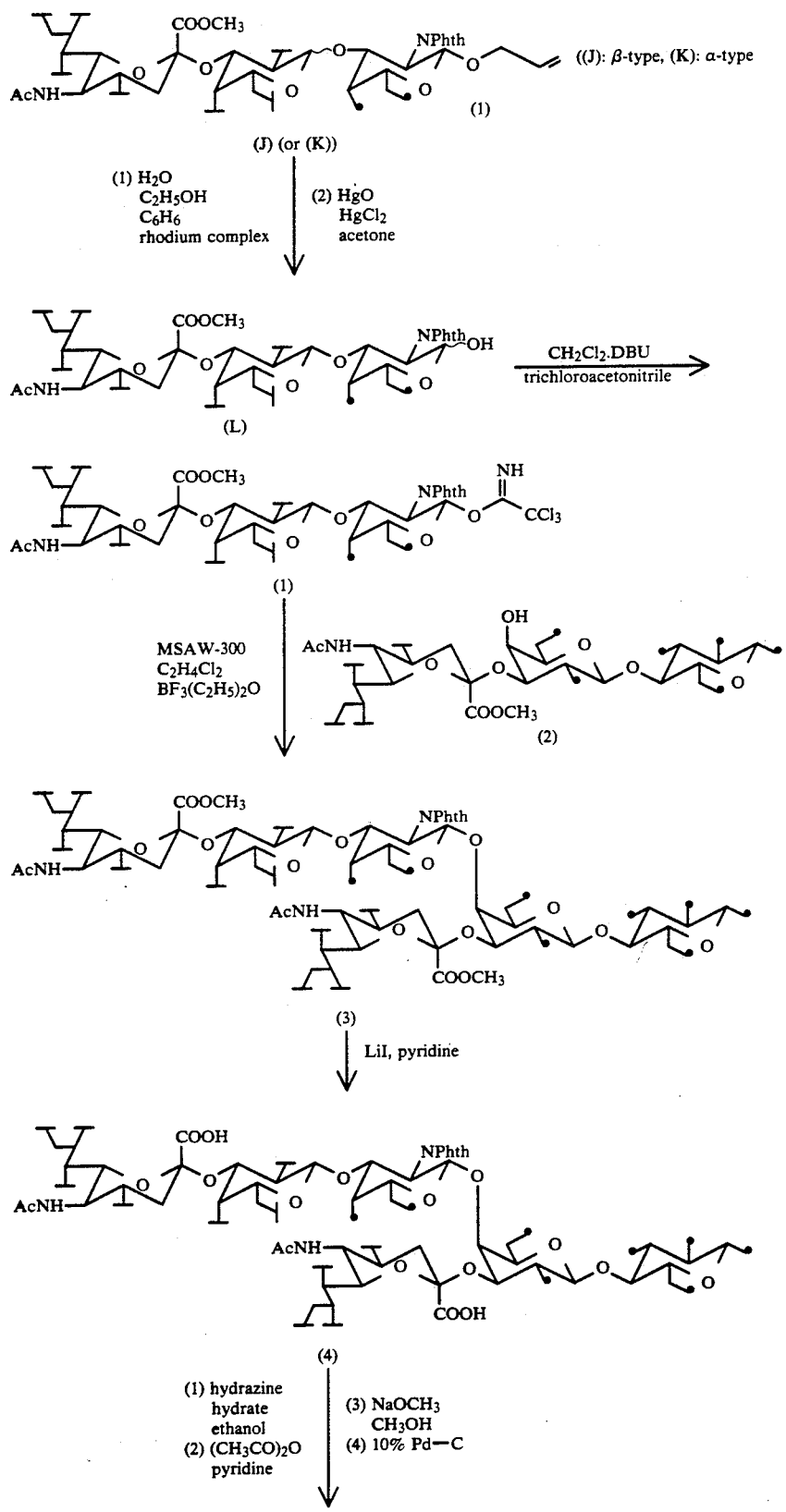

-continued

Scheme IX

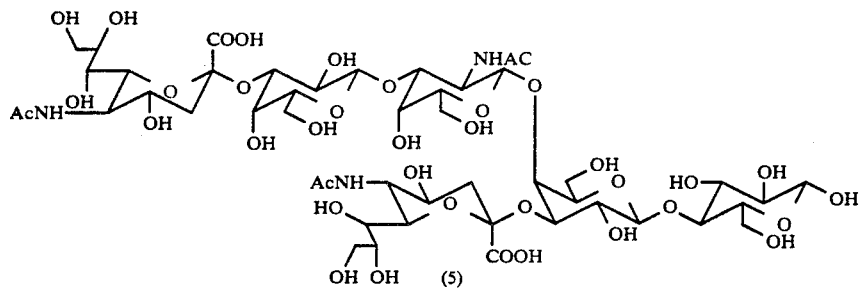

(1) Production of Compounds (B) and (C)

Compound (A) is isopropylidenated and then benzylated under the reaction conditions described below, to obtain Compounds (B) and (C).

Isopropylidenation reaction

2-Methoxypropene can be used as a reagent.

DMF, acetonitrile, or dichloromethane can be used as a solvent. DMF is preferable.

This reaction is effected at a temperature of about 0° C. to 60° C., preferably at room temperature, and proceeds well under agitation for about 0.5 hours to 12 hours, preferably 2 hours.

Benzylation reaction

THF, dioxane, or acetonitrile can be used as a solvent. THF is preferable.

This reaction is effected at a temperature of about 0° C. to 60° C., preferably at room temperature, and proceeds well under agitation for about 0.5 hours to 12 hours, preferably 2 hours.

The thus-obtained reaction product is purified by a conventional method such as column chromatography.

(2) Production of Compound (D)

The compound (B) is reacted under the reaction conditions described below, to obtain Compound (D).

$CF_3COOH$, HCOOH, methanesulfonic acid, paratoluenesulfonic acid, or HCl can be used as a reagent for this reaction.

Methanol, ethanol, THF, dichloromethane, or dichloroethane can be used as a solvent.

This reaction is effected at a temperature of about 0° C. to 90° C., preferably 50° C., and proceeds well under agitation for about 0.1 hours to 24 hours, preferably 12 hours.

The thus-obtained reaction product is purified by a conventional method such as column chromatography.

(3) Production of Compounds (E) and (F)

The compound (D) is reacted with benzaldehyde dimethylacetal under the reaction conditions described below, to obtain Compounds (E) and (F).

$ZnCl_2$ can be used as a catalyst for this reaction.

DMF, THF, dioxane, dichloromethane, or dichloroethane can be used as a solvent. DMF is preferable.

This reaction is effected at a temperature of about 0° C. to 60° C., preferably at room temperature, and proceeds well under agitation for about 0.5 hours to 24 hours, preferably 12 hours.

The thus-obtained reaction product is purified by a conventional method such as column chromatography.

(4) Production of Compound (G)

The compound (F) is treated under the reaction conditions described below, to obtain Compound (G).

$BH_3$—TMA, $NaCNBH_3$, $NaBH_4$, or DIBAL can be used as a catalyst. $BH_3$—TMA is preferable.

THF, toluene, dioxane, ether, or benzene can be used as a solvent. THF is preferable.

This reaction is effected at a temperature of about 0° C. to 70° C., preferably at room temperature, and proceeds well under agitation for about 0.1 hours to 24 hours, preferably 1 hour.

The thus-obtained reaction product is purified by a conventional method such as column chromatography.

(5) Production of Compound (H)

The compound (H) is obtained by acetylating the compound (G) under the reaction conditions described below.

$(CH_3CO)_2O$, $CH_3COCl$, triethylamine, or $CH_3COONa$ can be used as a reagent for this reaction. $(CH_3CO)_2O$ is preferable.

Pyridine, $CH_2Cl_2$, $CHCl_3$, DMF, THF, toluene, or benzene can be used as a solvent. Pyridine is preferable.

This reaction is effected at a temperature of about 0° C. to 80° C., preferably room temperature, and proceeds well under agitation for about 0.1 hours to 24 hours, preferably 12 hours.

The thus-obtained reaction product is purified by a conventional method such as column chromatography.

(6) Production of Compounds (J) and (K)

Compounds (J) and (K) are obtained by reacting Compound (I) with the compound (G) under the reaction conditions described below.

Molecular Sieves AW-300, Molecular Sieves 4A, $BF_3.(C_2H_5)_2O$ or TMS-triflate can be used as a catalyst for this reaction. Molecular Sieves AW-300 or $BF_3.(C_2H_5)_2O$ is preferable.

Dichlorethane, $CH_2Cl_2$, toluene, benzene, THF, or nitromethane can be used as a solvent. Dichloroethane is preferable.

This reaction is effected at a temperature of about $-20°$ C. to 60° C., preferably under ice cooling, and proceeds well under agitation for about 1 hour to 24 hours, preferably 3 hours.

The thus-obtained reaction product is purified by a conventional method such as column chromatography.

(7) Production of Compound (L)

Compound (L) is obtained by partially hydrolyzing the compound (J) under the reaction conditions described below.

Rhodium complexes, triphenylphospine rhodium chloride, PdCl$_2$—NaOCOCH$_3$ or Pd—C—I$_2$ can be used as a catalyst for this reaction. Rhodium complexes are preferable.

The thus-obtained reaction product is purified by a conventional method such as column chromatography.

(8) Production of Compound (1)

Compound (1) is obtained by reacting the compound (L) with CCl$_3$Cn under the reaction conditions described below.

DBU (diazabicycloundecane), NaH, LiH, K$_2$CO$_3$ or DAB10 (diazobicyclooctane) can be used as a catalyst for this reaction. DBU is preferable.

CH$_2$Cl$_2$, THF, toluene, chloroform, or dichlorethane can be used as a solvent. CH$_2$Cl$_2$ is preferable.

This reaction is effected at a temperature of about $-20°$ C. to $40°$ C., preferably under ice cooling, and proceeds well under agitation for about 1 hour to 24 hours, preferably 2 hours.

The thus-obtained reaction product is purified by a conventional method such as column chromatography.

(9) Production of Compound (3)

Compound (3) is obtained by reacting the compound (1) with Compound (2) under the reaction conditions described below.

Molecular Sieves AW-300, Molecular Sieves 4A, BF$_3$.(C$_2$H$_5$)$_2$O or TMS-triflate can be used as a catalyst for this reaction. Molecular Sieves AW-300 or BF$_3$.(C$_2$H$_5$)$_2$O is preferable.

Dichloroethane, dichloromethane, THF, benzene, toluene, or nitromethane can be used as a solvent. Dichloroethane is preferable.

This reaction is effected at a temperature of about $-20°$ C. to $50°$ C., preferably under ice cooling, and proceeds well under agitation for about 0.5 hours to about 24 hours, preferably 1 hour.

The thus-obtained reaction product is purified by a conventional method such as column chromatography.

(10) Production of Compound (4)

Compound (4) is obtained by demethylating the above-described compound (3) under the reaction conditions described below.

LiI, NaI, KI, NaBr, or KBr can be used as a catalyst for this reaction. LiI is preferable.

Pyridine, collidine, picoline, or lutidine can be used as a solvent. Pyridine is preferable.

This reaction is effected at a temperature of about $50°$ C. to $100°$ C. and proceeds well under agitation for about 0.5 hours to 4 hours, preferably 3 hours.

The thus-obtained reaction product is purified by a conventional method such as column chromatography.

(11) Production of Compound (5)

The compound (4) is dephthaloylated, N, O-acetylated, O-deacylated, and debenzylated under the reaction conditions described below, to obtain Compound (5).

Dephthaloylation reaction

Hydrazine hydrate, butylamine, or methylamine can be used as a reagent for this reaction. Hydrazine hydrate is preferable.

Ethanol, methanol, or propanol can be used as a solvent. Ethanol is preferable.

This reaction is effected at a temperature of about $50°$ C. to $100°$ C., preferably under heating reflux, and proceeds well under agitation for about 0.5 hours to 4 hours, preferably 2 hours.

Acetylation reaction (CH$_3$CO)$_2$O or CH$_3$COCl can be used as a reagent for this reaction. (CH$_3$CO)$_2$O is preferable.

Pyridine, THF, DMF, or chloroform can be used as a solvent. Pyridine is preferable.

This reaction is effected at a temperature of about $0°$ C. to $80°$ C., preferably room temperature, and proceeds well under agitation for about 0.1 hours to 4 hours, preferably 1 hour.

O-deacetylation reaction

NaOCH$_3$—CH$_3$OH or K$_2$CO$_3$—CH$_3$OH can be used as a reagent for this reaction. NaOCH$_3$—CH$_3$OH is preferable.

This reaction is effected at a temperature of about $0°$ C. to $50°$ C., preferably room temperature, and proceeds well under agitation for about 0.5 hours to 12 hours, preferably 1 hour.

Catalytic reduction

Pd—C, Pd(OH)$_2$, or PtO$_2$ can be used as a catalyst for this reaction. 10% Pd—C is preferable.

This reaction is effected at a temperature of about $0°$ C. to $50°$ C., and proceeds well under agitation for about 1 hour to 36 hours, preferably 24 hours.

The thus-obtained reaction product is purified by a conventional method such as column chromatography.

Utility

The ganglioside related compounds of the present invention are useful as markers which lead to earlier detection of cancer and immunotherapy for cancer.

EXAMPLES

The present invention will be further explained in detail by referring to the following examples.

(A) As for Ganglioside GM$_1$ related compounds (The compound numbers used in the following examples correspond to those used in the scheme III):

Example 1 (Preparation of Compound (3))

24 mg (0.0276 mmol) of Compound (2) and 31 mg (0.0230 mmol) of Compound (1) were dissolved in 1.0 ml of dichloroethane, and the resultant solution was added to 0.5 g of activated molecular sieves (Aw-300). As the mixture was agitated while cooled with ice in an argon atmosphere, 5 μl (1.5 eq) (0.035 mmol) of BF$_3$.Et$_2$O was added to the mixture. After the mixture was agitated for 3 hours, 5 μl of BF$_3$. Et$_2$O was further added to the mixture. After the temperature has been returned to room temperature, the mixture was agitated for 24 hours. Because the compounds (1) and (2) remained on TCL, they were cooled with ice once more, and, after adding 5 μl of BF$_3$.Et$_2$O, these substances were agitated for 3 hours. They were filtered through Celite to remove insolubles and were concentrated under reduced pressure. The residue was refined by using a silica gel column (SiO$_2$ C-300 20 g) as well as using CHCl$_3$ containing 3% of MeOH and then isopropyl ether containing 15% of MeOH, thereby obtaining 18 mg (38.1%) of Compound (3).

Properties of Compound (3)

Rf: 0.32 (CHCl$_3$ containing 3% of MeOH).

NMR (400 MHz, CDCl$_3$ $\epsilon$ ppm, TMS): 1.422, 1.706, 1.861, 1.867, 1.905, 1.919, 2.031, 2.051, 2.089, 2.129, 2.219 (s, —COCH$_3$); 1.770 (1H, t, J=12.5Hz, H-3eax); 2.828 (1H, dd, J=5.0Hz); 12.5 (H-3eeq); 3.873 (s, —OCH$_3$); 5.232 (1H, b.d, J=3.4Hz, H-4d); 5.279 (1H, d, J=8.54, H-1c); 5.283 (1H, dd, J=2.9, 8.5Hz, H-3c); 5.529 (1H, d, J=3.42Hz, H-4c); 7.18 to 7.40 (benzyl group); 7.58 to 7.86 (phthaloyl group).

Example 2 (Preparation of Compound (4))

166 mg of Compound (3) was dissolved in 10 ml of pyridine, 250 mg of LiI was added to the solution, and the resultant solution was refluxed in an argon atmosphere for 3 hours. The reaction solution was diluted with acetate, was washed with solutions of dil HCl and sat NaCl, and was dried with MgSO$_4$. The resulting substance was concentrated under reduced pressure, and the residue was refined by using a silica gel column (Wakogel C-300, 15 g, chloroform containing 10% of methanol), thereby obtaining 106 mg (64.3%) of Compound (4).

Properties of Compound (4)

Rf: 0.18 (EtOAc containing 2% of HCOOH).

NMR (400MHz, CD$_3$OD $\delta$ ppm, TMS): 1.309, 1.654, 1.799, 1.822, 1.862, 2.005, 2.036, 2.044, 2.061, 2.092, 2.204 (s, COCH$_3$); 3.025 (1H, dd, J=5.0, 10.0Hz, H-3eeq); 5.167 (1H, dd, J 3.9, 11.0Hz, H-3d); 5.188 (1H, d, J=9.3Hz, H-1d); 5.265 (1H, bd, J=2.2Hz, H-4d); 5.274 (1H, dd, J=7.8, 2.69Hz, H-3c); 5.477 (d, J=8.3Hz, H-1c); 5.623 (1H, bd, J=3.18Hz, H-4c).

Elementary analysis (assuming that the compound is C$_{105}$H$_{118}$N$_2$O$_{40}$.2H$_2$O): Theoretical values: C: 60.51; H: 5.90; N: 1.34. Measured values: C: 60.40; H: 5.64; N; 1.34.

Example 3 (Preparation of Compound (6))

112 mg (0.055 mmol) of the compound (4) was dissolved in 5 ml of ethanol, 300 mg of hydrazine hydrate was added to the solution, and the resultant solution was refluxed by heat at room temperature for 2 hours. The reaction solution was evaporated under reduced pressure until it was in a dry state. Then, 2 ml of acetic anhydride as well as 2 ml of pyridine were added to the residue, and the mixture was agitated at room temperature for 24 hours. The reaction solution was evaporated under reduced pressure until it was in a dry state, and the residue was refined by using a silica gel column (Wakogel C-300, 15 g, chloroform containing 10% of methanol), thereby obtaining 92 mgl of the compound (5) (Rf: 0.34, CHCl$_3$ containing 12% of MeOH). 92 mg of the compound was dissolved in 1.0 ml of methanol, to which a newly prepared solution of diazomethane was added. Then, the mixture was left to stand for 30 minutes. The reaction solution was concentrated under reduced pressure, and the residue was purified by using a silica gel column (C-300, 10 g, THF and toluene mixed at a ratio of 6:4), thereby obtaining 45 mg (41.7%) of the compound (6).

Properties of Compound (6))

Elementary analysis (assuming that the compound is C$_{100}$H$_{120}$N$_2$O$_{39}$): Theoretical values: C: 60.84; H: 6.13; N: 1.42. Measured values: C: 61.18; H: 6.20; N: 1.33.

Example 4 (Preparation of Compound (7))

24 mg (0.012 mmol) of the compound 6) was dissolved in a mixture of methanol and water (85:15 in volume), 24 mg of 10% Pd-c was added to the solution, and then the mixture was subjected to catalytic reduction for 24 hours. The reduced solution was filtered to remove Pd-c, and was concentrated under reduced pressure. 1.0 ml of acetic anhydride and 1.0 ml of pyridine were added to the residue, which was agitated at room temperature for 24 hours. The mixture was evaporated under reduced pressure until it was in a dry state, and the residue was purified by using a silica gel column (Wakogel C-300, 10 g, CHCl$_3$ containing 5% of MeOH), thereby obtaining 16 mg (78%) of Compound (7).

Properties of Compound (7):

Rf: 0.45 (CHCl$_3$ containing 5% of MeOH).

Elementary analysis (assuming that the compound is C$_{70}$H$_{96}$N$_2$O$_{45}$): Theoretical values: C: 49.88; H: 5.74; N: 1.66. Measured values: C: 50.20; H: 5.63; N: 1.45.

Example 5 (Preparation of Compound (8)

12.6 mg (7.4×10$^{-3}$ mmol) of the compound (7) was dissolved in 0.2 ml of DMF. After adding 1.5 mg of NH$_2$NH$_2$AcOH thereto, the mixture was agitated by heat at 50° C. for 5 minutes. After cooling the reaction solution, it was diluted with ethyl acetate and was washed with a saturated salt solution. Thereafter, the resulting substance was dried with MgSO$_4$, and was evaporated under reduced pressure until it was in a dry state. The residue was purified by using a silica gel column (Wakogel C-300, 1.0 g, CHCl$_3$ containing 5% of MeOH), thereby obtaining 9.0 mg (73.3%) of the compound (8).

Properties of Compound (8):

[$\alpha$]$_D^{19}$:+4.17 (CHCl$_3$, C=0.36).

NMR (400MHz, CDCl$_3$ $\delta$ ppm, TMS): 1.731 (t, J 12.7Hz, H-3eax); 1.860 to 2.219 (51H, —OCOCH$_3$); 2.859 (1H, dd, J 4.4, 13.2Hz, H-3eeq); 3.817 (s, —OCH$_3$).

Rf: 0.37 (CHCl$_3$ containing 5% of MeOH, HPTLC).

Example 6 (Preparation of Compound (9))

7.1 mg (4.32×10$^{-3}$ mmol) of the compound (8) was dissolved in 0.2 ml of dichloromethane, to which 3 $\mu$l of trichloroacetonitrile and 1 $\mu$l of DBU were added. The resultant solution was agitated for 2 hours in an argon atmosphere. The reaction solution was purified by using a silica gel column (Wakogel C-300, 1.0 g, ethyl acetate: acetone=4:1), thereby obtaining 5.7 mg (73.8%) of the compound (9).

Properties of Compound (9)

[$\alpha$]$_D^{19}$: +6.8 (CHCl$_3$, C=0.12).

Rf: 0.40 (ethyl acetate: acetone=4:1).

NMR (400MHz, CDCl$_3$ $\delta$ ppm, TMS): 1.726 (1H, t, J 12.7Hz, H-3eax); 1.856, 1.971, 2.021, 2.028, 2.036, 2.043, 2.048, 2.062, 2.068, 2.076, 2.085, 2.100, 2.108, 2.138, 2.151, 2.222 (s, COCH$_3$); 2.858 (1H, dd, J=5.5, 12.4Hz, H-3eeq); 4.800 (1H, m, H-4e); 3.819 (s, —OCH$_3$); 5.336 (1H, bd, J=3.4Hz, H-4c); 5.355 (1H, bd, J=3.6Hz, H-4d); 5.410 (1H, dd, J=2.7, 9.8Hz, H-3d); 6.382 (1H, d, J=6.3Hz, NH); 6.491 (1H, d, J=3.9Hz, H-1a); 8.655 (1H, s, =NH).

Example 7 (Preparation of Compound (11))

5.7 mg ($3.19 \times 10^{-3}$ mmol) of the compound (9) and 3.6 mg ($4.79 \times 10^{-3}$ mmol) of the compound (10) were dissolved in 0.2 ml of chloroform, which were added to 250 mg of activated molecular sieves (Aw-300). While the resultant mixture was agitated in an argon flow with the mixture cooled with ice, 10 μl of a 0.48N—BF$_3$.Et$_2$O in CHCl$_3$ was added thereto, followed by agitation for 5 hours. After diluting the resultant mixture with chloroform, it was filtered through Celite. The filtrate was evaporated under reduced pressure until it was in a dry state and was purified by using a silica gel column (Wakogel C-300, 1.0 g, CHCl$_3$ containing 4% of methanol), thereby yielding 1.4 mg of the compound (11) and 2.5 mg of unreacted compound (9) (33%).

Properties of Compound (11)

Rf: 0.45 (CHCl$_3$ containing 5% of MeOH, HPTLC).
NMMNR (400MHz, CDCl$_3$ δ ppm, TMS): 0.878 (t, J=6.6Hz, —CH$_2$CH$_3$); 1.252 (S—CH$_2$—); 1.86 to 2.20 (51H, COCH$_3$); 1.750 (1H, t, J=12.5Hz, H-3eax); 2.857 (1H, dd, J=5.0, 12.7Hz, H-3eeq); 3.833 (3H, s, —OCH$_3$); 4.806 (1H, m, H-4e); 5.606 (1H, dd, J=8.0, 15.5Hz, —CH=CH—CH$_2$—); 5.838 (1H, d t, J=7.5, 15.5Hz, —CH=CH—CH$_2$—); 7.450 (2H, dd, J=8.2, 15.7Hz, aromatic proton); 7.582 (1H, m, aromatic proton); 8.05 (1H, m, aromatic proton).

Example 8 (Preparation of Compound (12))

1.4 mg ($0.59 \times 10^{-3}$ mmol) of the compound (11) was dissolved in 0.5 ml of methanol and then 5 μl of N.NaOCH$_3$ was added to the solution, which in turn was agitated at room temperature for 24 hours. The reaction solution was concentrated under reduced pressure and was dissolved again in 0.5 ml of methanol, to which 0.1 ml of H$_2$O was added, followed by agitation for 3 hours. The resultant mixture was neutralized by Amberlist 15, was filtered, and then was concentrated under reduced pressure, thereby obtaining 0.8 mg of the compound (12).

(Properties of Compound (12))

Rf: 0.55 (n-BuOH: EtOH: H$_2$O=4:2:2, HPTLC)
NMR (400MHz, d-6DMSO, D$_2$O=49:1, 30° C., TMS): 0.86 (6H —CH$_2$ CH$_3$, t, 6.5Hz); 1.232 (s, —CH$_2$—); 1.752, 1.878 (s, NHCOCH$_3$); 4.152 (1H, d, J 7.6Hz, H-1a); 4.213 (1H, d, J 7.5Hz, H-1d); 4.278 (1H, d, J=7.7Hz, H-1b); 4.859 (1H, d, J=8.8Hz, H-1c).

Reference Example (Preparation of Compound (6) from Compound (13))

15 mg ($8.9 \times 10^{-3}$ mmol) of the compound (6) was dissolved in 1.0 ml of methanol to which 0.1 ml of NaOCH$_3$ was added, followed by agitation at room temperature for 2 hours. 0.1 ml of H$_2$O was added to the reaction solution, which was agitated at room temperature for 24 hours. Then, the resultant solution was neutralized by Amberlist 15, and resin was removed from the solution by filtering. The filtrate was evaporated under reduced pressure until it was in a dry state. The residue was dissolved in 3 ml of a mixed solvent of methanol and water (4:1), and then 15 mg of 10% Pd-c was added to the resultant solution, which was sufficiently catalytically reduced in a hydrogen atmosphere for one day. After removing Pd-c by filtering, the solution was concentrated under reduced pressure. The residue was dissolved in a small amount of water, and was purified by using a gel filter (G-10. 1 cm × 25 cm), thereby obtaining 7.1 mg (92%) of the compound (13).

Properties of Compound (13)

Rf: 0.21 (n-BuOH: EtOH: H$_2$O=4:2:2).
NMR (400MHz, D$_2$O (5° C.) 6 ppm, HOD 4.99 ppm): 1.946 (1H, t, J=12.2Hz, H-3eax); 2.004, 2.028 (s, COCH$_3$); 2.651 (1H, dd, J=4.4, 12.4Hz, H-3eeq): 3.267 (1H, t, J=8.2Hz, H-2a8); 3.326 (1H, m, H-2b); 4.537, 4.542 (each 1H, d, J=8.0, 7.8Hz, H-1b, H-1d); 4.668 (1H, d, J=7.8Hz, H-1aβ); 4.769 (1H, d, J=8.5Hz, H-1c); 5.21 (1H, d, J=3.91Hz, H-1aα).

(B) As for ganglioside GM$_2$ related compounds (The compound numbers used in the following examples correspond to those used in the scheme IV):

Example 1 (Preparation of Compound (3))

271 mg (0.20 mmol) of the compound (1)[1], 299 mg (0.60 mmol) of the compound (2)[2], and 5 ml of methylene chloride were added to 2 g of activated molecular sieves 4A. To the
mixture, 1206 mg (0.80 mmol) of AgOSO$_2$CF$_3$ was added in an argon atmosphere, and agitated at room temperature for 24 hours. Then, 82 mg (1.0 mmol) of anhydrous acetic acid soda was added to the reaction solution, which was agitated for a hour and a half. The mixture was filtered to remove insolubles, and was washed with acetic ester. The washing solution and the filtrate were mixed and they were washed with saturated sodium bicarbonate and saturated salt water, dried with anhydrous magnesium sulfate, and concentrated under reduced pressure. The residue was purified by using a silica gel column (Wakogel C-300, 40 g, toluene : ethyl acetate=2:9), thereby obtaining 212 g (59.8%) of the compound (3).

Properties of Compound (3)

Rf: 0.57 (EtOAc).
Elementary analysis (assuming that the compound is C$_{94}$H$_{104}$N$_2$O$_{32}$): Theoretical values: C: 63.65; H: 5.91; N: 1.58. Measured values: C: 63.40; H: 6.01; N: 1.77.
NMR (400MHz, CDCl$_3$ δ ppm, TMS): 1.71, 1.82, 1.85, 1.93, 1.93, 2.04, 2.06, 2.21 (s, COCH$_3$); 2.78 (1H, d, d, J 5, 13Hz, H-3deq); 3.89 (3H, s, —OCH$_3$); 5.43 (1H, d, J 8Hz, H-1c)); 5.52 (1H, broad d, J=3Hz, 1H-4c); 6.13 (1H, d, d, J=3, 11Hz, H-3c); 7.10 to 7.45 (benzyl group proton); 7.55 to 7.88 (phthaloyl group proton).

[1]: Carbohydr. Res., 135 (1985) C5-C9.
[2]: Can. J. Chem., 57, (1979) 1244–1251.

Example 2 (Preparation of Compound (4))

200 mg (0.113 mmol) of the compound (3) was dissolved in 10 ml of methanol. 10 ml of a solution of 0.1N—NaOH was added to the solution while cooling the solution by ice and agitating it. After the solution was agitated at the same temperature for 3 hours and a half, the solution was neutralized by Amberlist 15, filtered and then concentrated under reduced pressure. The residue was washed with ether, thereby obtaining 142 mg (85.9%) of the compound (4).

Property of Compound (4)

Rf 0.59 (n-BuOH: EtOH: H$_2$O=4:2:2).

Example 3 (Preparation of Compound (6) from Compound (4))

130 mg (0.088 mmol) of the compound (4) was dissolved in 2 ml of ethanol, and 13 μl of hydrazine hydrate was added to the solution, which in turn was refluxed while it was heated for 72 hours. The reaction solution was evaporated under reduced pressure until it was in a dry state. The residue was dissolved in methanol, and was developed with methanol by using a column of Sephadex LH 20 (2.5 cm×20 cm), thereby obtaining 97 mg (80%) of the compound (6).

Properties of Compound (6)

Rf: 0.66 (n-BuOH : EtOH: $H_2O$=4:2:2).

NMR (90MHz, $CD_3OD$ δ ppm, TMS): 2.64 (1H, m, H-3deq); 2.03 (3H, s, —NHCO$\underline{CH_3}$); 7.22, 7.32 (s, 30H, aromatic proton).

Example 4 (Preparation of Compound (5) from Compound (3))

6 ml of pyridine and 200 mg of the compound (3) were added to lithium iodide which had been dried under reduced pressure at 180° C. for 2 hours. The resultant mixture was refluxed in an argon atmosphere for 6 hours, and then concentrated under reduced pressure. The residue was dissolved in ethyl acetate, was washed with dilute hydrochloric acid and saturated salt water, and was dried with $MgSO_4$. The resulting substance was then concentrated under reduced pressure, and the residue was purified by using a silica gel column (Wakogel C-300, 18 g, $CHCl_3$ containing 10 of MeOH), thereby obtaining 182 mg (92%) of the compound (5).

(Properties of Compound (5))

Rf: 0.49 (chloroform containing 10% of MeOH).

Elementary analysis ($C_{93}H_{102}N_2O_{32}.2H_2O$). Theoretical values: C: 62.20; H: 5.94; N: 1.56. Measured values: C: 61.92; H: 5.64; N: 1.55.

NMR (400MHz, $CD_{30}D$ δ ppm, TMS): 1.518 (1H, t, J 12.2Hz, H-3dax); 1.676, 1.803, 1.872, 2.026, 2.029, 2.042, 2.197 (s, —CO$\underline{CH_3}$×8); 2.921 (1H, dd, J=5.0, 11.3Hz, H-3deq); 5.189 (1H, d, J=9.5Hz, H-1b); 5.278 (1H, dd, J 2.5, 9.2Hz, H-7d); 5.50 (1H, m, H-8d); 5.552 (1H, bd, J=3.1Hz, H-4c); 5.574 (1H, d, J=8.5Hz, H-1c); 6.200 (1H, dd, J=3.4, 11.7Hz, H-3c).

Example 5 (Preparation of Compound (6) from Compound (5))

182 mg (0.103 mmol) of the compound (5) was dissolved in 5 ml of ethanol, to which 460 mg of hydrazine hydrate was added, followed by refluxing for 4 hours. The reaction solution was concentrated under reduced pressure. The residue was dissolved in methanol, and was developed with methanol by using a column of Sephadex LH 20 (2.5 cm×40 cm), thereby obtaining 106 mg (75%) of the compound (6). (The same NMR data as those obtained in Example 3 were obtained.)

Example 6 (Preparation of Compounds (9) and (10) from Compound (6))

108 mg (0.079 mmol) of the compound (6) was dissolved in 5 ml of methanol, to which 100 mg of acetic anhydride was added, followed by agitation at room temperature for 24 hours, thereby obtaining the compounds (7) and (8) (Rf (TLC 2 spot, EtDAc: EtOH: $H_2O$=5:2:1): 0.34 (compound (7)); 0.63 (compound (8)). The compounds (7) and (8) were then evaporated under reduced pressure until they were in a dry state. After adding 1 ml of pyridine and 1 ml of acetic anhydride to the residue, the residue was agitated at room temperature for 24 hours, and then concentrated under reduced pressure. The resulting residue was dissolved in ethyl acetate, was washed with dilute hydrochloric acid and saturated salt water, and was dried with $MgSO_4$ and concentrated under reduced pressure. The residue was then purified by using a silica gel column (C-300, 15 g, chloroform containing 15% of methanol), thereby obtaining 102 mg (77.2%) of the compound (7) and 29 mg (21.7%) of the compound (8).

Compound (9): Rf: 0.33 (15% MeOH-containing $CHCl_3$).

Compound (10): Rf: 0.41 (4% MeOH-containing $CHCl_3$).

Example 7 (Preparation of Compound (10) from Compound (9))

102 mg (0.061 mmol) of the compound (9) was dissolved in 1.0 ml of methanol, to which 1.0 ml of a diazomethane ether solution was added, followed by agitation at room temperature for 2 hours. The mixture was concentrated under reduced pressure, and the residue was purified by using a silica gel column (Wakogel C-300, 10 g, chloroform containing 4% of MeOH), thereby obtaining 95 mg (92.4%) of the compound (10).

Properties of Compound (10)

Elementary analysis: Theoretical values: C: 62.70; H: 6.22; N: 1.66. Measured values: C: 62.42; H: 6.19; N: 1.62.

$[\alpha]_D^{23}$: −11.3 (C=0.86, $CHCl_3$).

NMR (400MHz, $CDCl_3$ δ ppm, TMS): 1.874, 1.912, 1.923, 1.980, 2.003, 2.123, 2.204 (s, —CO$CH_3$); 2.294 (1H, t, J=11.7Hz, H-3dax); 3,191 (s, $OCH_3$); 7.15 to 7.50 (aromatic proton).

Example 8 (Preparation of Compound (8) from Compound (6))

95 mg (0.07 mmol) of the compound (6) was dissolved in 1.0 ml of methanol, 43 mg of acetic anhydride was added to the solution, which was agitated at room temperature for 24 hours. The reaction solution was evaporated under reduced pressure. The residue was dissolved in methanol, to which an excessive amount of a diazomethane solution was added, followed by agitation at room temperature for 24 hours. After the reaction solution was concentrated under reduced pressure, the residue was purified by using a silica gel column (Wakogel C-300, 10 g, chloroform containing 20% of methanol), thereby obtaining 38 mg (39%) of the compound (8).

Properties of Compound (8)

$[\alpha]_D^{17}$: +9.80 ($CH_3OH$, C=0.95).

Elementary analysis. Theoretical values: C: 63.05; H: 6.58; N: 1.99 (assuming that the compound is $C_{74}H_{90}N_2O_{24}.H_2O$). Measured values: C: 63.06; H: 6.56; N: 2.29.

NMR (400 MHz, $CD_3OD$ δ ppm, TMS): 1.951, 2.023 (s, —CO$CH_3$×2); 2.174 (1H, t, J=11.4Hz, H-3dax); 2.539 (1H, dd, J 4.6, 13.6Hz, H-3deq); 3.928 (3H, s, —$OCH_3$).

Example 9 (Preparation of Compound (11) from Compound (10))

93 mg (0.055 mmol) of the compound (10) was dissolved in 5 ml of methanol, to which 50 mg of 10% Pd—C was added. Then, the solution was catalytically reduced in a hydrogen atmosphere for 24 hours. The reduced solution was filtered to remove Pd—C. The filtrate was concentrated under reduced pressure. 1 ml of acetic anhydride and 1 ml of pyridine were added to the residue, which was agitated at room temperature for 24 hours and were concentrated under reduced pressure. The residue was purified by using a silica gel column (Wakogel C-300, 10 g, CHCl$_3$ containing 50% of MeOH), thereby obtaining the compound (11).

Properties of Compound (11)

Elementary analysis (assuming that the compound is C$_{58}$H$_{80}$N$_2$O$_{37}$). Theoretical values: C: 49.85; H: 5.77; N: 2.00. Measured values: C: 49.44; H: 5.78; N: 2.30.

Rf: 0.36 (CHCl$_3$ containing 5% of MeOH).

Example 10 (Preparation of Compound (12) from Compound (11))

69 mg (0.049 mmol) of the compound (11) was dissolved in 0.5 ml of DMF. While the solution was agitated at 50° C., 6 mg of NH$_2$NH$_2$.AcOH was added to the solution, which was agitated for 5 minutes. The reaction solution was diluted with ethyl acetate, and was washed with a saturated salt water. Thereafter, the resulting substance was dried with anhydrous magnesium sulfate, and was concentrated under reduced pressure. The residue was purified by using a silica gel column (Wakogel C-300, 15 g, CHCl$_3$ containing 5% of MeOH), thereby obtaining 40 mg (60%) of the compound (12).

Properties of Compound (12)

Rf: 0.30 (CHCl$_3$ containing 5% of MeOH).
Elementary analysis (assuming that the compound is C$_{56}$H$_{78}$N$_2$O$_{36}$). Theoretical values: C: 49.63; H: 5.80; N: 2.07. Measured values: C: 49.51; H: 5.65; N: 2.02.

Example 11 (Preparation of Compound (13) from Compound (12))

39 mg (0.029 mmol) of the compound (12) was dissolved in 1.0 ml of dichloromethane, to which 24 mg of trichloroacetonitril and 2 μl of DBU were added, followed by agitation for 2 hours in an argon atmosphere while cooling by ice. The reaction solution as purified by using a silica gel column (Wakogel C-300, 8 g, EtOAc: acetone=4:1), thereby obtaining 31 mg (71.8%) of the compound (13).

Properties of Compound (13)

Rf: 0.54 (acetone: EtOAc=1:4).
NMR (400MHz, CDCl$_3$ δ ppm, TMS): 1.858, 1.985, 1.996, 2.017, 2.020, 2.030, 2.059, 2.065, 2.071, 2.092, 2.095, 2.140, 2.142 (s, —COCH$_3$); 1.744 (1H, t, J=12.9Hz, H-3dax); 2.847 (1H, dd, J=4.4, 13.1Hz, H-3deq); 3.841 (3H, s, OCH$_3$); 4.820 (1H, m, H-4d); 5.365 (1H, bd, J=3.4Hz, H-4c); 5.398 (1H, dd, J=2.6, 9.7Hz, H-3b); 5.905 (1H, dd, J=3.41, 11.23Hz, H-3c); 6.493 (1H, d, J=3.91Hz, H-1a); 8.65 (1H, s, =NH).

Example 12 (Preparation of Compound (15) from Compound (13))

27 mg (0.018 mmol) of the compound (13) and 16 mg (0.021 mmol) of the benzoylated ceramide (the compound (14)) were dissolved in 0.5 ml of chloroform, and the solution was added to 0.5 g of activated molecular sieves (AW-300). While agitating the solution in an argon atmosphere with the solution cooled by ice, 3 μl of BF$_3$.Et$_2$O was added to the solution, which was agitated for 2 hours. Then, the temperature of the solution was changed to room temperature, and the solution was agitated for 24 hours. The reaction solution was diluted with chloroform and filtered through Celite. The filtrate wa concentrated under reduced pressure. The residue was purified by using a silica gel column (Wakogel C-300, 8 g, chloroform containing 4% of methanol), thereby obtaining 4 mg (10.6%) of the compound (5).

(Properties of Compound (15)

[α]$_D^{18}$: −12.2° (C=0.12, CHCl$_3$).
NMR (400MHz, CDCl$_3$ δ ppm, TMS): 0.878 (t, J 6.5Hz, —CH$_2$CH$_3$); 1.253 (s, —CH$_2$—); 1.859, 1.911, 1.946, 1.990, 2.018, 2.025, 2.028, 2.061, 2.072, 2.105, 2.130, 2.142, 2.180 (s, —COCH$_3$); 3.836 (s, —OCH$_3$); 2.82 (1H, m, H-3d); 4.81 (1H, m, H-4d); 7.37 to 7.60 (benzoyl group).

Example 13 (Preparation of Compound (16) from Compound (15))

3.0 mg (1.43×10$^{-3}$ mmol) of the compound (15) was dissolved in 0.2 ml of methanol/THF (1/1 in volume), 10 μl of N—NaOCH$_3$ was added to the solution, which was agitated at room temperature for 3 hours and then concentrated under reduced pressure. After adding 0.2 ml of methanol/THF (1/1 in volume) again to the resulting substance and further adding 0.1 ml of H$_2$O, the resultant mixture was agitated for 24 hours, which mixture was neutralized by Amberlist 15, filtrated, and concentrated under reduced pressure. The residue was dissolved in a mixed solvent of CHCl$_3$:CH$_3$OH: H$_2$O (=60:30:4.6), and was purified by using an LH-20 column (1 cm×10 cm), thereby obtaining 0.8 mg of the compound (16).

Properties of Compound (16)

Rf: 0.53 (BuOH: EtOH: H$_2$O=4:2:2).
NMR (400MHz, d-6DMSO/D$_2$O=49/1 in volume at 30° C. δ ppm, TMS): 0.86 (t, J=6.5Hz, —CH$_2$CH$_3$); 1.232 (s, —CH$_2$—); 1.773, 1.871 (s, COCH$_3$); 1.616 (1H, t, J=12.0Hz, H-3dax); 2.556 (1H, dd, J=5.2, 12.7Hz, H-3dsq); 2.021 (2H, t, J=7.1Hz, —NHCOCH$_2$); 1.919 (2H, m, =CH—CH$_2$—); 3.034 (1H, t, J=7.8Hz, H-2a); 4.148 (d, J=8.3Hz, H-1a), 4.269 (d, J=7.8Hz, H-1b); 4.805 (1H, d, J=9.0Hz, H-1c); 5.345 (dd, J=7.5Hz, 15.4, —CH=CH—CH$_2$—); 5.528 (1H, d t, J=15.0, 6.7Hz, —CH=CH—CH$_2$—).

(C) As for ganglioside related compounds having the following general formula:

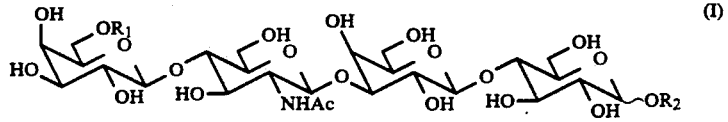

(wherein R$_1$ represents a hydrogen atom or

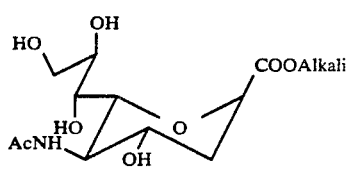

and R₂ represents a hydrogen atom or

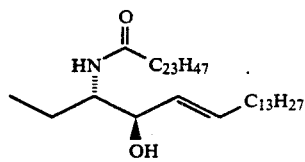

and Ac represents an acetyl group).

(The compound numbers used in the following reference examples and examples correspond to those used in Schemes V-VIII.)

Reference Example 1 (Production of Compound (3))

4.64 g (11.3 mmol) of the compound (1) (acetobromogalactose), 2.78 g (7.7 mmol) of HgBr₂, and 80 ml of dichloroethane were added to 12 g of activated Molecular Sieves 4A. The obtained mixture was agitated at room temperature in the presence of Ar. 20 ml of a dichloroethane solution containing 2.72 g (5 to 1 mmol) of the compound (2) was then added to this mixture and the temperature was gradually increased to 80° C., at which temperature the resulting mixture was agitated for 33 hours. The obtained reaction product was filtered by Celite and the filtrate was diluted with dichloroethane and then washed with saturated sodium bicarbonate water, water, and saturated salt water in this order. An organic layer was dried with MgSO₄ and the solvent was distilled off. The residue was purified by using a silica gel column (Wakogel C-300, 200 g; THF: n-hexane=4:6) to obtain 3.75 g of the compound (3) (yield, 85.5%).

Elementary analysis: $C_{45}H_{49}NO_{16}$: Theoretical values C 62.86 H 5.74 N 1.63. Measured values C 62.89 H 5.82 N 1.66.

Rf: 0.36 (THF n-hexane=4:6).

$[\alpha]_D^{20} +29.2°$ (C=1.00, CHCl₃).

NMR: CDCl₃, TMS: δH 1.974, 2.024, 2.026, 2.064 (4s, 12H, CH₃CO), 4.430 (d, J=12.21 Hz, 1H, benzyl), 4.506 (d, J=12.21 Hz, 1H, benzyl), 4.584 (d, J=8.0 Hz, H-1b), 5.130 (d, J=8.3 Hz, H-1a), 5.265 (d, J=3.4 Hz, H-4b), 5.623-5.719 (m, 1H, -CH=CH₂), δC 97.3 ('J$_{CH}$ 159.9, H-1a) 100.3 ('J$_{CH}$ 164.8, H-1b)

Reference Example 2 (Production of Compound (4))

2.0 ml of 0.1N CH₃ONa and 20.0 ml of CH₃OH were added to 1.3 g (1.5 mmol) of the compound (3) and the mixture was agitated at room temperature for 30 minutes. The mixture was then neutralized with Amberlite and filtered. The filtrate was concentrated under reduced pressure. 10 ml of acetonitrile, 360 ml (1.6 eq) of benzaldehyde dimethylacetal, and 10 mg of paratoluenesulfonic acid were added to the residue, and the resultant mixture was agitated at room temperature for 21.5 hours. The mixture was neutralized with triethylamine and then concentrated under reduced pressure. The residue was purified using a silica gel column (Wakogel C-300, 30 g; CHCl₃: CH₃OH=20:1) to obtain 1.17 g of the compound (4) (yield, 99.4%).

Elementary analysis: $C_{44}H_{45}NO_{12}$: ½H₂O: Theoretical values C 66.99 H 5.87 N 1.7. Measured value C 67.01 H 5.85 N 1.95.

Rf: 0.39 (CHCl₃: CH₃OH=20:1).

$[\alpha]_D^{21} +21.0°$ (C=1.03, CHCl₃)

NMR: CDCl₃, TMS δH 4.554 (d, J=12.5 Hz, 1H, benzyl), 4.566 (d, J=7.8 Hz, H-1b), 4.598 (d, J=12.5 Hz, 1H, benzyl), 4.769 (d, J=12.2 Hz, 1H, benzyl), 4.966 (d, J=12.4 Hz, 1H, benzyl), 5.144 (d, J=8.5 Hz, H-1a),

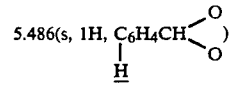

5.626-5.723 (m, 1H, —CH=CH₂), δC 97.5 ('J$_{CH}$ 159.9, H-1a), 101.3 ('JCH 159.9, H-1b),

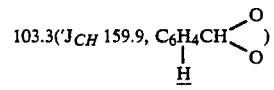

Reference Example 3 (Production of Compound (5))

0.1 ml of acetic anhydride and 0.2 ml of pyridine were added to 110 mg of (0.14 mmol) of the compound (4), and the mixture was agitated at room temperature for 3 hours. The solvent was then distilled off under reduced pressure and the residue was purified by using a silica gel column (Wakogel C-300, 2 g; ethyl acetate : hexane=1:1) to obtain 120 mg of the compound (5) (yield, 98.5%).

Elementary analysis: $C_{48}H_{49}NO_{14}$: Theoretical values C 65.37 H 5.82 N 1.59. Measured values C 65.29 H 5.64 N 1.68.

Rf: 0.46 (acetic acid : hexane=1:1)

$[\alpha]_D^{19} +38.0°$ (C=0.86, CHCl₃).

NMR: CDCl₃, TMS δH 2.044, 2.057 (2s, 6H, CH₃CO), 4.628 (d, J=8.2 Hz, H-1b), 4.513 (d, J=12.2 Hz, 1H, benzyl), 4.562 (d, J=12.2 Hz, 1H, benzyl), 4.812 (d, J=12.0 Hz, 1H, benzyl), 4.983 (d, J=12.4 Hz, 1H, benzyl), 5.134 (d, J=8.3 Hz, H-1a), 5.351 (d, d, J=7.9 Hz, H-2b),

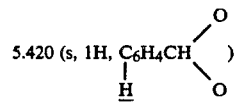

5.619-5.717 (m, 1H, —CH=CH₂).

Reference Example 4 (Production of Compound (6))

320 mg (8 mmol) was added little by little to 30 ml of dimethylformamide solution containing 1.04 g (1.3 mmol) of the compound (4) under agitation while cooling it by ice. 0.95 ml (8 mmol) of benzyl bromide was then dropwisely added to the mixture.

The resultant mixture was then agitated at room temperature for 5.5 hours and CH₃OH was added to the reaction solution so as to remove excess NaH. The reaction product was extracted with diethylether and the extract was washed with cold water and saturated salt water.

An organic layer was dried with MgSO₄ and the solvent was then distilled off under reduced pressure. The residue was purified by using a silica gel column (Wakogel C-300, 60 g; ethyl acetate:hexane=2:3) to obtain 0.84 g of the compound (6) (yield, 65.9%).

Elementary analysis: C₅₈H₅₇NO₁₂. Theoretical values C 72.56 H 5.98 N 1.46. Measured values C 72.16 H 6.04 N 1.17.

Rf: 0.27 (ethyl acetate:hexane=3:5)

[α]$_D^{20.5}$+16.9° (C=1.03, CHCl₃)

NMR: CDCl₃, TMS, δH 4.365 (d, J=12.9 Hz, 1H, benzyl), 4.477 (d, J=7.6 Hz, H-1b), 4.598 (d, J=12.2 Hz, 1H, benzyl), 4.639 (d, J=12.7 Hz, 1H, benzyl), 4.739 (s, 2H, benzyl), 4.826 (d, J=11.0 Hz, 1H, benzyl), 4.878 (d, J=11.0 Hz, 1H, benzyl), 5.109 (d, J=10.5 Hz, 1H, benzyl), 5.148 (d, J=8.5 Hz, H-1a),

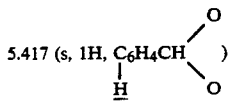

5.625-5.706 (m, 1H, —CH=CH₂)

Reference Example 5 (Production of Compound (7))

6.3 ml of 90% CF₃COOH was dropwisely added to 200 ml of a CH₂Cl₂ solution containing 5.5 g (5.73 mmol) of the compound (6) under agitation while cooling by ice. The mixture was agitated for 2 hours and then neutralized with 30 ml of triethylamine. The mixture was washed with saturated sodium bicarbonate water and an organic layer was then dried with MgSO₄.

The solvent was then distilled off under reduced pressure and the residue was purified by using a silica gel column (Wakogel C-300, 450 g; CHCl₃: CH₃OH 10:1) to obtain 4.3 g of the compound (7) (yield, 86.0%).

Elementary analysis: C₅₁H₅₃NO₁₂ 0.5H₂O: Theoretical values C 69.61 H 6.18 N 1.59. Measured values C 69.60 H 6.09 N 1.64.

Rf: 0.32 (CHCl₃: CH₃OH=20:1)

[α]$_D^{20.5}$+25.5° (C=1.0, CHCl₃)

NMR: CDCl₃, TMS δH 4.403 (d, J=12.0 Hz, 1H, benzyl), 4.419 (d, J=7.6 Hz, H-1b), 4.470 (d, J=12.2 Hz, 1H, benzyl), 4.606 (d, J=12.2 Hz, 1H, benzyl), 4.702 (s, 2H, benzyl), 4.808 (d, J=11.0 Hz, 1H, benzyl), 4.853 (d, J=13.9 Hz, 1H, benzyl), 4.885 (d, J=12.2 Hz, 1H, benzyl), 5.157 (d, J=8.6 Hz, H-1a), 5 657–5.685 (m, 1H, —CH=CH₂)

Reference Example 6 (Production of Compound (8))

1.5 ml of dichloroethane was added to 500 mg of activated Molecular Sieves 4A, 142 mg (0.392 mmol) of HgBr₂, 99 mg (0.392 mmol) of Hg(CN)₂, and 171 mg (0.196 mmol) of the compound (7) and the obtained mixture was agitated while cooling with ice in the presence of Ar. 2.0 ml of the dichloroethane solution was added to 200 mg (0.392 mmol) of the compound (a) and the resultant mixture was agitated at room temperature for 66 hours.

The reaction solution was then filtered by Celite and the filtrate was diluted with dichloroethane and then washed with saturated sodium bicarbonate water and saturated salt water. An organic layer was dried with MgSO₄ and the solvent was then distilled off under reduced pressure. The residue was purified by using a silica gel column (Wakogel C-300, 10 g; toluene: ethyl acetate: CH₃OH=10:10:1) to obtain 81 mg of the compound (8) (yield, 30.8%).

Elementary analysis: C₇₁H₈₀N₂O₂₄·H₂O: Theoretical values C 62.54 H 6.06 N 2.01. Measured values C 62.54 H 5.97 N 2.04.

Rf: 0.23 (ethyl acetate : toluene=2:1).

[α]$_D^{22}$+9.8° (C=1.0, CHCl₃).

NMR: CDCl₃, TMS δH 1.727, 1.861, 1.880, 2.033, 2.119, (5s, 15H, CH₃CO), 2.502 (dd, J=12.9, 5.0 Hz, H-3c eq), 4.466 (d, J=7.8 Hz, H-1b), 3.835 (s, 3H, COOCH₃), 5.119 (d, J=8.1 Hz, H-1a), 5.421 (m, 1H, H-4c), 5.491 (d, J=9.3 Hz, 1H, NHCOCH₃),

Reference Example 7 (Production of Compound (9))

ml of acetic anhydride, 1 ml of pyridine, and 5 mg of 4-dimethylaminopyridine were added to 24 mg (0.018 mmol) of the compound (8), and the mixture was agitated at room temperature for 12 hours.

The solvent was then distilled off under reduced pressure and the residue was purified by using a silica gel column (Wakogel C-300, 3 g; toluene: ethyl acetate: CH₃OH=1) to obtain 24 mg of the compound (9) (yield, 1 Elementary analysis: C₇₃H₈₂N₂O₂₅: Theoretical values C 63.20 H 5.96 N 2.02. Measured values C 63.50 H 5.89 N 2.19.

Rf: 0.35 (ethyl acetate: toluene=3:1), [α]$_D^{19}$+9.4° (C=0.84, CHCl₃)

NMR: CDCl₃, TMS δH 1.782, 1.880, 1.904, 2.037, 2.144, 2.236 (6s, 18H, CH₃CO), 2.516 (dd, J=12.9, 5.0 Hz, H-3c eq), 3.878 (s, 3H, COOCH₃), 4.382 (d, J=12.2 Hz, 1H, benzyl), 4.489 (d, J=13.2 Hz, 1H, benzyl), 4.496 (d, J=7.6 Hz, H-1b), 4.550 (d, J=11.5 Hz, 1H, benzyl), 4.620 (d, J=12.2 Hz, 1H, benzyl), 4.721 (d, J=13.0 Hz, 1H, benzyl), 4.769 (d, J=11.7 Hz, 1H, benzyl), 4.783 (d, J=11.2 Hz, 1H, benzyl), 4.831 (d, J=11.3 Hz, 1H, benzyl), 5.123 (d, J=8.5 Hz, H-1a) , 5.344 (m, 1H, H-4c), 5.680 (d, J=3.2 Hz, H-4b), 5.931 (d, J=10.0 Hz, NHCOCH₃).

Reference Example 8 (Production of Compound (10))

1.0 ml of acetic anhydride, 0.8 ml of pyridine, and 13 mg (0.1 mmol) of 4-dimethylaminopyridine were added to 872 mg (1 mmol) of the compound (7), and the obtained mixture was agitated at room temperature for 3 hours.

The solvent was then distilled off under reduced pressure and the residue was purified by using a silica gel column (Wakogel C-300, 50 g; toluene : ethyl acetate=4:1) to obtain 901 mg of the compound (10) (yield, 94.2%).

Elementary analysis: C₅₅H₅₇NO₁₄: Theoretical values C 69.10 H 6.01 N 1.47. Measured values C 69.22 H 6.03 N 1.42.

Rf: 0.36 (toluene: ethyl acetate=4:1).

[α]$_D^{23}$+32.7° (C=0.98, CHCl₃).

NMR: CDCl₃, TMS δH 2.049, 2.054 (2s, 6H, CH₃CO), 4.383 (d, J=12.2 Hz, 1H, benzyl), 4.453 (d, J=7.8 Hz, H-1b), 4.484 (d, J=12.2 Hz, 1H, benzyl), 4.497 (d, J=11.2 Hz, 1H, benzyl), 4.623 (d, J=12.2 Hz, 1H, benzyl), 4.735 d, J=11.2 Hz, 1H, benzyl), 5.148 (d, J=8.5 Hz, H-1a), 5.394 (d, J=2.7 Hz, H-4b).

Reference Example 9 (Production of Compound (11))

15.7 mg (0.017 mmol) of (φ₃P)₃RhCl, 6.2 mg (0.055 mmol) of DABCO and 20 ml of C₂H₅OH-φ-H₂O (7:3:1) were added to mg (0.261 mmol) of the compound (10), and the obtained mixture was refluxed for 3 hours.

The solvent was then distilled off and 246 mg (0.91 mmol) of HgCl$_2$, 5.2 mg (0.024 mmol) of HgO, and 15 ml of 90% acetone were added to the residue, followed by agitation at room temperature for 18 hours. The obtained reaction product was diluted with CHCl$_3$ and washed with 10% KI. An organic layer was then dried with MgSO$_4$ and the solvent was distilled off under reduced pressure. The residue was purified by using a silica gel column (Wakogel C-300, 25 g; toluene ethyl acetate=3:2) to obtain 182 mg of the compound (1) in a ratio of β:α=2:1 (yield, 76.0%).

Elementary analysis: C$_{52}$H$_{53}$NO$_{14}$ ½H$_2$O: Theoretical values C 67.52 H 5.88 N 1.51. Measured values C 67.22 H 5.86 N 1.45.

Reference Example 10 (Production of Compound (12))

40.5 μl (0.39 mmol) of CCl$_3$CN and 18.6 μl (0.12 mmol) of DBU were continuously and dropwisely added to a mixed solution of 90.2 mg (0.099 mmol) of the compound (11) and 5 ml of CH$_2$Cl$_2$, under agitation while cooling by ice in the presence of Ar. The obtained mixture was then agitated at room temperature for 8 hours and the reaction solution was purified by using a silica gel column (Wakogel C-300, 20 g; toluene: ethyl acetate=5:1) to obtain the compound (12) comprising 49.4 mg of the β-type and 20.2 mg of the α-type (β-type: yield, 47.3%; α-type: yield, 19.3%).

β-Imidate

Rf=0.37 (toluene: ethyl acetate=5:1).
NMR: CDCl$_3$, TMS. δH 2.060, 2.071 (2s, 6H, Ac), 5.399 (d, J=2.7 Hz, H-4b), 6.395 (d, J=8.5 Hz, H-1a).

α-Imidate

Rf=0.26 (toluene: ethyl acetate=5:1).
NMR: CDCl$_3$, TMS. δH 2.027, 2.033 (2s, 6H, CH$_3$CO), 5.383 (d, J=3.4 Hz, H-4b), 6.376 (d, J=3.6 Hz, H-1a).

Reference Example 11 (Production of Compounds (13) and (14))

300 mg of Molecular Sieves AW300, 31.4 mg (0.036 mmol) of the compound (b), and 1 ml of dichloroethane were agitated at −25° C., and a mixed solution of 37.7 mg (0.036 mmol) of the compound (12) and dichloroethane was added to the obtained mixture. 5.5 μl of BF$_3$O(C$_2$H$_5$)$_2$ was then added to the resultant mixture, followed by agitation for 1.5 hours. The obtained reaction solution was filtered by Celite. The filtrate was diluted with dichloroethane and then washed with saturated sodium dicarbonate water and saturated salt water. An organic layer was then dried with MgSO$_4$ and the solvent was distilled off under reduced pressure. The residue was purified by using a silica gel column (Wakogel C-300, 7 g; toluene: ethyl acetate 4:1), to obtain 38.0 mg of a mixture (yield, 59.3%). It was found from 400 MHz NMR that the mixture comprised a compound in which a β-glycosidic linkage was formed at the 3-position (compound (13)) and a compound in which a β-glycosidic linkage was formed at the 4-position (compound (14)) in a ratio of about 1:1. 4 ml of pyridine and 4 ml of acetic acid were added to the mixture, followed by agitation at room temperature for one night. The solvent was then distilled off and the residue was purified by using a silica gel column (Wakogel C-300, 4 g; toluene: ethyl acetate=5:1) to obtain 17.5 mg of the compound (13) and 17.5 mg of the compound (14) (yield: compound (13), 23.0%; compound (14), 23.0%).

Compound (13)

Elementary analysis: C$_{108}$H$_{111}$NO$_{25}$: Theoretical values C 71.15 H 6.14 N 0.77. Measured values C 71.37 H 6.21 N 0.71.
Rf: 0.42 (toluene: ethyl acetate=5:1).
[α]$_D^{20}$+12.8° (C=0.13, CHCl$_3$).
NMR: CDCl$_3$, TMS δH 1.958, 2.003, 2.056 (3s, 9H, CH$_3$CO), 4.671 (dd, J=2.4, 10.2 Hz, H-3b), 5.058 (d, J=8.3 Hz, H-1c), 5.387 (d, J=4.4 Hz, H-4d).

Compound (14)

Elementary analysis: C$_{108}$H$_{111}$NO$_{25}$: Theoretical values C 71.15 H 6.14 N 0.77. Measured values C 70.87 H 6.00 N 0.56.
Rf: 0.31 (toluene: ethyl acetate=5:1)
[α]$_D^{20}$+6.5 (C=0.13, CHCl$_3$)
NMR: CDCl$_3$, TMS δH 2.037, 2.043, 2.048 (3s, 9H, CH$_3$CO), 5.272 (d, J=8.3 Hz, H-1c), 5.412 (d, J=4.0 Hz, H-4c or H-4d), 5.42 (d, J=4.0 Hz, H-4d or H-4b).

Reference Example (12) (Production of Compound (15))

3 g of Molecular Sieves AW300, 536 mg (55.1 mmol) of the compound (c), and 5 ml of dichloroethane were agitated at −20° C. in the presence of Ar. 5 ml of a mixed solution of 835 mg (78.7 mmol) of the compound (12) and dichloroethane was added to dropwisely to the obtained mixture. 135 μl (94.5 mmol) of BF$_3$O(C$_2$H$_5$)$_2$ was then added to the resultant mixture, followed by agitation for 1 hour. The obtained reaction solution was filtered by Celite and the filtrate was diluted with ethyl acetate and then washed with saturated sodium bicarbonate water and saturated salt water. An organic layer was then dried with MgSO$_4$ and the solvent was distilled off under reduced pressure. The residue was purified by using a silica gel column (Wakogel C-300, 80 g; n-hexane: ethyl acetate=2:1) to obtain 650 mg of a compound (15) (yield, 63.1%).

Elementary analysis: C$_{113}$H$_{115}$NO$_{24}$: Theoretical values C 72.54 H 6.20 N 0.75. Measured values C 72.44 H 6.10 N 0.66.
Rf: 0.35 (n-hexane : ethyl acetate=2:1).
[α]$_D^{23}$+1.1° (C=0.71, CHCl$_3$).
NMR: CDCl$_3$, TMS δH 2.015, 2.057 (2s, 6H, CH$_3$CO), 5.381 (d, J=8.6 Hz, H-1c), 5.410 (d, J=3.2 Hz, H-4d).

Reference Example 13 (Production of Compound (16))

10 ml of CH$_3$OH and 5.6 ml of 0.1N CH$_3$ONa were added to 530 mg (0.28 mmol) of the compound (15) and the mixture was agitated at room temperature for 30 minutes. The mixture was neutralized by using Amberlist 15 and then filtered. The filtrate was concentrated under reduced pressure. 5 ml of C$_2$H$_5$OH and 3 ml of H$_2$NNH$_2$ H$_2$O were added to the concentrated solution, followed by reflux for 3 hours. The solvent was then distilled off under reduced pressure and 5 ml of CH$_3$OH and 0.4 ml of (CH$_3$CO)$_2$O were added to residue, followed by agitation at room temperature for 2 hours. The insoluble substances were filtered off and the filtrate was concentrated under reduced pressure. The concentrated solution was purified by using a silica gel column (Wakogel C-300, 50 g; toluene: ethyl acetate=1:1) to obtain 330 mg of a compound (16) (yield, 68.6%).

Elementary analysis: $C_{103}H_{111}NO_{21}H_2O$: Theoretical values C 72.05 H 6.63 N 0.82. Measured values C 72.13 H 6.57 N 0.99.

Rf=0.43 (toluene: ethyl acetate=1:1)
$[\alpha]_D^{27}$+3.3 (C=1.0, CHCl$_3$).
NMR CDCl$_3$, TMS δH 1.420 (s, 3H, NHCOC$\underline{H}_3$)

Reference Example 14 (Production of Compounds (17) and (18))

150 mg of Molecular Sieves 4A, HgBr$_2$ (0.22 mmol), Hg(CN)$_2$ (0.055 mmol), and 0.5 ml of dichloroethane were added to 85 mg (0.05 mmol) of the compound (16) and the obtained mixture was agitated at room temperature for 1 hour in the presence of Ar. 0.5 ml of a dichloroethane solution containing 51 mg (0.10 mmol) of the compound (a) was then added to the mixture, followed by agitation at room temperature for 27 hours. The obtained reaction solution was filtered by using Celite and the filtrate was diluted with dichloromethane and washed with saturated sodium bicarbonate water and 10% KI. An organic layer was then dried with MgSO$_4$ and the solvent was distilled off under reduced pressure. The residue was purified by using a silica gel column (Wakogel C-300, 15 g; toluene: ethyl acetate: CH$_3$OH=10:10:1) to obtain 22.0 mg of Compound (17) and 13.3 mg of Compound (18) (Compound (17): yield, 20.3%; Compound (18): yield, 12.3%).

Compound (18)

Elementary analysis: $C_{123}H_{138}N_2O_{33}.4H_2O$: Theoretical values C 65.82 H 6.56 N 1.25. Measured values C 65.66 H 6.42 N 1.37.

Rf=0.30 (ethyl acetate: toluene=2:1).
$[\alpha]_D^{28}$−4.8° (C=0.86, CHCl$_3$).
NMR CDCl$_3$ TMS δH 1.416, 1.882, 1.949, 2.023, 2.083, 2.100 (6s, 18H, CH$_3$CO), 2.430 (dd, J=12.9, 4.6 Hz, H-3e eq), 3.752 (s, 3H, COOC$\underline{H}_3$), Compound (17)

Elementary analysis: $C_{123}H_{138}N_2O_{33}.H_2O$: Theoretical values C 67.45 H 6.44 N 1.28. Measured values C 67.24 H 6.50 N 1.36.

Rf=0.42 (ethyl acetate: toluene=2:1).
$[\alpha]_D^{28}$+1.4° (C=0.35, CHCl$_3$).
NMR CDCl$_3$, TMS δH 1.328, 1.657, 1.837, 1.949, 2.019, 1.125 (6s, 18H, CH$_3$CO), 2.518 (dd, J=13.0, 4.8 Hz, H-3e eq), 3.786 (s, 3H, COOC$\underline{H}_3$).

Reference Example 15 (Production of Compound (19))

10 mg (0.0046 mmol) of the compound (17), 0.2 ml of pyridine, and 0.2 ml of (CH$_3$CO)$_2$O were agitated at room temperature for 1 hour. The solvent was then distilled off and the residue was purified by using a silica gel column (Wakogel C-300, 1 g; ethyl acetate: toluene=2:1) to obtain a quantitative yield of Compound (19).

Elementary analysis: $C_{125}H_{140}N_2O_{34}$: Theoretical values C 67.80 H 6.37 N 1.27. Measured values C 68.00 H 6.21 N 1.31.

Rf=0.31 (ethyl acetate: toluene=2:1).
$[\alpha]_D^{23}$−7.2° (C=0.18, CHCl$_3$).
NMR CDCl$_3$, TMS δH 1.429, 1.874, 1.945, 2.013, 2.056, 2.080, 2.088 (7s, 21H, CH$_3$CO), 2.493 (dd, J=4.6, 13.0 Hz, H-3e eq), 3.737 (s, 3H, COOC$\underline{H}_3$), 5.506 (d, J=2.9 Hz, H-4d).

Reference Example 16 (Production of Compound (20))

10 mg (0.0046 mmol) of the compound (18), 0.2 ml of pyridine, and 0.2 ml of (CH$_3$CO)$_2$O were agitated at room temperature for 1 hour. The solvent was then distilled off and the residue was purified by using a silica gel column (Wakogel C-300, 1 g; ethyl acetate: toluene=2:1) to obtain a quantitative yield of Compound (20).

Rf=0.39 (ethyl acetate: toluene=2:1).
$[\alpha]_D^{23}$−10.8° (C=0.12, CHCl$_3$).
NMR CDCl$_3$, TMS δH 1.339, 1.884, 1.913, 1.942, 2.029, 2.156, 2.288, (7s, 21H, CH$_3$CO), 2.491 (dd, J=3.6, 12.6 Hz, H-3e eq), 3.789 (s, 3H, COOC$\underline{H}_3$), 5.693 (d, J=2.9 Hz, H-4d).

Reference Example 17 (Production of Compound (25))

6 ml of 30% aq CH$_3$OH and 120 mg of 10% Pd/C were added to 120 mg (0.055 mmol) of the compound (17), and the mixture was catalytically reduced. The catalyst was then filtered off and washed with 30% aq CH$_3$OH.

The solvent was then distilled off under reduced pressure and 1 ml of pyridine and 1 1ml of (CH$_3$CO)$_2$ were added to the residue, followed by agitation at room temperature for 6 hours. The solvent was distilled off under reduced pressure and the residue was purified by a silica gel column (Wakogel C-300, 7 g; CHCl$_3$: CH$_3$OH=15:1) to obtain 79 mg of Compound (25) (α:β=1:1) (yield, 85.0%).

Elementary analysis: $C_{70}H_{96}N_2O_{45}$ ½H$_2$O: Theoretical values C 49.62 H 5.77 N 1.65. Measured values C 49.45 H 5.60 N 1.88.

Rf=0.40 (CHCl$_3$: CH$_3$OH=15:1).
$[\alpha]_D^{23}$+4.9° (C=0.65, CHCl$_3$).
NMR CDCl$_3$, TMS δH 5.662 (d, J=8.3 Hz, H-1a β), 6.252 (d, J=3.7 Hz, H-1a α), 2.550 (dd, J=4.4, 12.9 Hz, H-3e eq), 3.800 (s, 3H, COOC$\underline{H}_3$).

Reference Example 18 (Production of Compound (21))

1.5 ml of 30% aq CH$_3$OH and 30 mg of 10% Pd/C were added to 30 mg (0.014 mmol) of the compound (18) and the mixture was catalytically reduced. The catalyst was filtered off and washed with 30% aq CH$_3$OH. The solvent was then distilled off under reduced pressure and 1 ml of pyridine and 1 ml of acetic anhydride were added to the residue, followed by agitation at room temperature for 12 hours. The solvent was distilled off under reduced pressure and the residue was purified by a silica gel column (Wakogel C-300, 2 g; CHCl$_3$: CH$_3$OH=15:1) to obtain 22 mg of a compound (21) (α:β=1:1) (yield, 94.5%).

Elementary analysis: $C_{70}H_{96}N_2O_{45}$ 3H$_2$O: Theoretical values C 48.33 H 5.91 N 1.61. Measured values C 48.05 H 5.51 N 1.68.

Rf=0.34 (CHCl$_3$: CH$_3$OH=15:1).
$[\alpha]_D^{23}$+9.7° (C=0.70, CHCl$_3$).
NMR CDCl$_3$, TMS δH 4.455 (dd, J=4.8, 12.9 Hz, H-3e, eq), 3.838 (s, 3H, COOCH$_3$), 5.659 (d, J=8.3 Hz, H-1a, β), 6.252 (d, J=3.7 Hz, H-1a, α).

Reference Example 19 (Production of Compound (26))

3.2 mg (0.035 mmol) of H$_2$NNH$_2$ CH$_3$CO and 1 ml of DMF were added to 46 mg (0.027 mmol) of the compound (25) and the obtained mixture was agitated at 50° C. for 30 minutes.

The mixture was diluted with CHCl$_3$ and then washed with saturated salt water. An organic layer was dried with MgSO$_4$ and the solvent was distilled off. The residue was purified by using a silica gel column (Wakogel C-300, 5 g; CHCl$_3$: CH$_3$OH = 10:1) to obtain 28.0 mg of a compound (26) (yield, 62.5%).

Elementary analysis: C$_{68}$H$_{94}$N$_2$O$_{44}$: Theoretical values C 49.70 H 5.77 N 1.70. Measured values C 50.31 H 5.85 N 1.76.

Rf=0.43, 0.47 (CHCl$_3$: CH$_3$OH = 10:1).

[α]$_D^{23}$ +10.9° (C=0.74, CHCl$_3$).

NMR CDCl$_3$, TMS δH 2.548 (dd, J=4.4, 12.9 Hz, H-3e, eq), 3.800 (s, 3H, COOCH$_3$).

Example 1 (Production of Compound (27))

1.0 mg (0.007 mmol) of K$_2$CO$_3$ and 0.5 ml of CH$_3$OH were added to 3.2 mg (0.0019 mmol) of the compound (26) and the mixture was agitated at room temperature for 1 hour.

The mixture was neutralized with Amberlist 15 and the solvent was then distilled off. 0.3 ml of 0.01N NaOH was added to the residue, followed by agitation at room temperature for 1 hour.

The reaction solution was treated with Sephadex G-25 to obtain 1.7 mg of Compound (27) (yield, 87.7%).

Rf=0.31 (nC$_3$H$_7$OH: C$_2$H$_5$OH: H$_2$O = 2:1:2)

| NMR | D$_2$O, acetone 60° C. | |
|---|---|---|
| | 1.719 (t, 1H, J=2.1 Hz, H-3e ax) | |
| | 2.022 (s, NHAc) | |
| | 2.049 (s, NHAc) | |
| | 2.665 (dd, J=4.4, 12.6 Hz, H-3e eq) | |
| | 4.153 (d, J=2.7 Hz, 1H, α) | |
| | 4.469 (d, J=8.8 Hz, 2H, 2β) | |
| | 4.669 (d, J=8.0 Hz, 1H, α) | |
| | 4.773 (d, J=8.0 Hz, β) | H-1a |
| | 5.231 (d, J=2.9 Hz, α) | |

Reference Example 20 (Production of Compound (28))

16 μl (0.15 mmol) of CCl$_3$CN and 5 μl (0.03 mol) of DBU were added to 0.5 ml of a C$_2$H$_4$Cl$_2$ solution of 25 mg (0.015 mmol) of the compound (26) in this order in the presence of Ar under agitation while cooling by ice. After agitation for 4 hours, the reaction solution was purified by column chromatography (Wakogel C-300, 3 g; CHCl$_3$: MeOH = 15:1), to obtain 26.3 mg of Compound (28) (yield, 96.7%).

Rf=0.36 (CHCl$_3$: CH$_3$OH = 15:1).

NMR CDCl$_3$, TMS δH 1.543 (s, 3H, NHCOCH$_3$), 1.893, 1.919, 1.954, 2.008, 2.030, 2.040, 2.052, 2.078, 2.116, 2.118, 2.122, 2.144, 2.149, 2.169, 2.176 (15s, 45H, CH$_3$CO), 2.549 (dd, J=4.5, 12.7 Hz), 3.800 (s, 3H, COOCH$_3$), 4.378 (d, J=7.8 Hz), 4.584 (d, J=7.8 Hz), 4.654 (d, J=8 Hz), 4.864 (m, H-4e), 6.481 (d, J=3.9 Hz, H-1a), 8.650 (s, NH).

Reference Example 21 (Production of Compound (29))

17.9 mg (0.020 mmol) of the compound (d) and 0.5 ml of C$_2$H$_4$Cl$_2$ were added to 600 mg of Molecular Sieves AW300 and the mixture was agitated at −20° C. 0.5 ml of a mixed solution of 24.0 mg (0.0134 mmol) of the compound (28) and C$_2$H$_4$Cl$_2$ was the resultant mixture. 3.4 μl (0.0201 mmol) of BF$_3$O(C$_2$H$_5$)$_2$ was then added to the obtained mixture, followed by agitation for 1 hour. The obtained reaction product was diluted with CHCl$_3$ and then washed with saturated sodium bicarbonate water and saturated salt water. An organic layer was dried with MgSO$_4$ and the solvent was distilled off. The residue was purified by using a silica gel column (Wakogel C-300, 3 g; toluene acetone = 1:1) to obtain 6.5 mg of Compound (29) (yield, 19.3%) and recover 13.0 mg of the compound (d) (72.6%).

Rf=0.41 (toluene: acetone=4:1).

[α]$_D^{24}$ −10.0° (C=0.18, CHCl$_3$).

NMR CDCl$_3$, TMS δH 0.881 (t, 6H, J=6.4 Hz) 1.000 (s, 9H, tC$_3$H$_7$), 1.223 (s, NHCOCH$_3$), 1.914, 1.954, 1.959, 2.022, 2.030, 2.040, 2.048, 2.052, 2.077, 2.079, 2.122, 2.144, 2.149, 2.169 (15s, 48H, CH$_3$CO), 2.548 (dd, J=4.8, 13.1 Hz, H-3e eq), 3.800 (d, 3H, COOCH$_3$), 4.318 (d, J=7.5 Hz), 4.412 (d, J=8.1 Hz), 4.582 (d, J=7.8 Hz), 4.650 (d, J=8.3 Hz), 7.286-7.677 (m, 10H, Ar).

Example 2 (Production of Compound (30))

16 μl of nBu$_4$NF (1M THF So/n) and 0.3 ml of THF were added to 3.3 mg (0.0013 mmol) of the compound (29) and the mixture was agitated at room temperature for 3 hours. The solvent was distilled off and 0.3 ml of CH$_3$OH, 0.3 ml of THF, and 0.2 ml of 0.1N CH$_3$ONa were added to the residue, followed by agitation at room temperature for 2.5 hours. The mixture was neutralized with Amberlist 15 and the solvent was then distilled off. 0.3 ml of 0.01N NaOH was then added to the residue, followed by agitation at room temperature for one night. The reaction solution was purified by using Sephadex LH-20 (CHCl$_3$: MeOH: H$_2$O = 60:30:4.6) to obtain 1.6 mg of Compound (30) (yield, 74.8%).

Rf=0.48 (nC$_3$H$_7$OH: C$_2$H$_5$OH: H$_2$O = 2:1:1).

NMR DMSOd$_6$, t-BuOH, 1.826, 1.877 (s, NHAc×2), 4.163 (d, J=6.8 Hz, β), 4.215 (d, J=7.0 Hz, β), 4.256 (d, J=7.6 Hz, β), 4.676 (d, J=7.6 Hz, β), 5.336 (d, 1H), 5.519 (m, 1H).

Reference Example 22 (Production of Compound (22))

1.4 mg (0.015 mmol) of H$_2$NNH$_2$—CH$_3$CO and 0.5 ml of DMF were added to 18 mg (0.011 mmol) of the compound (21) and the mixture was agitated at 50° C. for 30 minutes.

The mixture was then diluted with CHCl$_3$ and washed with saturated salt water. An organic layer was dried with MgSO$_4$ and the solvent was then distilled off. The residue was purified by using a silica gel column (Wakogel C-300, 2 g; CHCl$_3$ CH$_3$OH 10:1) to obtain 15 mg of Compound (22) (yield, 85.5%).

Elementary analysis: C$_{68}$H$_{94}$N$_2$O$_{44}$ H$_2$O: Theoretical values C 49.16 H 5.82 N 1.69. Measured values C 49.21 H 5.70 N 2.07.

Rf=0.47 (CHCl$_3$: CH$_3$OH = 10:1).

[α]$_D^{23}$ +4.9° (C=0.45, CHCl$_3$).

NMR CDCl$_3$, TMS, δH 2.457 (dd, J=4.9, 13.0 Hz, H-3e eq), 3.838 (s, 3H, COOCH$_3$).

Reference Example 23 Production of Compound (23))

6 ml of 30% aq CH$_3$OH and 110 mg of 10% Pd/C were added to 110 mg (0.065 mmol) of the compound (16) and the mixture was catalytically reduced. The catalyst was then filtered off and washed with 30% aq CH$_3$OH and the solvent was then distilled off. 2 ml of pyridine and 2 ml of (CH$_3$CO)$_2$O were added to the residue, followed by agitation at room temperature for one night. The solvent was then distilled off and the residue was purified by using a silica gel column (Wakogel C-300, 5 g; CHCl$_3$: CH$_3$OH = 20:1) to obtain 66 mg of Compound (23) (yield, 81.3%).

Elementary analysis: $C_{52}H_{71}NO_{34} \cdot \frac{1}{2}H_2O$, Theoretical values C 49.45 H 5.75 N 1.11, Measured values C 49.26 H 5.68 N 1.21.

Rf=0.37 (CHCl$_3$: CH$_3$OH=20:1). $[\alpha]_D^{25}+28.6$ (C=0.86, CHCl$_3$).

NMR CDCl$_3$, TMS $\delta$H 5.664 (d, J=8.3 Hz, H-1a $\beta$), 6.253 (d, J=3.9 Hz, H-1a $\alpha$).

Reference Example 24 (Production of Compound (24))

6 mg (0.032 mmol) of H$_2$NNH$_2$ CH$_3$COOH and 1 ml of DMF were added to 20 mg (0.016 mmol) of the compound (23) and the mixture was agitated at 50° C. for 45 minutes.

The mixture was diluted with CHCl$_3$ and washed with saturated salt water and an organic layer was then dried with MgSO$_4$.

The solvent was then distilled off and the residue was purified by a silica gel column (Wakogel C-300, 2 g; CHCl$_3$: CH$_3$OH=20:1) to obtain 16 mg of Compound (24) (yield, 82.8%).

Elementary analysis: $C_{50}H_{69}NO_{33}$: Theoretical values C 49.55 H 5.74 N 1.16. Measured values C 49.45 H 5.69 N 2.27.

Rf=0.37 (CHCl$_3$: CH$_3$OH=15.1), +32.6° (C=0.38, CHCl$_3$).

Reference Example 25 (Production of Compound (31))

0.5 ml of C$_2$H$_4$Cl$_2$ was added to 11.5 mg (0.0095 mmol) of the compound (24) and the mixture was agitated under ice cooling in the presence of Ar. 10 $\mu$l (0.095 mmol) of CCl$_3$CN and 3 $\mu$l (0.019 mmol) of DBU were added in turn to the mixture, followed by agitation for 4 hours. The reaction product was purified by column chromatography (Wakogel C-300, 2 g; CHCl$_3$: CH$_3$OH=15:1) to obtain 12.6 mg of a compound (31) (yield, 97.9%), Rf=0.46 (CHCl$_3$: CH$_3$OH=10:1).

NMR CDCl$_3$, TMS, $\delta$H 4.375 (d, J=8.1 Hz), 4.547 (d, J=8.1 Hz), 4.672 (d, J=8.1 Hz), 6.482 (d, J=3.6 Hz, H-1a),

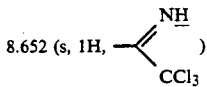

Reference Example 26 (Production of Compound (32))

9.8 mg (0.011 mmol) of the compound (d) and 0.3 ml C$_2$H$_4$Cl$_2$ were added to 300 mg of Molecular Sieves AW300 and 0.3 ml of a mixed solution of 10 mg (0.0074 mmol) of the compound (31) and C$_2$H$_4$Cl$_2$ was then added to the mixture under agitation at −20° C. 1.5 $\mu$l (0.0089 mmol) of BF$_3$O(C$_2$H$_5$)$_2$ was then added to the resultant mixture, followed by agitation 5 hours. The mixture was diluted with CHCl$_3$ and then filtered and the filtrate was washed with saturated sodium bicarbonate water and saturated salt water. An organic layer was dried with MgSO$_4$ and the solvent was distilled off. The residue was purified by a silica gel column (Wakogel C-300, 1 g; toluene: acetone=2:1) to obtain 3.0 mg of Compound (32) (yield, 15.4%) and recover 7.8 mg of the silylceramide 1 (79.6%). Rf=0.40 (toluene: acetone=3:2)

NMR CDCl$_3$, TMS, $\delta$H 0.879 (t, 6H, J=6.8 Hz), 1.002 (s, 9H, tC$_3$H$_7$), 1.224 (s, 3H, NH$_3$CO), 1.253 (br-s, 68H), 1.910, 1.960, 1.973, 2.023, 2.047, 2.050, 2.057, 2.062, 2.069, 2.073, 2.125, 2.152, 2.155 (13s, 39H, CH$_3$CO), 4.315 (d, J=8.1 Hz), 4.412 (d, J=7.8 Hz), 4.527 (d, J=7.1 Hz), 4.667 (d, J=7.8 Hz), 7.31–7.68 (m, 10H, Ar).

Example 3 (Production of Compound (33))

16 $\mu$l of nC$_3$H$_7$NF (1M THF So/n) and 0.1 ml of THF were added to 1.6 mg (0.0007 mmol) of the compound (32) and the mixture was agitated at room temperature for 2 hours. The solvent was then distilled off and 0.1 ml of CH$_3$OH, 0.1 ml of THF and 0.2 ml of 0.1N CH$_3$ONa were added to the residue, followed by agitation at room temperature for 2 hours. The mixture was neutralized with Amberlist 15 and the solvent was then distilled off. 0.3 ml of 0.01 N NaOH was added to the residue and the resultant mixture was agitated at room temperature for one night. The reaction product was purified by using Sephadex LH-20 (CHCl$_3$: CH$_3$OH: H$_2$O=60:30:4.6) to obtain 0.8 mg of Compound (33) (yield, 77.7%). Rf=0.35 (nC$_3$H$_7$OH: C$_2$H$_5$OH: H$_2$O=4:2:1).

400MHz NMR DMSOd6, t-BuOH, 1.814 (s, 3H, NHAc), 4.167 (d, 1H, J=7.8 Hz, $\beta$), 4.192 (d, 1H, J=7.0 Hz, $\beta$), 4.248 (d, 1H, J=7.1 Hz, $\beta$), 4.635 (d, 1H, J=8.5 Hz, $\beta$).

(D) As for Ganglioside GD$_{1a}$ related compounds (The compound alphabets or numbers used in the following comparative examples and examples correspond to those used in Scheme IX):

Reference Example 1 (Production of Compounds (B) and (C))

700 mg (2.0 mmol) of the compound (A) was dissolved in 5 ml of acetone and 288 mg of 2,2-dimethoxypropane and 40 mg of p-toluenesulfonic acid were added to the acetone solution, followed by agitation at room temperature for 2 hours. 0.5 ml of 1.7 ethylamine was then added to the resultant mixture and the reaction solution was then concentrated under reduced pressure. The residue was purified by column chromatography using 40 g of silica gel (chloroform methanol triethylamine=97:3:0.2), to obtain 664 mg of a mixture of 3,4- and 4,5-isopropylidenated compounds (yield, 85%). In this case, the mixture was benzylated without being isolated. 650 mg (1.67 mmol) of the obtained mixture was dissolved in 10 ml of DMF, and then 87 mg (60%) of NaH and 371 mg of benzyl bromide were added to the DMF solution, followed by agitation at room temperature for 2 hours. The reaction solution was cooled with ice and NaH and 185 mg of benzyl bromide were then added to the solution, followed by agitation at room temperature for 5 hours. 1 ml of methanol was added to the reaction solution under cooling by ice and the resulting mixture was concentrated under reduced pressure. The residue was dissolved in ethyl acetate, then washed with water, and dried with MgSO$_4$. The resultant solution was concentrated under reduced pressure and the residue was purified by column chromatography using 60 g of silica gel (toluene ethyl acetate=9:1), to obtain 365 mg of the compound (B) and 198 mg of the compound (C) (yield: compound (B), 46%, compound (C), 25%).

Compound (B)

$[\alpha]_D^{21}+14.6$ (C=1.0, CHCl$_3$).

Rf=0.38 (toluene: ethyl acetate=9:1).

$^1$HNMR (CDCl$_3$)

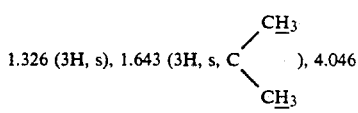

1.326 (3H, s), 1.643 (3H, s, C), 4.046

(1H, dd, J=6.4, 13.2 Hz, —CH$_2$—CH=CH$_2$), 4.147 (1H, m, H-5), 4.251 (1H, dd, J=1.7, 4.6 Hz, H-4), 4.316 (1H, t, J=9.0 Hz, H-2), 4.607 (1H, d, J=12.0 Hz, —CH$_2$Ph), 4.684 (1H, d, J=12.0 Hz, —CH$_2$Ph), 4.790 (1H, dd, J=5.1, 9.3 Hz, H-3), 5.048 (1H, dd, J=1.5, 10.5 Hz, —CH=CH$_2$), 5.119 (1H, d, J=8.8 Hz, H-1), 5.120 (1H, dd, J=1.5, 17.1 Hz, —CH=CH$_2$), 5.725 (1H, m, —CH=CH$_2$), 7.361-7.728 (4H, m, aromatic protons)

Compound (C)

$[\alpha]_D^{21}$+39.0 (C=1.08, CHCl$_3$).
Rf=0.15 (toluene: ethyl acetate=9:1).
$^1$HNMR (CDCl$_3$)

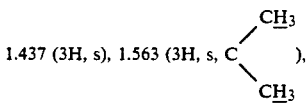

1.437 (3H, s), 1.563 (3H, s, C), 4.426 (1H, d, J=12.5 Hz, —CH$_2$Ph), 4.570 (1H, d, J=12.5 Hz, —CH$_2$Ph), 4.651 (1H, t, J=8.5 Hz, H-2), 5.147 (1H, d, J=8.6 Hz, H-1), 5.687 (1H, m, —CH=CH$_2$), 7.084 -7.719 (4H, m, aromatic protons).

Elementary analysis C$_{27}$H$_{29}$NO$_7$. Theoretical values C 67.63 H 6.10 N 2.92. Measured values C 67.48 H 6.10 N 2.60.

Reference Example 2 (Production of Compound (D))

341 mg (0.71 mmol) of the compound (B) was dissolved in 10 ml of 10% aqueous acetic acid solution and the resulting solution was agitated at 50° C. for 12 hours and then concentrated under reduced pressure. The residue was purified by column chromatography using 12 g of silica gel (toluene: ethyl acetate=4:6) to obtain 289 mg of the compound (D) (yield, 92%).

Rf=0.24 (toluene: ethyl acetate=1:1)
$^1$HNMR (CDCl$_3$), 4.60 (2H, s, —CH$_2$Ph), 5.68 (1H, m, —CH=CH$_2$), 7.18-7.80 (9H, m, aromatic protons).

Elementary analysis C$_{24}$H$_{25}$NO$_7$: Theoretical values C 65.59 H 5.73 N 3.19. Measured values C 65.52 H 5.75 N 3.06.

Reference Example 3 (Production of Compounds (E) and (F))

568 mg (1.3 mmol) of the compound (D) was dissolved in 5 ml of acetonitrile and 296 mg (1.9 mmol) of benzaldehyde dimethylacetal and 25 mg (a catalytic amount) of paratoluenesulfonic acid were added to the solution, followed by agitation for 12 hours. The obtained reaction solution was concentrated to about a half volume under reduced pressure, and 150 mg of benzaldehyde dimethylacetal and 2 ml of acetonitrile were added to the concentrated solution, followed by agitation for 1 hour. 0.1 ml of triethylamine was added to the reaction solution and the mixture was concentrated under reduced pressure. The residue was dissolved in ethyl acetate, washed with saturated salt water, and then dried with MgSO$_4$. The resultant solution was concentrated under reduced pressure and the residue was purified by silica gel column chromatography (SiO$_2$, 50 g; toluene ethyl acetate triethylamine=94:5:1) to obtain 263 mg of the compound (E) and 265 mg of the compound (F) (yield, 38.6%).

Compound (E) (yield, 38.6%)

$[\alpha]_D^{27}$+21.3 (C=0.61, CHCl$_3$).
Rf=0.43 (toluene: ethyl acetate=1:1).
Elementary analysis C$_{31}$H$_{29}$NO$_7$: Theoretical values C 70.57 H 5.54 N 2.66. Measured values C 71.35 H 5.62 N 2.47.
$^1$HNMR CDCl$_3$, TMS ppm 3.898 (2H, d, J=5.9, H-6), 4.128 (1H, d, t, J=1.7, 6.6 Hz, H-5), 4.297 (1H, dd, J=1.7, 5.1 Hz, H-4), 4.454 (1H, t, J=8.8 Hz, H-2), 4.581 (1H, d, J=12.0 Hz), 4.659 (1H, d, J=11.7 Hz, —CH$_2$Ph), 5.097 (1H, dd, J=4.5, 9.3 Hz, H-3), 5.182 (1H, d, J=8.8 Hz, H-1), 6.311

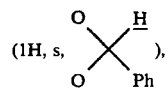

7.157-7.869 (9H, m, aromatic protons)
$^{13}$CNMR CDCl$_3$ ppm 52.4 (C-2), 97.0 (C-1),

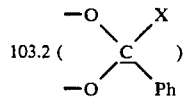

103.2 ( )

Compound (F) (yield, 38%)

$[\alpha]_D^{26}$+71.4 (C=0.96, CHCl$_3$).
Rf=0.43 (toluene: ethyl acetate=1:1).
Elementary analysis C$_{31}$H$_{29}$NO$_7$: Theoretical values C 70.57 H 5.54 N 2.66. Measured values C 70.57 H 5.56 N 2.55.
$^1$HNMR CDCl$_3$, TMS ppm 3.878 (1H, dd, J=6.6, 10.0 Hz, H-6), 3.949 (1H, dd, J=5.4, 10.0 Hz, H-6), 4.228 (1H, m, H-5), 4.336 (1H, dd, J=2.2, 5.6 Hz, H-4), 4.432 (1H, t, J=8.8 Hz, H-2), 4.598 (1H, d, J=12.0), 4.662 (1H, d, J=12.0 Hz, benzyl protons), 5.001 (1H, dd, J=5.6, 8.6 Hz, H-3), 5.168 (1H, d, J=8.8 Hz, H-1), 5.892

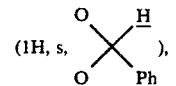

7.179-7.837 (9H, m, aromatic protons)
$^{13}$CNMR CDCl$_3$ ppm 55.9 (C-2), 97.2 (C-1),

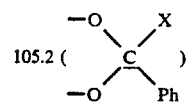

105.2 ( )

Reference Example 4 (Production of Compound (G))

218 mg (0.41 mmol) of the compound (F) was dissolved in 5 ml of THF and 550 mg (4.13 mmol) of aluminum chloride and 301 mg (4.13 mmol) of a BH$_3$ TMA complex were added to the THF solution, followed by agitation at room temperature for 1 hour. The reaction solution was diluted with ethyl acetate and washed with distilled water and sat. NaCl. The solution was dried with MgSO$_4$ and then concentrated under reduced pressure. When the residue was purified by silica gel column chromatography, 153 mg of the compound (G) was eluted with an eluent (toluene: ethyl acetate=9:1) (yield, 77%).

Compound (G)

$[\alpha]_D^{22} + 18.50$ (C=0.93, CHCl$_3$).
Rf=0.36 (ethyl acetate: toluene=1:4).
$^1$HNMR CDCl$_3$, TMS, ppm, 3.176 (1H, dd, J=5.9, 9.0 Hz, H-6), 3.854 (1H, t, J=7.8, H-5), 3.971 (1H, d, J=1.7 Hz), 4.339 (1H, d, J=8.3 Hz, H-1), 3.777 (1H, t, J=9.0 Hz, H-2), 4.540 (1H, d, J=12.0 Hz), 4.586 (1H, d, J=11.7 Hz), 4.611 (1H, d, J=12.0 Hz), 4.796 (1H, d, J=11.7 Hz, benzoyl protons), 5.220 (1H, dd, J=2.2, 6.3 Hz, H-3), 7.281–7.816 (14H, m, aromatic protons).
$^{13}$CNMR CDCl$_3$ 55.3 (C-2), 97.6 (C-1), 168.5 (C=0).

Reference Example 5 (Production of Compound (H))

44 mg (0.083 mmol) of the compound (G) was dissolved in a mixed solvent of 0.5 ml of acetic anhydride and 0.5 ml of pyridine, and the obtained mixture was agitated at room temperature for 12 hours. The obtained reaction solution was concentrated under reduced pressure, and the residue was purified by silica gel column chromatography, to obtain 4 mg of the Compound (H) in a 98% yield (SiO$_2$, 8.0 g; toluene: ethyl acetate=9:1).

Compound (H)

$[\alpha]_D^{21} + 14.0$ (C=1.2, CHCl$_3$)
Rf=0.34 (toluene: ethyl acetate=9:1)
Elementary analysis C$_{33}$H$_{33}$NO$_8$: Theoretical values C 69.34 H 5.82 N 2.45. Measured values C 68.99 H 5.85 N 2.52.
$^1$HNMR CDCl$_3$, TMS, ppm, 3.895 (1H, t, J=6.8 Hz, H-5), 4.108 (1H, d, J=2.9 Hz, H-4), 4.464 (1H, d, J=12.0 Hz, benzoyl protons), 4.525 (1H, d, J=12.0 Hz, benzoyl protons), 4.561 (1H, d, J=11.7 Hz, benzoyl protons), 4.713 (1H, d, J=11.7 Hz, benzoyl protons), 4.761 (1H, dd, J=8.3, 11.2 Hz, H-2), 5.311 (1H, d, J=8.6 Hz, H-1), 5.689 (1H, dd, J=3.2, 11.2 Hz, H-3), 7.260–7.841 (14H, m, aromatic protons)

Reference Example 6 (Production of Compounds (J) and (K))

4 ml of dichloroethane containing 650 mg (1.23 mmol) of the compound (G) and 940 mg (1.02 mmol) of the compound (I) was added to 2.0 g of activated Molecular Sieves AW300 and 151 µl (1.23 mmol) of BF$_3$.Et$_2$O was then added to the mixture under cooling with ice in the presence of Ar, followed by agitation for 3 hours. After agitation at room temperature for 12 hours, insolubles were filtered off by Celite and then washed with ethyl acetate. The washing solution was mixed with the filtrate and the resultant mixture was washed with saturated sodium bicarbonate water and saturated salt water and dried with MgSO$_4$. The mixture was concentrated under reduced pressure and the residue was purified by silica gel column chromatography (SiO$_2$, 60 g; CH$_3$CN: CCl$_4$=3:7) to obtain 493 mg of a β-compound (compound (J)) and 127 mg α-compound (compound (K)) (yield: compound (J), 9.7%; compound (K), 38%).

β-compound (J)

Rf=0.42 (ethyl acetate) HPTLC
$[\alpha]_D^{23} - 1.0$ (C=0.62, CHCl$_3$)

Elemental analysis C$_{63}$H$_{74}$N$_2$O$_{27}$: Theoretical values C 58.60 H 5.73 N 2.17. Measured values C 57.97 H 5.70 N 2.21.
$^1$HNMR CDCl$_3$, TMS, ppm, 1.511 (1H, t, J=12.7 Hz, H-3 cax), 1.711 (3H, s), 1.880 (3H, s), 1.953 (3H, s), 1.974 (3H, s), 1.979 (3H, s), 2.032 (3H, s), 2.123 (3H, s), 2.139 (3H, s, COCH$_3$), 3.759 (3H, s, OCH$_3$), 7.25–7.88 (14H, m, aromatic protons).
$^{13}$CNMR CDCl$_3$, ppm. 21.5 (OCOCH$_3$), 21.9 (OCOCH$_3$), 24.5 (NHCOCH$_3$), 37.8 (C-3c), 49.7 (OCH$_3$), 52.8 (C-5c), 53.0 (C-2a), 97.7 (C-1b), 98.7 (C-1a).

α-compound (K)

Rf=0.30 (EtOAc) HPTLC
$[\alpha]_D^{25} + 1.2$ (C=0.95, CHCl$_3$)
Elementary analysis C$_{63}$H$_{74}$N$_2$O$_{27}$: Theoretical values C 58.60 H 5.73 N 2.17. Measured values C 58.21 H 5.72 N 2.13.
$^1$HNMR CDCl$_3$, TMS, ppm, 1.524, 1.816, 1.901, 1.929, 1.974, 2.057, 2.147, 2.161 (each, 3H, s, COCH$_3$), 2.510 (1H, dd, J=4.6, 12.7 Hz, H-3c), 3.828 (3H, s, OCH$_3$), 4.064 (1H, d, J=2.2 Hz, H-4a), 4.816 (1H, m, H-4c), 4.967 (1H, d, J=1.7 Hz, H-4b), 5.171 (1H, m, H-8c), 7.223–7.902 (14H, m, aromatic protons).
$^{13}$CNMR CDCl$_3$, 96.9 (C-2c), 97.7 (C-1a, $^1$JCH 160.5 Hz), 101.7 (C-1b, $^1$JCH 162.6 Hz).

Reference Example 7 (Production of Compound (L))

117 mg (0.091 mmol) of the compound (J) was dissolved in 11 ml of a mixed solvent (C$_2$H$_5$: benzene: H$_2$O=7:3:1), and 19 mg of tris(triphenylphosphine)rhodium (I) chloride and 3.2 mg of DABCO (2,2,2-diazabicyclooctane) were added to the resulting solution, followed by heat reflux for 22 hours in the presence of argon. The reaction solution was concentrated under reduced pressure and the residue was dissolved in 10 ml of acetone-water (9:1). 6 mg of mercury oxide and 87 mg of mercury (II) chloride were added to the obtained solution, followed by agitation for 1 hour. The resultant mixture was concentrated under reduced pressure and the residue was dissolved in ethyl acetate, washed with water, and then dried with MgSO$_4$.

The reaction product was purified by silica gel column chromatography (SiO$_2$, 12 g; ethyl acetate) to obtain 100 mg of the compound (L) (yield, 85%).

Compound (L)

Rf=0.19 (ethyl acetate) HPTLC.
$[\alpha]_D^{20} + 13.6$ (CHCl$_3$, C=1.09).
$^1$HNMR CDCl$_3$, TMS, 90 MHz: 1.76, 1.82, 1.90, 1.94, 1.99, 2.06, 2.16, 2.18 (each, 3H, s, COCH$_3$), 2.52 (1H, dd, J=4.4, 11.0 Hz, H-3c), 3.84 (3H, s, OCH$_3$), 7.30 7.86 (14H, m, aromatic protons).

Reference Example 8 (Production of Compound (1))

100 mg (0.080 mmol) of the compound (L) was dissolved in 2 ml of methylene chloride and 45 µl of trichloroacetonitrile and 15 µl of DBU were added to the obtained solution under cooling with ice in the presence of argon, followed by agitation for 2 hours. The mixture was purified by column chromatography using 10 g of silica gel and ethyl acetate as an eluent to obtain 75 mg of the compound (1) (yield, 67%).

Compound (1)

Rf=0.23 (ethyl acetate) HPTLC.

¹HNMR CDCl₃, 90 MHz, TMS, ppm, 1.56, 1.82, 1.88, 1.91, 1.94, 1.98, 2.15, 2.16, 2.18 (s, COCH₃), 2.56 (1H, m, H-3 ceq), 3.83 (1.8H, s, OCH₃), 3.85 (1.2H, s, OCH₃), 6.30 (0.6H, d, J=7.2 Hz, H-1aβ), 6.38 (0.4H, d, J=3.0 Hz, H-1aα), 7.28–7.88 (14H, m, aromatic protons).

Example 1 Production of Compound (3))

1 ml of a dichloroethane solution containing 75 mg (0.053 mmol) of the compound (1) and 150 mg (0.110 mmol) of the compound (2) was added to 1 g of activated Molecular Sieves AW-300 and 12 μl of BF₃.C₂H₅ was added to the obtained solution under cooling with ice in the presence of argon, followed by agitation for 1 hour. After agitation at room temperature for 12 hours, the reaction solution was filtered by Celite. Insolubles were washed with ethyl acetate and the washing solution was mixed with the filtrate. The resultant mixture was washed with water and then dried with MgSO₄. The reaction solution was concentrated under reduced pressure and the residue was purified by column chromatography using 20 g of silica gel (ethyl acetate: THF=4:1) to obtain 28 mg of the compound (3) (yield, 20.1%) and recover 116 mg of the compound (14).

Compound (3)

$[\alpha]_D^{20}$ +17.0 (C=0.20, CHCl₃).
Rf=0.45 (CHCl₃: CH₃OH=19:1) HPTLC.
¹HNMR CDCl₃, TMS, ppm (400 MHz): 1.580 (1H, t, J=12.8 Hz, H-3dax or H-3fax), 1.742 (1H, t, J=12.8 Hz, H-3fax or H-3dax), 1.411, 1.802, 1.843, 1.845, 1.893, 1.946, 1.962, 2.007, 2.049, 2.069, 2.129, 2.167, 2.273 (each, s, COCH₃), 2.494 (1H, dd, J=4.5, 12.0 Hz, H-3deq or H-3feq), 2.888 (1H, dd, J=4.8, 12.8 Hz, H-3feq or H-3deq), 3.691 (3H, s, OCH₃), 3.803 (3H, s, OCH₃, 6.937–7.889 (44H, m, aromatic protons).

Example 2 (Production of Compound (4))

15 mg of lithium iodide and 13 mg (5 mol) of the compound (3) were dissolved in 0.2 ml of pyridine and the pyridine solution was refluxed by heat for 3 hours. After being cooled, the reaction solution was diluted with chloroform, washed with diluted hydrochloric acid and saturated salt water, then dried with MgSO₄. The reaction solution was concentrated under reduced pressure and the residue was purified by silica gel column chromatography (1 g, 20% methanol-containing chloroform) to obtain 8.5 mg of the compound (4) (yield, 66%).

Compound (4)

Rf=0.32 (methanol: chloroform=1:4)

Example 3 (Production of Compound (5))

8.5 mg (3.38 γ mol) of the compound (4) was dissolved in 0.2 ml of ethanol and 23 mg of hydrazine hydrate was added to the ethanol solution, followed by heat reflux for 2 hours in the presence of argon. The mixture was concentrated under reduced pressure and the residue was dissolved in a mixed solvent of 0.2 ml of acetic anhydride and 0.2 ml of pyridine, followed by agitation at room temperature for 1 hour. After the solvent had been evaporated, the residue was dissolved in 0.5 ml of methanol and 0.1 ml of 0.5N CH₃ONa was added to the methanol solution, followed by agitation at room temperature for 1 hour. The resultant mixture was neutralized by Amberlist 15, the resins were then filtered off, and the solvent was evaporated. The residue was dissolved in a small amount of methanol and then purified by Sephadex LH-20 (methanol). The product was dissolved in 0.2 ml of a mixed solvent of methanol and water (3:1), and 5 mg of 10% Pd-C was then added to the obtained methanol solution, followed by catalytic reduction for 24 hours in the presence of a hydrogen gas. Pd-C was removed by filtration and the filtrate was concentrated under reduced pressure. The residue was purified by a Sephadex C-25 (H₂O) column (7mm×12 cm) to obtain 1.0 mg of the compound (5) (yield, 28%).

Compound (5)

Rf=0.27 (nBuOH: EtOH: H₂O=2:1:1) HPTLC.
¹HMR D₂O (internal standard acetone), 2.22), 27 C. 1.792 (1H, t, J=12.5 Hz, H-3feq), 1.906 (1H, t, J=12.7 Hz, H-3deq), 2.004 (3H, s, NHCOCH₃), 2.677 (1H, dd, J=5.1, 12.9 Hz, H-3deq), 2,745 (1H, dd, J=4.6, 12.7 Hz, H-3feq), 3.267 (0.5H), t, J=9.3 Hz, H-2aβ), 3.367 (1H, m, H-2b), 3.500 (1H, dd, H=2.7, 10.7 Hz, H-7d), 3.540 (1H, dd, J=2.7, 10.4 Hz, H-2e), 3.946 (1H, d, J=2.9 Hz, H-4e), 4.033 (1H, t, J=10.1 Hz, H-2C), 4.084 (1H, dd, J=3.4, 9.8 Hz, H-3e), 4.160 (1H, d, J=2.9 Hz, H-4c), 4.520 (1H, d, J=8.1 Hz, H-1b), 4.601 (1H, d, J=7.8 Hz, H-1e), 4.661 (0.5H, d, J=8.1 Hz, H-1aβ), 4.771 (1H, d, H=8.8 Hz, H-1c), 5.211 (0.5H, d, J=3.9 Hz, H-1aα).

What is claimed is:

1. Ganglioside GM₁ related compounds having the following formula:

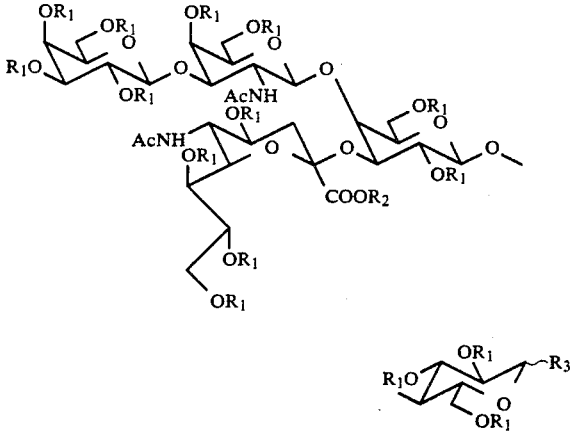

wherein R₁ represents H or Ac, wherein Ac is COCH₃; R₂ represents H or CH₃; and R₃ represents —OH, or

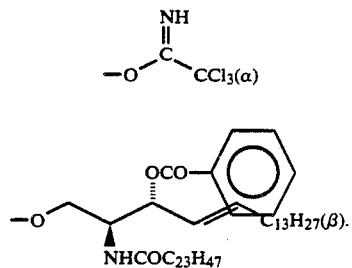

2. A method of producing ganglioside GM₁ related compounds having the following formula:

81

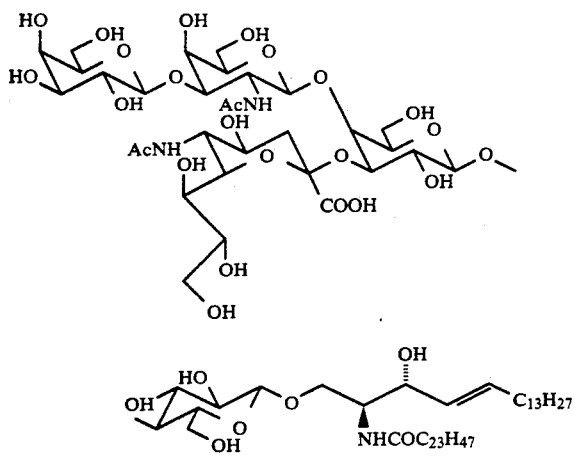

comprising the following steps:
(i) reacting Compound (1) having the formula (1):

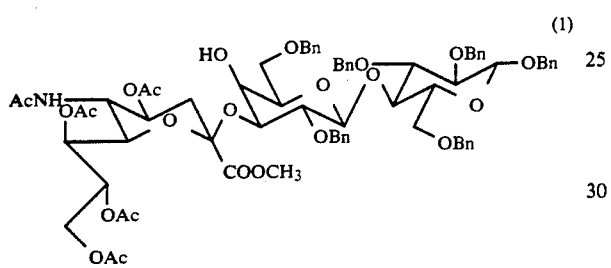

(1)

wherein Ac represents COCH₃ and Bn represents

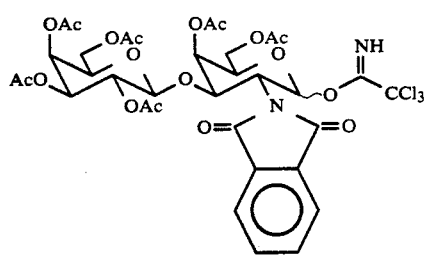

with Compound (2) having the formula (2):

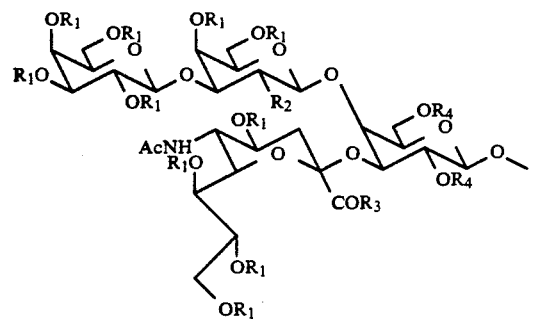

(2)

to obtain Compound (3)

(3)

82

-continued

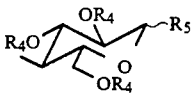

wherein $R_1$ represents Ac, $R_2$ represents

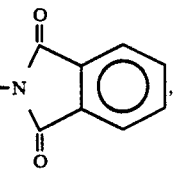

$R_3$ represents OCH₃, $R_4$ represents

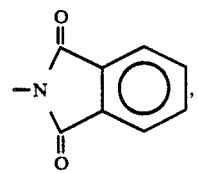

and $R_5$ represents

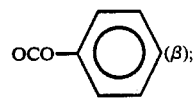

(β);

(ii) demethylating said compound (3) to obtain Compound (4):

(4)

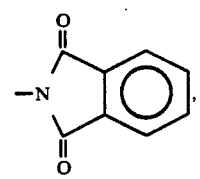

wherein $R_1$ represents Ac, $R_2$ represents $R_3$ represents OH, $R_4$ represents

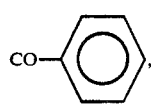

and R₅ represents

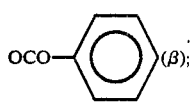

(iii) converting the phthalic acid imide group of said compound (4) to an amino group, and subsequently acetylating the resultant compound, to obtain Compound (5):

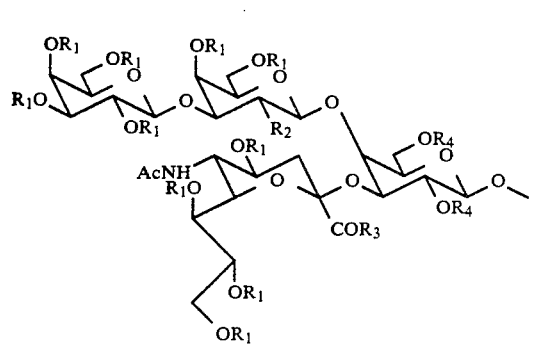

wherein $R_1$ represents Ac, $R_2$ represents —NHAc, $R_3$ represents OH, $R_4$ represents

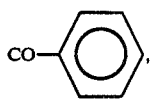

and R₅ represents

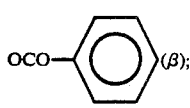

(iv) converting the carboxyl group of said compound (5) to a methyl ester group to obtain Compound (6):

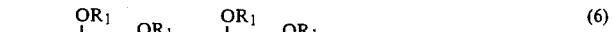

wherein $R_1$ represents Ac, $R_2$ represents —NHAc, $R_3$ represents OCH₃, $R_4$ represents

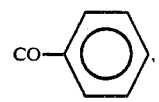

and R₅ represents

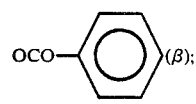

(v) debenzoylating said compound (6) and subsequently acetylating the resultant compound to obtain Compound (7):

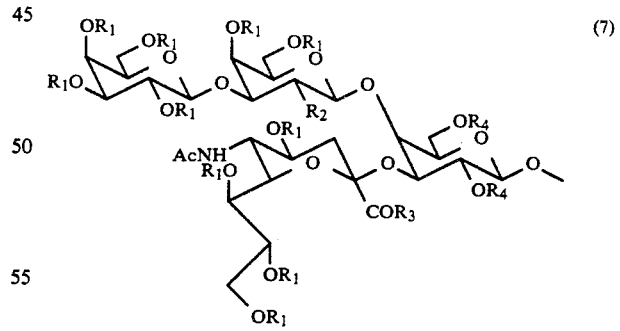

wherein $R_1=R_4=$Ac, $R_2$ represents —NHAc, $R_3$ represents OCH₃, and $R_5$ represents OCOCH₃;

(vi) treating said compound (7) with hydrazinium acetate to obtain Compound (8):

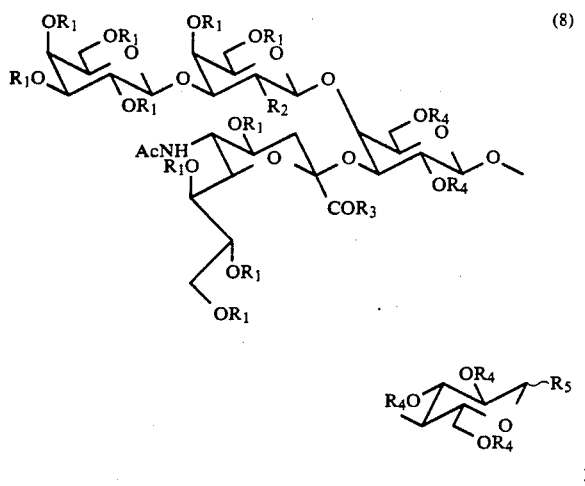

(8)

wherein $R_1=R_4=Ac$, $R_2$ represents NHAc, $R_3$ represents $OCH_3$, and $R_5$ represents OH;

(vii) treating said compound (8) with $CCl_3CN$ and NaH or 1,8-diazabicyclo[5.4.0]undecatriene to obtain Compound (9):

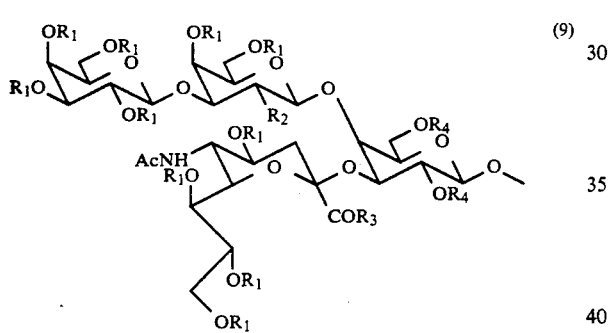

(9)

wherein $R_1=R_4=Ac$, $R_2$ represents NHAc, $R_3$ represents $OCH_3$, and $R_5$ represents

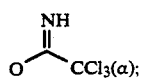

(viii) reacting a benzoylated ceramide compound (10), having the following formula (10):

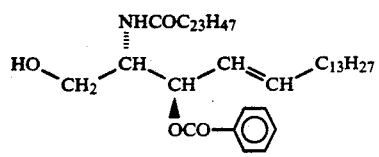

(10)

with said compound (9) to obtain Compound (11):

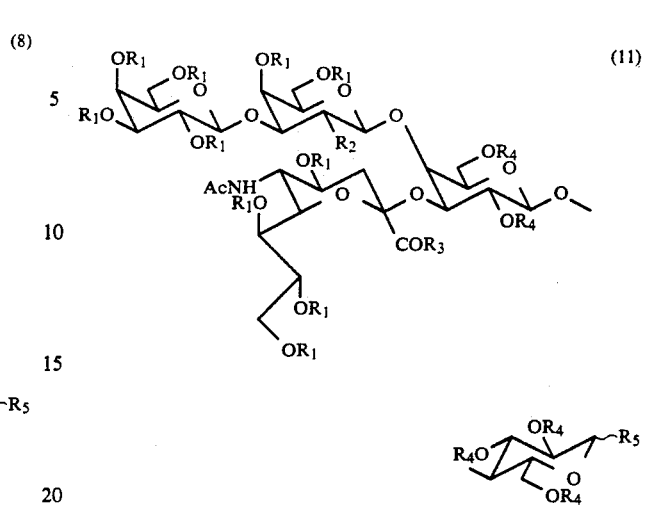

(11)

wherein $R_1=R_4=Ac$, $R_2$ represents —NHAc, $R_3$ represents $OCH_3$, and $R_5$ represents

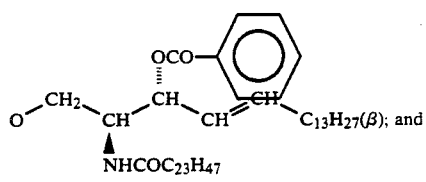

(ix) subjecting said compound (11) to debenzoylation, deacetylation, and demethylation.

3. A method of producing ganglioside $GM_1$ related compounds having the following formula:

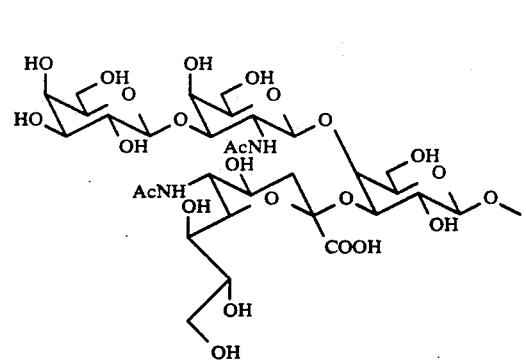

comprising the steps:

(i) debenzoylating a compound having the formula (6):

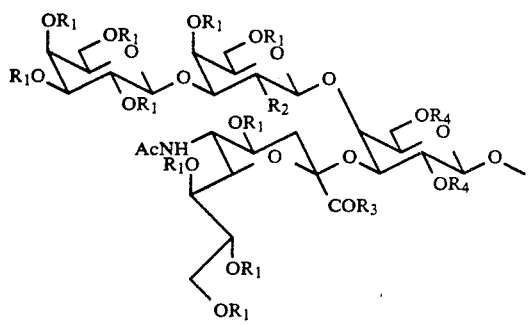

(6)

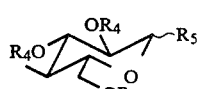

wherein $R_1$ represents Ac, $R_2$ represents —NHAc, $R_3$ represents $OCH_3$, $R_4$ represents

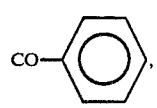

and $R_5$ represents

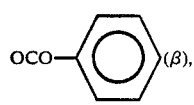

to obtain compound (7):

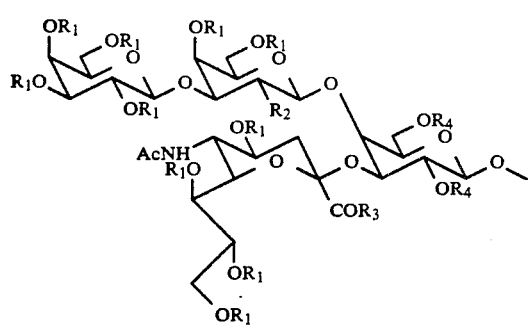

(7)

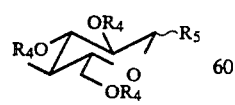

wherein $R_1 = R_4 = Ac$, $R_2$ represents —NHAc, $R_3$ represents $OCH_3$, and $R_5$ represents $OCOCH_3$;

(ii) treating said compound (7) with hydrazinium acetate to obtain Compound (8):

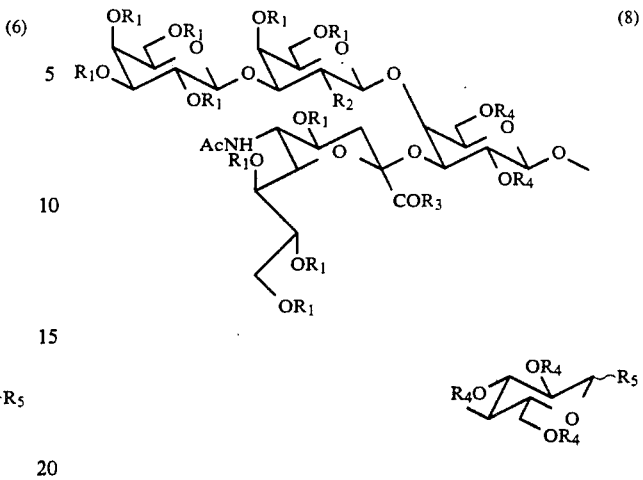

(8)

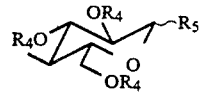

wherein $R_1 = R_4 = Ac$, $R_2$ represents NHAc, $R_3$ represents $OCH_3$, and $R_5$ represents OH;

(iii) treating said compound (8) with $CCl_3CN$ and NaH or 1,8-diazabicyclo[5.4.0]undecatriene to obtain Compound (9):

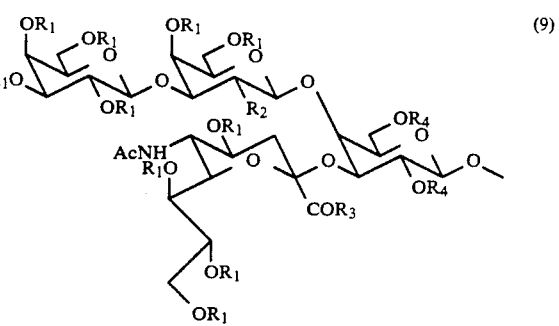

(9)

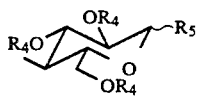

wherein $R_1 = R_4 = Ac$, $R_2$ represents NHAc, $R_3$ represents $OCH_3$, and $R_5$ represents

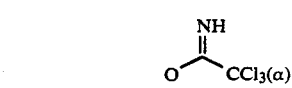

(iv) reacting a benzoylated ceramide compound having the following formula (10):

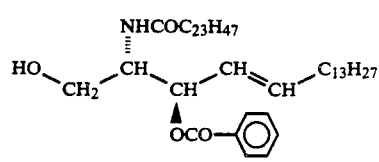

(10)

with said compound (9) to obtain Compound (11):

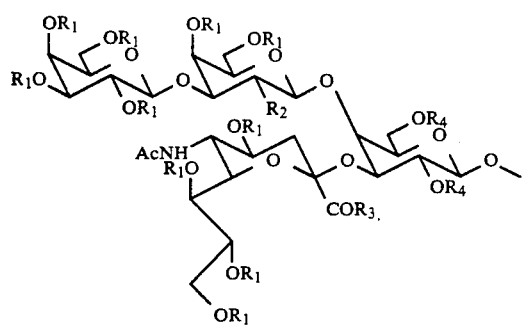
(11)
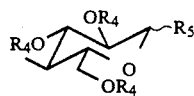
wherein $R_1=R_4=Ac$, $R_2$ represents —NHAc, $R_3$ represents $OCH_3$, and $R_5$ represents
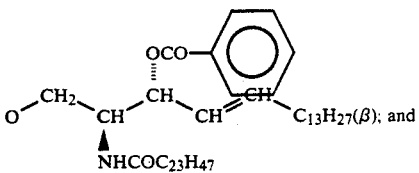
(v) subjecting said compound (11) to debenzoylation, deacetylation, and demethylation.
* * * * *